(12) United States Patent
Sperinde et al.

(10) Patent No.: US 10,273,308 B2
(45) Date of Patent: Apr. 30, 2019

(54) METHODS OF PRODUCING ANTIBODIES SPECIFIC FOR P95

(71) Applicant: Laboratory Corporation of America Holdings, Burlington, NC (US)

(72) Inventors: Jeff Sperinde, El Granada, CA (US); John William Winslow, El Granada, CA (US); Xueguang Jin, Fremont, CA (US); Gerald J. Wallweber, Foster City, CA (US)

(73) Assignee: Laboratory Corporation of America Holdings, Burlington, NC (US)

( * ) Notice: Subject to any disclaimer, the term of this patent is extended or adjusted under 35 U.S.C. 154(b) by 0 days.

(21) Appl. No.: 14/737,742

(22) Filed: Jun. 12, 2015

(65) Prior Publication Data

US 2015/0376293 A1 Dec. 31, 2015

Related U.S. Application Data

(60) Continuation of application No. 13/911,329, filed on Jun. 6, 2013, now Pat. No. 9,081,019, which is a division of application No. 12/629,037, filed on Dec. 1, 2009, now Pat. No. 8,470,542.

(60) Provisional application No. 61/118,975, filed on Dec. 1, 2008, provisional application No. 61/182,282, filed on May 29, 2009, provisional application No. 61/187,960, filed on Jun. 17, 2009.

(51) Int. Cl.
| | |
|---|---|
| *C07K 16/30* | (2006.01) |
| *C07K 16/32* | (2006.01) |
| *C12Q 1/6886* | (2018.01) |
| *G01N 33/574* | (2006.01) |
| *G01N 33/74* | (2006.01) |
| *G01N 33/68* | (2006.01) |
| *G01N 33/50* | (2006.01) |
| *A61P 35/00* | (2006.01) |

(52) U.S. Cl.
CPC .............. *C07K 16/32* (2013.01); *A61P 35/00* (2018.01); *C12Q 1/6886* (2013.01); *G01N 33/5005* (2013.01); *G01N 33/57415* (2013.01); *G01N 33/57484* (2013.01); *G01N 33/6893* (2013.01); *G01N 33/74* (2013.01); *C07K 2317/30* (2013.01); *C07K 2317/34* (2013.01); *C07K 2317/73* (2013.01); *C12Q 2600/158* (2013.01); *G01N 2333/71* (2013.01); *G01N 2800/52* (2013.01)

(58) Field of Classification Search
None
See application file for complete search history.

(56) References Cited

U.S. PATENT DOCUMENTS

| | | | |
|---|---|---|---|
| 4,318,846 A | 3/1982 | Khanna et al. | |
| 4,650,750 A | 3/1987 | Giese | |
| 4,720,455 A * | 1/1988 | Babu .................... | C07K 16/26 435/336 |
| 4,968,603 A | 11/1990 | Slamon et al. | |
| 5,340,716 A | 8/1994 | Ullman et al. | |
| 5,360,819 A | 11/1994 | Giese | |
| 5,480,968 A | 1/1996 | Kraus et al. | |
| 5,516,636 A | 5/1996 | McCapra | |
| 5,516,931 A | 5/1996 | Giese et al. | |
| 5,536,834 A | 7/1996 | Singh et al. | |
| 5,565,324 A | 10/1996 | Still et al. | |
| 5,565,552 A | 10/1996 | Magda et al. | |
| 5,602,273 A | 2/1997 | Giese et al. | |
| 5,622,929 A | 4/1997 | Willner et al. | |
| 5,677,171 A | 10/1997 | Hudziak et al. | |
| 5,709,994 A | 1/1998 | Pease et al. | |
| 5,763,602 A | 6/1998 | Li et al. | |
| 5,772,997 A | 6/1998 | Hudziak et al. | |
| 5,945,526 A | 8/1999 | Lee et al. | |
| 5,968,511 A | 10/1999 | Akita et al. | |
| 5,986,076 A | 11/1999 | Rothschild et al. | |
| 6,001,673 A | 12/1999 | Marcinkiewicz | |
| 6,204,007 B1 | 3/2001 | Owens et al. | |
| 6,251,581 B1 | 6/2001 | Ullman et al. | |
| 6,322,980 B1 | 11/2001 | Singh | |
| 6,514,700 B1 | 2/2003 | Singh | |
| 6,627,400 B1 | 9/2003 | Singh et al. | |
| 6,630,296 B2 | 10/2003 | Xue et al. | |
| 6,649,351 B2 | 11/2003 | Matray et al. | |
| 6,673,550 B2 | 1/2004 | Matray et al. | |
| 6,682,887 B1 | 1/2004 | Singh | |
| 6,686,152 B2 | 2/2004 | Singh et al. | |
| 6,770,439 B2 | 8/2004 | Singh et al. | |
| 6,818,399 B2 | 11/2004 | Singh et al. | |
| 6,846,645 B2 | 1/2005 | Xue et al. | |
| 6,916,612 B2 | 7/2005 | Singh et al. | |
| 6,949,347 B2 | 9/2005 | Singh et al. | |
| 6,955,874 B2 | 10/2005 | Singh et al. | |

(Continued)

FOREIGN PATENT DOCUMENTS

| | | |
|---|---|---|
| AU | 2001279222 | 8/2001 |
| CA | 2403326 | 11/2001 |

(Continued)

OTHER PUBLICATIONS

Scaltriti et al, J Natil Can Ins 2007, 99:628-638.*

(Continued)

*Primary Examiner* — Lei Yao

(74) *Attorney, Agent, or Firm* — Kilpatrick Townsend & Stockton LLP

(57) ABSTRACT

The disclosure provides methods of making antibodies specific for p95.

3 Claims, 23 Drawing Sheets

Specification includes a Sequence Listing.

(56) References Cited

U.S. PATENT DOCUMENTS

| | | |
|---|---|---|
| 7,001,725 B2 | 2/2006 | Singh et al. |
| 7,037,654 B2 | 5/2006 | Chenna et al. |
| 7,041,459 B2 | 5/2006 | Singh et al. |
| 7,045,311 B2 | 5/2006 | Ciambrone et al. |
| 7,105,308 B2 | 9/2006 | Chan-Hui et al. |
| 7,135,174 B2 | 11/2006 | Corvalan et al. |
| 7,135,300 B2 | 11/2006 | Chan-Hui et al. |
| 7,160,735 B2 | 1/2007 | Dehlinger et al. |
| 7,183,388 B2 | 2/2007 | Denardo et al. |
| 7,217,531 B2 | 5/2007 | Singh et al. |
| 7,255,999 B2 | 8/2007 | Singh et al. |
| 7,279,585 B2 | 10/2007 | Singh et al. |
| 7,306,904 B2 | 12/2007 | Landegren et al. |
| 7,312,034 B2 | 12/2007 | Virgos et al. |
| 7,320,860 B2 | 1/2008 | Landegren et al. |
| 7,332,580 B2 | 2/2008 | Adams et al. |
| 7,348,010 B2 | 3/2008 | Zielinski et al. |
| 7,351,528 B2 | 4/2008 | Landegren |
| 7,358,052 B2 | 4/2008 | Singh |
| 7,371,376 B1 | 5/2008 | Fendly |
| 7,402,397 B2 | 7/2008 | Chan-Hui et al. |
| 7,402,398 B2 | 7/2008 | Pidaparthi et al. |
| 7,402,399 B2 | 7/2008 | Mukherjeei et al. |
| 7,446,185 B2 | 11/2008 | Nelson |
| 7,537,938 B2 | 5/2009 | Kirakossian et al. |
| 7,648,828 B2 | 1/2010 | Chan-Hui et al. |
| 7,700,299 B2 | 4/2010 | Moecks et al. |
| 7,771,929 B2 | 8/2010 | Singh et al. |
| 7,919,086 B2 | 4/2011 | Nakano et al. |
| 7,939,267 B2 | 5/2011 | Moore et al. |
| 8,093,216 B2 | 1/2012 | Clinton |
| 8,198,031 B2 | 6/2012 | Chan-Yui et al. |
| 8,247,180 B2 | 8/2012 | Pidaparthi et al. |
| 8,349,574 B2 | 1/2013 | Bates et al. |
| 8,389,227 B2 | 3/2013 | Lopez et al. |
| 8,470,542 B2 | 6/2013 | Sperinde et al. |
| 8,741,586 B2 | 6/2014 | Arribas Lopez et al. |
| 9,081,019 B2 | 7/2015 | Sperinde et al. |
| 2002/0045738 A1 | 4/2002 | Singh et al. |
| 2002/0045748 A1 | 4/2002 | Singh et al. |
| 2002/0058263 A1 | 5/2002 | Singh et al. |
| 2002/0146726 A1 | 10/2002 | Matray et al. |
| 2003/0059863 A1 | 3/2003 | Clinton |
| 2003/0092012 A1 | 5/2003 | Chenna et al. |
| 2003/0157109 A1 | 8/2003 | Corvalan et al. |
| 2003/0170734 A1 | 9/2003 | Williams et al. |
| 2003/0170915 A1 | 9/2003 | Singh et al. |
| 2003/0175747 A1 | 9/2003 | Singh |
| 2003/0203408 A1 | 10/2003 | Williams et al. |
| 2003/0207300 A1 | 11/2003 | Matray et al. |
| 2003/0235832 A1 | 12/2003 | Chenna et al. |
| 2004/0005643 A1 | 1/2004 | De Santis et al. |
| 2004/0005647 A1 | 1/2004 | Denardo et al. |
| 2004/0029139 A1 | 2/2004 | Singh |
| 2004/0052811 A1 | 3/2004 | Zielinski |
| 2004/0067498 A1 | 4/2004 | Chenna et al. |
| 2004/0071696 A1 | 4/2004 | Adams et al. |
| 2004/0091850 A1 | 5/2004 | Boone et al. |
| 2004/0166529 A1 | 8/2004 | Singh et al. |
| 2004/0175765 A1 | 9/2004 | Singh et al. |
| 2004/0197815 A1 | 10/2004 | Singh et al. |
| 2004/0229293 A1 | 11/2004 | Chan-Hui et al. |
| 2004/0229294 A1 | 11/2004 | Chan-Hui et al. |
| 2004/0229299 A1 | 11/2004 | Badal et al. |
| 2004/0229380 A1 | 11/2004 | Chan-Hui et al. |
| 2004/0241686 A1 | 12/2004 | Nelson |
| 2004/0248150 A1 | 12/2004 | Singh et al. |
| 2004/0248151 A1 | 12/2004 | Bacus et al. |
| 2004/0248325 A1 | 12/2004 | Bukusoglu |
| 2004/0265858 A1 | 12/2004 | Singh et al. |
| 2005/0048553 A1 | 3/2005 | Chenna et al. |
| 2005/0130238 A1 | 6/2005 | Chan-Hui et al. |
| 2005/0130246 A1 | 6/2005 | Salimi-Moosavi et al. |
| 2005/0131006 A1 | 6/2005 | Mukherjee et al. |
| 2005/0170438 A1 | 8/2005 | Chan-Hui et al. |
| 2005/0226872 A1 | 10/2005 | Adam et al. |
| 2006/0127928 A1 | 6/2006 | Bacus et al. |
| 2006/0199231 A1 | 9/2006 | Moore et al. |
| 2006/0204966 A1 | 9/2006 | Spector et al. |
| 2006/0212956 A1 | 9/2006 | Crocker et al. |
| 2006/0223107 A1 | 10/2006 | Chenna et al. |
| 2006/0275305 A1 | 12/2006 | Bryant |
| 2007/0037228 A1 | 2/2007 | Moecks et al. |
| 2007/0059785 A1 | 3/2007 | Bacus et al. |
| 2007/0190599 A1 | 8/2007 | Nakano et al. |
| 2007/0203408 A1 | 8/2007 | Say et al. |
| 2007/0292419 A1* | 12/2007 | Hellmann .......... A61K 31/7068 424/133.1 |
| 2008/0131883 A1 | 6/2008 | Adams et al. |
| 2008/0182255 A1 | 7/2008 | Baker et al. |
| 2008/0187948 A1 | 8/2008 | Chan-Hui et al. |
| 2008/0233602 A1 | 9/2008 | Chan-Hui et al. |
| 2008/0254497 A1 | 10/2008 | Singh |
| 2008/0311674 A1 | 12/2008 | Singh et al. |
| 2009/0011432 A1 | 1/2009 | Chan-Hui et al. |
| 2009/0011440 A1 | 1/2009 | Mukherjee et al. |
| 2009/0092617 A1 | 4/2009 | Bock et al. |
| 2009/0111127 A1 | 4/2009 | Chan-Hui et al. |
| 2009/0155818 A1 | 6/2009 | Pidaparthi et al. |
| 2009/0155819 A1 | 6/2009 | Erlenbach et al. |
| 2009/0173631 A1 | 7/2009 | Boone et al. |
| 2009/0191559 A1 | 7/2009 | Huang et al. |
| 2009/0311262 A1 | 12/2009 | Lopez et al. |
| 2010/0143927 A1 | 6/2010 | Sperinde et al. |
| 2010/0210034 A1 | 8/2010 | Bates et al. |
| 2010/0233732 A1 | 9/2010 | Bates et al. |
| 2010/0291594 A1 | 11/2010 | Chan-Hui et al. |
| 2011/0180408 A1 | 7/2011 | Badal et al. |
| 2011/0318380 A1 | 12/2011 | Brix et al. |

FOREIGN PATENT DOCUMENTS

| | | |
|---|---|---|
| CN | 1639192 | 7/2005 |
| CN | 1928563 | 3/2007 |
| CN | 101115836 | 1/2008 |
| CN | 101230390 | 7/2008 |
| EP | 0484027 | 12/1996 |
| EP | 1278760 | 6/2008 |
| EP | 1918386 | 7/2008 |
| EP | 1540347 | 9/2009 |
| EP | 2293819 | 3/2011 |
| EP | 2330131 | 10/2014 |
| ES | 2342646 | 7/2010 |
| JP | 05117165 | * 5/1993 |
| JP | 2006-521821 | 9/2006 |
| JP | 2006-508336 | 11/2012 |
| JP | 5117165 | 1/2013 |
| WO | WO 1993/016185 | 8/1993 |
| WO | WO 98/06863 | 2/1998 |
| WO | WO 99/31140 | 6/1999 |
| WO | WO 00/66607 | 11/2000 |
| WO | WO 00/69460 | 11/2000 |
| WO | WO 01/15730 | 3/2001 |
| WO | WO 01/83502 | 11/2001 |
| WO | WO 01/84157 | 11/2001 |
| WO | WO 02/12547 | 2/2002 |
| WO | WO 02/94998 | 11/2002 |
| WO | WO 02/95356 | 11/2002 |
| WO | WO 03/006947 | 1/2003 |
| WO | WO 2003/013602 | 2/2003 |
| WO | WO 03/032867 | 4/2003 |
| WO | WO 03/033741 | 4/2003 |
| WO | WO 03/042398 | 5/2003 |
| WO | WO 03/042657 | 5/2003 |
| WO | WO 03/042658 | 5/2003 |
| WO | WO 03/42699 | 5/2003 |
| WO | WO 03/051669 | 6/2003 |
| WO | WO 03/76649 | 9/2003 |
| WO | WO 03/085374 | 10/2003 |
| WO | WO 2004/000915 | 12/2003 |
| WO | WO 04/008099 | 1/2004 |
| WO | WO 04/010842 | 2/2004 |
| WO | WO 04/011900 | 2/2004 |
| WO | WO 04/061131 | 7/2004 |

(56) References Cited

FOREIGN PATENT DOCUMENTS

| | | |
|---|---|---|
| WO | WO 04/061446 | 7/2004 |
| WO | WO 04/063700 | 7/2004 |
| WO | WO 04/068116 | 8/2004 |
| WO | WO 04/087887 | 10/2004 |
| WO | WO 04/091384 | 10/2004 |
| WO | WO 04/092353 | 10/2004 |
| WO | WO 05/011607 | 2/2005 |
| WO | WO 05/019470 | 3/2005 |
| WO | WO 05/037071 | 4/2005 |
| WO | WO 05/045058 | 5/2005 |
| WO | WO 05/072507 | 8/2005 |
| WO | WO 06/044748 | 4/2006 |
| WO | WO 06/052788 | 5/2006 |
| WO | WO 06/068840 | 6/2006 |
| WO | WO 06/084018 | 8/2006 |
| WO | WO 07/041502 | 4/2007 |
| WO | WO 08/145338 | 12/2008 |
| WO | WO 09/070772 | 6/2009 |
| WO | WO 09/086197 | 7/2009 |
| WO | WO 10/000565 | 1/2010 |
| WO | WO 10/065568 | 6/2010 |
| WO | WO 10/083463 | 7/2010 |
| WO | WO 10/083470 | 7/2010 |
| WO | WO 2013/033623 | 3/2013 |

OTHER PUBLICATIONS

Anido et al, The EMBO 25:3234-44, 2006.*
Anido, J., et al., "Biosynthesis of tumorigenic HER2 C-terminal Fragments by Alternative Initiation of Translation," EMBO J., 2006, 25:3234-3244.
Atkinson, A., et al., "Biomarkers and Surrogate Endpoints: Preferred Definitions and Conceptual Framework Biomarkers and Surrogate Endpoints: Preferred Definitions and Conceptual Framework," Clin. Pharmacol. Ther., 2001, 69:89-95.
Bagashawe, K., et al., "A Cytotoxic Agent Can Be Generated Selectively at Cancer Sites," Br. J. Cancer, 1987, 58:(6):700-703.
Theory and Practice of Histological Techniques, (Bancroft, J.D. and Stevens, A., eds.) 1977, Churchill Livingstone, Edinburgh.
Beutner, S., et al., "Synthetic Singlet Oxygen Quenchers," Methods in Enzymology, 2000, 319:226-241.
Blume-Jensen, P. and Hunter, T., "Oncogenic Kinase Signalling," Nature, 2001, 411:355-365.
Carter, P. et al., "High Level *Escherichia coli* Expression and Production of a Bivalent Humanized Antibody Fragment," Bio/Technology, 1992, 10:163-167.
Carter, P. et al., "Humanization of an Anti-p185$^{HER2}$ Antibody for Human Cancer Therapy," Proc. Natl. Acad. Sci. USA, 1992, 89:4285-4289.
Carter, P. and Senter, P., "Antibody-Drug Conjugates for Cancer Therapy," The Cancer Journal, 2008, 14(3):154-169.
Chothia, C, et al., "Canonical Structures for the Hypervariable Regions of Immunoglobulins," J. Mol. Biol., 1987, 196:901-917.
Conover, W. J., Practical Nonparametric Statistics, 3$^{rd}$ Ed, 1999.
DiMascio, P. et al., "Singlet Molecular Oxygen Production in the Reaction of Peroxynitrite With Hydrogen Peroxide," FEBS Letters, 1994, 355:287-289.
Engvall, E., "Enzyme-Linked Immunosorbent Assay, ELISA," In: Biomedical Applications of Immobilized Enzymes and Proteins, 1977, (Chang, T. ed.), 2:87-96, Plenum Press, New York.
Frank, R. and Hargreaves, R., "Clinical Biomarkers in Drug Discovery and Development," Nature Reviews Drug Discovery, 2003, 2:566-580.
Gee, J. and Knowlden J., "ADAM Metalloproteases and EGFR Signalling," Breast Cancer Res., 2003, 5:223-224.
Genbank accession No. X03363, "Human c-erb-B-2 mRNA," Mar. 30, 1995.
George, S. et al., "G-Protein-Coupled Receptor Oligomerization and Its Potential for Drug Discovery," Nature Reviews Drug Discovery, 2002, 1:. 808-820.

Giese, R., "Electrophoric Release Tags: Ultrasensitive Molecular Labels Providing Multiplicity," Anal. Chem., 1983, 2(7):165-168.
Goding, J., "Antibody Production by Hybridomas," J. Immunol. Methods, 1980, 39:285-308.
Goldenberg, M., "Trastuzumab, A Recombinant DNA-Derived Humanized Monoclonal Antibody, A Novel Agent for the Treatment of Metastatic Breast Cancer," Clin. Ther., 1999, 21(2):309-318.
Protective Groups in Organic Synthesis, 2nd ed., (Greene, T.W. and Wuts, P.G.M. eds.), 1991, John Wiley & Sons, New York.
Antibodies: A Laboratory Manual, (Harlow, E. and Lane, D. eds.), 1988, Cold Spring Harbor Laboratory Press, New York.
Harris, J. and Chess, R., "Effect of Pegylation on Pharmaceuticals," Nat. Rev. Drug Discov., 2003, 2:214-221.
Herbst, R. and Shin, D., "Monoclonal Antibodies to Target Epidermal Growth Factor Receptor-Positive Tumors," Cancer, 2002, 94:1593-1611.
Hermanson, G.T., Bioconjugate Techniques, 1996, Academic Press, New York.
Huang, W. et al., "Comparison of Central HER-2 Tests With Quantitative HER-2 Expression and HER-2 Homodimer Measurements Using a Novel Proximity Based Assay," Abstract 40, American College of Pathologist Annual Meeting, Sep. 25-28, 2008. Available on the Internet: <URL:http://www.hermarkassay.com/publications.aspx>.
Jones, P. et al., "Replacing the Complementarity-Determining Regions in a Human Antibody With Those From a Mouse," Nature, 1986, 321:522-525.
Kanofsky, J., "Singlet Oxygen Production by Lactoperoxidase," J. Biol. Chem., 1983, 258:5991-5993.
Kearney, J.F. et al., "A New Mouse Myeloma Cell Line That Has Lost Immunoglobin Expression But Permits the Construction of Antibody-Secreting Hybrid Cell Lines," J. Immunology, 1979, 123:1548-1550.
Monoclonal Antibodies, (Kennett, R., et al. eds.), 1980, Plenum Press, New York.
Koehler, G. et al., "Continuous Cultures of Fused Cells Secreting Antibody of Predefined Specificity," Nature, 1975, 256:495-497.
Kreitman, R., "Immunotoxins for Targeted Cancer Therapy," AAPS J., 2006, 18(3):E532-E551.
Manual of Histological Staining Method of the Armed Forces Institute of Pathology, 3rd edition, (Luna, L.G., ed.), 1960, McGraw-Hill Book Company (Blakston Division), New York.
Liu, P. et al., "Identification of ADAM10 as a Major Source of HER2 Ectodomain Sheddase Activity in HER2 Overexpressing Breast Cancer Cells," Cancer Biol. Therapy, 2006, 6:657-664.
Lizardi, P. et al., "Mutation Detection and Single-Molecule Counting Using Isothermal Roving-Circle Amplification," Nat. Genet., 1998, 19:225-232.
Martin, J. et al., "Production of Oxygen Radicals by Photosensitization," Methods Enzymol., 1990, 186:635-645.
McCormick, F., "Signalling Networks That Cause Cancer," Trends in Cell Biology, 1999, 9:53-56.
Mellado, M. et al., "Chemokine Signaling and Functional Responses: The Role of Receptor Dimerization and TK Pathway Activation," Ann. Rev. Immunol., 2001, 19:397-421.
The Armed Forces Institute of Pathology Advanced Laboratory Methods in Histology and Pathology, Armed Forces Institute of Pathology, American Registry of Pathology, (Mikel, U.V. ed.), 1994, Washington, DC.
Mignot, G. et al., "Prospects for Exosomes in Immunotherapy of Cancer," J. Cell. Mol. Med., 2006, 10(2):376-388.
Molina, M. et al., "NH$_2$-terminal Truncated HER-2 Protein but Not Full-Length Receptor Is Associated With Nodal Metastasis in Human Breast Cancer," Clin. Can. Res., 2002, 8:347-353.
Mosession, Y. et al., "Oncogenic Growth Factor Receptors: Implications for Signal Transduction Therapy," Semin. Cancer Biol., 2004, 14:262-270.
Pearse, A., Histochemistry, Theory and Applied. 4th ed., 1980, Churchill Livingstone, Edinburgh, UK.
Petricoin, E. et al., "Clinical Proteomics: Translating Benchside Promise Into Bedside Reality," Nature Reviews Drug Discovery, 2002, 1:683-695.

(56) References Cited

OTHER PUBLICATIONS

Pierlot, C. et al., "Naphtalene Endoperoxides as Generators of Singlet Oxygen in Biological Media," Meth. Enzymol., 2000, 319:3-20.

Plückthun, A., "Mono- and Bivalent Antibody Fragments Produced in *Escherichia coli*: Engineering, Folding and Antigen Binding," Immunological Rev., 1992, 130:151-188.

Presta, L. et al., "Humanization of an Antibody Directed Against IgE," J. Immunol., 1993, 151:2623-2632.

Riechmann, L. et al., "Reshaping Human Antibodies for Therapy," Nature, 1988, 332:323-327.

Romond, E., "Trastuzumab Plus Adjuvant Chemotherapy for Operable HER2- Positive Breast Cancer," N. Engl. J. Med., 2005, 353(16):1673-1684.

Saez, R. et al., "p95HER-2 Predicts Worse Outcome in Patients With HER-2-Positive Breast Cancer," Clin. Cancer Res., 2006, 12(2):424-431.

Sahin, U. et al., "Distinct Roles for ADAM10 and ADAM17 in Ectodomain Shedding of Six EGFR Ligands," J. Cell Biol., 2004, 164(5):769-779.

Schlessinger, J., "Cell Signaling by Receptor Tyrosine Kinases," Cell, 2000, 103:211-225.

Semba, K. et al., "A v-erbB-Related Protooncogene, c-erbB-2, Is Distinct From the c-erbB-1/Epidermal Growth Factor-Receptor Gene and Is Amplified in a Human Salivary Gland Adenocarcinoma," Proc. Natl. Acad. Sci. USA, 1985, 82:6497-6501.

Senter, P. et al., "Anti-Tumor Effects of Antibody-Alkaline Phosphatase Conjugates in Combination With Etoposide Phosphate," Proc. Natl. Acad. Sci. USA, 1988, 85:4842-4846.

Shak, S., "Overview of the Trastuzumab (Herceptin) Anti-HER2 Monoclonal Antibody Clinical Program in HER2-Overexpressing Metastatic Breast Cancer," Semin Oncol., 1999, 26(4):71-77.

Sidransky, D., "Emerging Molecular Markers of Cancer," Nature Reviews Cancer, 2002, 2:210-219.

Sims, M. et al., "A Humanized CD18 Antibody Can Block Function Without Cell Destruction," J. Immunol., 1993, 151:2296-2308.

"Radioimmunoassay and Saturation Analysis," British Medical Bulletin, (Sonksen, P.H. ed.), 1974, 30:1-103.

Spector, N. et al., "Small Molecule HER-2 Tyrosine Kinase Inhibitors," Breast Cancer Res., 2007, 9:205-212.

Strong, L. et al., "Antibody-Targeted Photolysis," Ann. New York Acad. Sci., 1994, 745:297-320.

Taylor, D. et al., "Inhibition of Macrophage Ia Antigen Expression by Shed Plasma Membrane Vesicles From Metastatic Murine Melanoma Lines," J. Natl. Cancer Inst., 1985, 74:859-867.

Therasse, P. et al., "New Guidelines to Evaluate the Response to Treatment in Solid Tumors," J. Natl. Cancer Inst., 2000, 92:205-216.

Ullman, E. et al., "Luminescent Oxygen Channeling Immunoassay: Measurement of Particle Binding Kinetics by Chemiluminescence," Proc. Natl. Acad. Sci. USA, 1994, 91:5426-5430.

Verhoeyen, M. et al., "Reshaping Human Antibodies: Grafting an Antilysozyme Activity," Science, 1988, 239:1534-1536.

Voller, A. et al., "Enzyme Immunoassays With Special Reference to ELISA Techniques," J. Clin. Pathol., 1978, 31:507-520.

The Immunoassay Handbook, (Wild, D. ed.), 1994, Stockton Press, New York.

Xia, W. et al., "Truncated ErbB2 Receptor (p95$^{ErbB2}$) Is Regulated by Heregulin Through Heterodimer Formation With ErbB3 Yet Remains Sensitive to the Dual EGFR/ErbB2 Kinase Inhibitor GW572016," Oncogene, 2004, 23(3):646-653.

Yamamoto, T. et al., "Similarity of Protein Encoded by the Human c-erb-B-2 Gene to Epidermal Growth Factor Receptor," Nature, 1986, 319:230-234.

Yarden, Y, and Sliwkowski, M., "Untangling the ErbB Signalling Network," Nat. Rev. Mol. Cell Biol., 2001, 2:127-137.

Yarden, Y., "The EGFR Family and Its Ligands in Human Cancer: Signalling Mechanisms and Therapeutic Opportunities," Eur. J. Cancer, 2001, 37:S3-S8.

Yarmush, M. et al., "Antibody Targeted Photolysis," Crit. Rev. Therap. Drug Carrier Syst., 1993, 10(3):197-252.

Zabrecky, J. et al., "The Extracellular Domain of p185/neu Is Released From the Surface of Human Breast Carcinoma Cells, SK-BR-3," J. Biol. Chem., 1991, 266(3):1716-1720.

Zhang, X. et al., "Synthesis of Releasable Electrophore Tags for Applications in Mass Spectrometry," Bioconjugate Chem., 2002, 13:1002-1012.

Zola, H., "Monoclonal Antibodies: A Manual of Techniques," 1987, CRC Press, Boca Raton, Florida.

International Search Report and Written Opinion dated May 25, 2010 for corresponding PCT Application No. PCT/US2009/66295.

Patent Cooperation Treaty, International Search Report and Written Opinion, International Application No. PCT/US10/21281, dated Jun. 2, 2010.

Patent Cooperation Treaty, International Search Report and Written Opinion, International Application No. PCT/US10/21272, dated Mar. 1, 2010.

Patent Cooperation Treaty, International Search Report and Written Opinion, International Application No. PCT/US08/87828, dated Mar. 17, 2009.

Patent Cooperation Treaty, Preliminary Report on Patentability, International Application No. PCT/US10/21281, dated Jul. 28, 2011.

Patent Cooperation Treaty, Preliminary Report on Patentability, International Application No. PCT/US10/21272, dated Dec. 2, 2011.

Patent Cooperation Treaty, Preliminary Report on Patentability, International Application No. PCT/US08/87828, dated Jun. 22, 2010.

Eli, L., et al., "Development of Novel Proximity-Based Immunoassays for the Detection of HER Heterodimerization in Breast Cancer Cell Line Lysates and Formalin-Fixed, Paraffin-Embedded Tissue," Breast Cancer Research and Treatment, Dec. 13, 2007, 106(1):S87-S88 (Abstract).

Eli, L., et al., "Development of Novel Proximity-Based Immunoassays for the Detection of HER Heterodimerization in Breast Cancer Cell Line Lysates and Formalin-Fixed, Paraffin-Embedded Tissue," 30$^{th}$ Annual San Antonio Breast Cancer Symposium, Dec. 13-16, 2007; San Antonio, TX, USA (Poster).

Biernat, W. et al., "Quantitative HER2 levels and steroid receptor expression in primary breast cancers and in matched brain metastases," 2012 J. Clin. Oncol. 30 (Jun. 20 Suppl.): Abstract 603.

Biernat, W. et al., "Quantitative HER2 levels and steroid receptor expression in primary breast cancers and in matched brain metastases," American Society of Clinical Oncology (ASCO) Annual Meeting, May 31-Jun. 4, 2012; Chicago, IL (Poster 603).

Huang, W. et al., "Quantitative HER2 measurement and PI3K mutation profile in matched primary and metastatic breast cancer tissues," 2012 J. Clin. Oncol. 30 (Jun. 20 Suppl.): Abstract 614.

Huang, W. et al., "Quantitative HER2 measurement and PI3K mutation profile in matched primary and metastatic breast cancer tissues," American Society of Clinical Oncology (ASCO) Annual Meeting, May 31-Jun. 4, 2012, Chicago, IL (Poster 614).

Sperinde, J. et al., "A comparative study of p95-HER2 carboxy terminal fragment (CTF) detected by immunohistochemistry and VeraTag immunoassays in human breast tumors," In: Proc. Am. Assoc. Cancer Res., Mar. 31, 2012-Apr. 4, 2012, Chicago, IL. Philadelphia (PA): AACR; Cancer Res. 2012, 72(8 Suppl): Abstract 687.

Sperinde, J. et al., "A comparative study of p95-HER2 carboxy terminal fragment (CTF) detected by immunohistochemistry and VeraTag immunoassays in human breast tumors," American Association for Cancer Research (AACR) Annual Meeting, Mar. 31-Apr. 4, 2012, Chicago, IL (Poster 687).

Villasboas, J.C. et al., "Correlation of quantitative p95HER2, HER3, and HER2 protein expression with pathologic complete response (pCR) in HER2-positive breast cancer patients treated with neoadjuvant (NEO) trastuzumab containing therapy," 2012 J. Clin. Oncol. 30 (Jun. 20 Suppl.): Abstract 608.

Villasboas, J.C. et al., "Correlation of quantitative p95HER2, HER3, and HER2 protein expression with pathologic complete response (pCR) in HER2-positive breast cancer patients treated with neoadjuvant

(56) References Cited

OTHER PUBLICATIONS (NEO) trastuzumab containing therapy," American Society of Clinical Oncology (ASCO) Annual Meeting, May 31-Jun. 4, 2012, Chicago, IL (Poster 608).
Biernat, W. et al., "Quantitative measurements of p95HER2 (p95) and total HER2 (H2T) protein expression in patients with trastuzumab-treated, metastatic breast cancer (MBC): Independent confirmation of clinical cutoffs," 2011 J. Clin. Oncol. 29(15)(May 20 Suppl.): Abstract 586.
Biernat, W. et al., "Quantitative measurements of p95HER2 (p95) and total HER2 (H2T) protein expression in patients with trastuzumab-treated, metastatic breast cancer (MBC): Independent confirmation of clinical cutoffs," American Society of Clinical Oncology (ASCO) Annual Meeting, Jun. 3-7, 2011, Chicago, IL (Poster 586).
Cook, J.W. et al., "Mutations in the catalytic domain of PI3 kinase and correlation with clinical outcome in trastuzumab-treated metastatic breast cancer (MBC)," 2011 J. Clin. Oncol. 29(15)(May 20 Suppl.): Abstract 582.
Cook, J.W. et al., "Mutations in the catalytic domain of PI3 kinase and correlation with clinical outcome in trastuzumab-treated metastatic breast cancer (MBC)," American Society of Clinical Oncology (ASCO) Annual Meeting, Jun. 3-7, 2011, Chicago, IL (Poster 582).
Duchnowska, R. et al., "Correlation between Quantitative HER2 Protein Expression and Risk of Brain Metastases in HER2-Positive Advanced Breast Cancer Patients Receiving Trastuzumab-Containing Therapy," Cancer Research, Dec. 15, 2011, 71(24 Suppl. 3):291s (Abstract P2-12-05).
Duchnowska, R. et al., "Correlation between Quantitative HER2 Protein Expression and Risk of Brain Metastases in HER2-Positive Advanced Breast Cancer Patients Receiving Trastuzumab-Containing Therapy," Annual San Antonio Breast Cancer Symposium, Dec. 6-10, 2011, San Antonio, TX, USA (Poster P2-12-05).
Huang, W. et al., "Comparison of four HER2 testing methods in detection of HER2-positive breast cancer: results in the FinHer study cohort," Cancer Research, Dec. 15, 2011, 71(24)(Suppl. 3):187s-188s (Abstract P1-07-01).
Huang, W. et al., "Comparison of four HER2 testing methods in detection of HER2-positive breast cancer: results in the FinHer study cohort," Annual San Antonio Breast Cancer Symposium, Dec. 6-10, 2011, San Antonio, TX, USA (Poster P1-07-01).
Huang, W. et al., "Assessment of real-world HER2 status by immunohistochemistry (IHC) and fluorescence in situ hybridization (FISH) in breast cancers: Comparison with HERMark®, a validated quantitative measure of HER2 protein expression," Cancer Research, Dec. 15, 2011, 71(24)(Suppl. 3):192s-193s (Abstract P1-07-12).
Huang, W. et al., "Assessment of real-world HER2 status by immunohistochemistry (IHC) and fluorescence in situ hybridization (FISH) in breast cancers: Comparison with HERMark®, a validated quantitative measure of HER2 protein expression," Annual San Antonio Breast Cancer Symposium, Dec. 6-10, 2011, San Antonio, TX, USA (Poster P1-07-12).
Shi, Y. et al., "Quantitative measurement of HER3-PI3K complex and total p85α subunit in formalin-fixed, paraffin-embedded (FFPE) tissues using VeraTag™ immunoassays," American Association for Cancer Research Special Conference: Targeting PI3K/mTOR Signaling in Cancer, Feb. 24-27, 2011, San Francisco, CA: Poster.
Wallweber, J. et al., "Subclassification of squamous cell carcinomas of the head and neck based on HER/ErbB and c-MET receptor protein expression and activation profiles," In: Proc. Am. Assoc. Cancer Res. AACR, Apr. 2-6, 2011, Orlando, FL: Abstract LB-323.
Wallweber, J. et al., "Subclassification of squamous cell carcinomas of the head and neck based on HER/ErbB and c-MET receptor protein expression and activation profiles," American Association for Cancer Research (AACR) Annual Meeting, Apr. 2-6, 2011, Orlando, FL (Poster LB-323).
Duchnowska, R. et al., "Correlation between quantitative HER2 Protein level and the risk of brain metastases (BM) in patients (ots) with metastatic breast cancer (MBC) treated with trastuzumab-containing therapy," 2010 J. Clin. Oncol. 28(15s) (Jun. 20 Suppl.): Abstract 1030.
Duchnowska, R. et al., "Correlation between quantitative HER2 Protein level and the risk of brain metastases (BM) in patients (ots) with metastatic breast cancer (MBC) treated with trastuzumab-containing therapy," American Society of Clinical Oncology (ASCO) Annual Meeting, Jun. 4-8, 2010, Chicago, IL (Poster 1030).
Wallweber, J., "Quantitative assessment of HER/erbB receptor protein expression and activation status in FFPE tumor samples identifies an activated HER1 signature in squamous cell carcinomas of the head and neck," In: Proc. Am. Assoc. Cancer Res. AACR, Apr. 17-21, 2010, Washington, D.C.: Abstract LB-66.
Wallweber, J., "Quantitative assessment of HER/erbB receptor protein expression and activation status in FFPE tumor samples identifies an activated HER1 signature in squamous cell carcinomas of the head and neck," American Association for Cancer Research (AACR) Annual Meeting, Apr. 17-21, 2010, Washington, D.C. (Poster LB-66).
Bates, M. et al., "Relationship between Quantitative HER2 Protein Expression and Clinical Outcomes in ER-Positive and ER-Negative Sub-Groups of Patients with Trastuzumab," Dec. 15, 2009, Cancer Research 69(24)(Suppl. 1): Abstract 5136.
Bates, M. et al., "Relationship between Quantitative HER2 Protein Expression and Clinical Outcomes in ER-Positive and ER-Negative Sub-Groups of Patients with Trastuzumab," $32^{nd}$ Annual San Antonio Breast Cancer Symposium, Dec. 9-13, 2009, San Antonio, TX, USA (Poster 5136).
Eli, L. et al., "Quantitative measurements of phosphorylated HER1, HER2, and HER1-HER2 heterodimers in formalin-fixed, paraffin-embedded (FFPE) breast and head/neck tumors using proximity-based immunoassays," In: Proc. Am. Assoc. Cancer Res. AACR, Apr. 18-22, 2009, Denver, CO: Abstract 5247.
Eli, L. et al., "Quantitative measurements of phosphorylated HER1, HER2, and HER1-HER2 heterodimers in formalin-fixed, paraffin-embedded (FFPE) breast and head/neck tumors using proximity-based immunoassays," American Association of Cancer Research (AACR) Annual Meeting, Apr. 18-22, 2009, Denver, CO (Poster 5247).
Joensuu, H. et al. "Breast cancer patients with very high tumor HER2 expression levels might not benefit from treatment with trastuzumab plus chemotherapy: A retrospective exploratory analysis of the FinHer trial," Dec. 15, 2009, Cancer Research 69(24)(Suppl. 1): Abstract 5083.
Joensuu, H. et al. "Breast cancer patients with very high tumor HER2 expression levels might not benefit from treatment with trastuzumab plus chemotherapy: A retrospective exploratory analysis of the FinHer trial," $32^{nd}$ Annual San Antonio Breast Cancer Symposium, Dec. 10-13, 2009, San Antonio, TX, USA.
Williams, S. et al., "Profiling PI3K-Akt pathway activation in formalin fixed, paraffin-embedded cell line models and breast and ovarian tumors using a novel proximity assay," In: Proc. Am. Assoc. Cancer Res. AACR, Apr. 18-22, 2009, Denver, CO: Abstract 5251.
Williams, S. et al., "Profiling PI3K-Akt pathway activation in formalin fixed, paraffin-embedded cell line models and breast and ovarian tumors using a novel proximity assay," American Association of Cancer Research (AACR) Annual Meeting, Apr. 18-22, 2009, Denver, CO (Poster 5251).
Lipton, A. et al., "Multiple Subtypes of HER-2/Neu-Positive Metastatic Breast Cancer," Cancer Research, Dec. 15, 2009, 69(24 Suppl. 1): Abstract 2030.
Lipton, A. et al., "Multiple Subtypes of HER-2/Neu-Positive Metastatic Breast Cancer," $32^{nd}$ Annual San Antonio Breast Cancer Symposium, Dec. 9-13, 2009, San Antonio, TX, USA (Poster 2030).
Shi, Y. et al., "Quantitative, sensitive, and reproducible measurement of epidermal growth factor receptor/HER1 homodimerization and total expression in formalin-fixed, paraffin-embedded tumors using a novel proximity-based assay," In: Proc. Am. Assoc. Cancer Res. AACR, Apr. 18-22, 2009, Denver, CO: Abstract 5244.
Shi, Y. et al., "Quantitative, sensitive, and reproducible measurement of epidermal growth factor receptor/HER1 homodimerization and total expression in formalin-fixed, paraffin-embedded tumors

(56) References Cited

OTHER PUBLICATIONS using a novel proximity-based assay," American Association of Cancer Research (AACR) Annual Meeting, Apr. 18-22, 2009 Denver, CO (Poster 5244).

Leitzel, A. et al., "Discordant HER2 Total and HER2 Homodimer Levels by HERmark Analysis in Matched Primary and Metastatic Breast Cancer FFPE Specimens," Cancer Research, Dec. 15, 2009, 69(24 Suppl. 1): Abstract 2131.

Leitzel, A. et al., "Discordant HER2 Total and HER2 Homodimer Levels by HERmark Analysis in Matched Primary and Metastatic Breast Cancer FFPE Specimens," $32^{nd}$ Annual San Antonio Breast Cancer Symposium, Dec. 9-13, 2009, San Antonio, TX, USA (Poster 2132).

Badal, M.Y. et al., "Measurement of the HER3-PI3K complex as a marker of PI3K-Akt pathway activation in formalin fixed, paraffin-embedded cell line models and breast and ovarian tumors using a novel proximity assay," American Association for Cancer Research (AACR) Special Conference on Targeting the PI3K-Kinase Pathway in Cancer, Nov. 11-14, 2008, Cambridge, MA, USA (Poster).

Bates, M., et al., "Quantitative HER2 homodimer levels correlate with time to first recurrence in HER2-positive breast cancer patients who did not receive trastuzumab in the adjuvant setting," Cancer Res. Jan. 15, 2009, 69(2 Suppl. 1): Abstract 1074.

Bates, M. et al., "Quantitative HER2 homodimer levels correlate with time to first recurrence in HER2-positive breast cancer patients who did not receive trastuzumab in the adjuvant setting," $31^{st}$ Annual San Antonio Breast Cancer Symposium, Dec. 10-14, 2008, San Antonio, TX, USA (Poster 1074).

Eli, L. et al., "Development of novel-proximity-based immunoassays for activated HER1, HER2, HER1-HER2 heterodimers in formalin-fixed, paraffin-embedded (FFPE) cells," 2008 Eur. J. Cancer 6(Oct. 12):30 (Abstract 88).

Eli, L. et al., "Development of novel-proximity-based immunoassays for activated HER1, HER2, HER1-HER2 heterodimers in formalin-fixed, paraffin-embedded (FFPE) cells," International Conference on Molecular Targets and Cancer Therapeutics, AACR-NCI-EORTC, Oct. 21-24, 2008, Geneva, Switzerland (Poster 88).

Huang, W. et al., "Comparison of Central HER-2 Tests With Quantitative HER-2 Expression and HER-2 Homodimer Measurements Using a Novel Proximity Based Assay," 2008 Arch. Pathol. Lab. Med. 132 (Sep.):1476 (CAP Abstract 40).

Huang, W. et al., "Comparison of Central HER-2 Tests With Quantitative HER-2 Expression and HER-2 Homodimer Measurements Using a Novel Proximity Based Assay," American College of Pathologist (CAP) Annual Meeting, Sep. 25-28, 2008 (Poster 40).

Joensuu, H. et al., "Quantitative measurement of HER2 expression and HER2 homodimer using a novel proximity based assay: comparison with HER2 status by immunohistochemistry and chromogenic in situ hybridization in the FinHer study," Cancer Research, Jan. 15, 2009, 69(2 Suppl. 1): Abstract 2071.

Joensuu, H. et al., "Quantitative measurement of HER2 expression and HER2 homodimer using a novel proximity based assay: comparison with HER2 status by immunohistochemistry and chromogenic in situ hybridization in the FinHer study," $31^{st}$ Annual San Antonio Breast Cancer Symposium, Dec. 10-14, 2008, San Antonio, TX, USA (Poster 2071).

Lipton, A. et al., "HER2 protein expression predicts response to trastuzumab in FISH-positive patients," Cancer Research, Jan. 15, 2009, 69(2 Suppl. 1): Abstract 32.

Lipton, A. et al., "HER2 protein expression predicts response to trastuzumab in FISH-positive patients," $31^{st}$ Annual San Antonio Breast Cancer Symposium, Dec. 10-14, 2008, San Antonio, TX, USA (Poster 32).

Leitzel K., et al., "Use of total HER2 and HER2 homodimer levels to predict response to trastuzumab," J. Clin. Oncol. 2008 (May 20 Suppl.): Abstract 1002.

Leitzel, K. et al., "Total HER2 and HER2 homodimer levels predict response to trastuzumab," American Society of Clinical Oncology (ASCO) Annual Meeting, May 30-Jun. 3, 2008, Chicago, IL (Oral Presentation 1002).

Mukherjee, A. et al., "Proximity-based assays for the detection of activated HER3, HER2/3 heterodimers and HER3/PI3K complexes in FFPE cell line controls and tumors," Cancer Research, Jan. 15, 2009, 69(2 Suppl. 1): Abstract 4040.

Mukherjee, A. et al., "Proximity-based assays for the detection of activated HER3, HER2/3 heterodimers and HER3/PI3K complexes in FFPE cell line controls and tumors," $31^{st}$ Annual San Antonio Breast Cancer Symposium, Dec. 10-14, 2008, San Antonio, TX, USA (Poster 4040).

Shi, Y. et al., "Development of highly quantitative, sensitive, and reproducible assays for the detection of EGFR/HER1 and ErbB3/HER3 in in formalin-fixed, paraffin-embedded cells," 2008 Eur. J. Cancer 6(Oct. 12):34-35 (Abstract 103).

Shi, Y. et al., "Development of highly quantitative, sensitive, and reproducible assays for the detection of EGFR/HER1 and ErbB3/HER3 in in formalin-fixed, paraffin-embedded cells," International Conference on Molecular Targets and Cancer Therapeutics, AACR-NCI-EORTC, Oct. 21-24, 2008, Geneva, Switzerland, Poster 103.

Bates, M. et al., "HER2 Expression and HER2:HER2 Dimerization Identifies Subpopulations of Metastatic Breast Cancer Patients With Different Probabilities of Long-Term Survival Following Trastuzumab Treatment and With Different Requirements for Concomitant Chemotherapy," American Society of Clinical Oncology (ASCO) Annual Meeting, Jun. 2-5, 2007, Chicago, IL (Poster 10557).

Dua, R. et al., "Profiling HER-Family Receptor Dimerization in HER2 Overexpressing Cells that Coexpress Mutated EGFR Receptors," Breast Cancer Research and Treatment, Dec. 13, 2007, 106(1 Suppl.):S203 (Abstract 4108).

Dua, R. et al., "Profiling HER-Family Receptor Dimerization in HER2 Overexpressing Cells that Coexpress Mutated EGFR Receptors," $30^{th}$ Annual San Antonio Breast Cancer Symposium, Dec. 13-16, 2007, San Antonio, TX, USA (Poster 4108).

Dua, R. et al., "Patterns of HER-Family Receptor Dimerization Intrastuzumab Susceptible and Trastuzumab Resistant Cell Lines," 2007 J. Clin. Oncol. 25(18S) (Jun. 20 Suppl.): Abstract 2533.

Dua, R. et al., "Patterns of HER-Family Receptor Dimerization Intrastuzumab Susceptible and Trastuzumab Resistant Cell Lines," American Society of Clinical Oncology (ASCO) Annual Meeting, Jun. 2-5, 2007, Chicago, IL, USA (Poster 2533).

Huang, W. et al., "Quantitative Measurements of HER2 Expression and HER2: HER2 Dimerization Identify Subgroups of HER2 Positive Metastatic Breast Cancer Patients with Different Probabilities of Response to Trastuzumab Treatment," Breast Cancer Research and Treatment, Dec. 13, 2007, 106(1 Suppl.):S86 (Abstract 2007).

Huang, W. et al., "Quantitative Measurements of HER2 Expression and HER2: HER2 Dimerization Identify Subgroups of HER2 Positive Metastatic Breast Cancer Patients with Different Probabilities of Response to Trastuzumab Treatment," $30^{th}$ Annual San Antonio Breast Cancer Symposium, Dec. 13-16, 2007, San Antonio, TX, USA (Poster 2007).

Toi, M. et al., "Differential Survival Following Trastuzumab Treatment Based on Quantitative HER2 Expression and HER2 Dimerization in a Clinic-Based Cohort of Patients With Metastatic Breast Cancer," 2007 J. Clin. Oncol. 25(18S) (Jun. 20 Suppl.): Abstract 1025.

Toi, M. et al., "Differential Survival following Trastuzumab Treatment based on Quantitative HER2 Expression and HER2:HER2 Dimerization in a Clinic-Based Cohort of Patients with Metastatic Breast Cancer," American Society of Clinical Oncology (ASCO) Annual Meeting, Jun. 2-5, 2007, Chicago, IL (Poster 1025).

Wallweber, J. et al., "Increased Detection of Breast Cancer Markers Human Epidermal Growth Factor Receptor Dimer and Downstream Signaling Proteins Utilizing the VeraTag Technology with Dextran Modified Antibodies," Breast Cancer Research and Treatment, Dec. 13, 2007, 106(1 Suppl.):S207 (Abstract 5002).

Wallweber, J. et al., "Increased Detection of Breast Cancer Markers Human Epidermal Growth Factor Receptor Dimer and Downstream Signaling Proteins Utilizing the VeraTag Technology with Dextran Modified Antibodies," $30^{th}$ Annual San Antonio Breast Cancer Symposium, Dec. 13-16, 2007, San Antonio, TX, USA (Poster 5002).

Winslow, J. et al., "Characterization of a Novel Proximity Immunoassay for the Quantitative Determination of HER2 Protein Expression

(56) References Cited

OTHER PUBLICATIONS and HER2 Homodimerization in Formalin-Fixed, Paraffin-Embedded Breast Cancer Tissue," Breast Cancer Research and Treatment, Dec. 13, 2007, 106(1 Suppl.):S88 (Abstract 2012).
Winslow, J. et al., "Characterization of a Novel Proximity Immunoassay for the Quantitative Determination of HER2 Protein Expression and HER2 Homodimerization in Formalin-Fixed, Paraffin-Embedded Breast Cancer Tissue," 30th Annual San Antonio Breast Cancer Symposium, Dec. 13-16, 2007, San Antonio, TX, USA (Poster 2012).
Hameed, M.R. et al., "The ERB family receptor dimerization in glioblastoma—An eTag assay analysis of 23 cases," 2006 J. Clin. Oncol. 24(18S) (Jun. 20 Suppl.): Abstract 1582.
Hameed, M.R. et al., "The ERB family receptor dimerization in glioblastoma—An eTag assay analysis of 23 cases," American Society of Cancer Oncology (ASCO) Annual Meeting, Jun. 2-6, 2006, Atlanta, GA (Poster 1582).
Jimeno, A. et al., "Combined targeted therapy shows increased efficacy in a novel in vivo pancreas cancer model," American Association for Cancer Research (AACR) Annual Meeting, Apr. 1-6, 2006, Washington, D.C. (Abstract 2181).
Dua, R. et al., "ErbB/HER pathway profiling in formalin-fixed paraffin embedded preclinical xenograft models using multiplexed proximity-based assays," International Conference on Molecular Targets and Cancer Therapeutics, AACR-NCI-EORTC, Nov. 14-18, 2005, Philadelphia, PA: Abstract A121.
Dua, R. et al., "ErbB/HER pathway profiling in formalin-fixed paraffin embedded preclinical xenograft models using multiplexed proximity-based assays," International Conference on Molecular Targets and Cancer Therapeutics, AACR-NCI-EORTC, Nov. 14-18, 2005, Philadelphia, PA (Poster A121).
Shi, Y., "Analysis of ErbB/HER receptor pathways in formalin-fixed and paraffin-embedded cancer cell lines using multiplexed eTag™ assays," 2005 J. Clin. Oncol. 23(16S) (Jun. 1 Suppl.): Abstract 9565.
Shi, Y. et al., "Analysis of ErbB/HER receptor pathways in formalin-fixed and paraffin-embedded cancer cell lines using multiplexed eTag™ assays," American Society of Clinical Oncology (ASCO) Annual Meeting, May 13-17, 2007, Orlando, FL (Poster 9565).
Mukherjee, A. et al., "Correlation of ErbB activation status and clinical response in Herceptin treated breast cancer patients," 2005, Proc. Amer. Canc. Res., 46 (Apr. 16): Abstract 3688.
Mukherjee, A. et al., "Correlation of ErbB activation status and clinical response in Herceptin treated breast cancer patients," American Association for Cancer Research (AACR) Annual Meeting, Apr. 16-20, 2005, Anaheim/Orange County, CA, USA (Poster 3688).
Mukherjee, A., "The Use of ErbB/HER Activation Status as Prognostic Markers in Breast Cancer Patients Treated with Trastuzumab," 2005 J. Clin. Oncol. 23(16S) (Jun. 1 Suppl.): Abstract 553.
Mukherjee, A. et al., "The use of ErbB activation Status as Prognostic Markers in Breast Cancer Patients Treated with Trastuzumab," American Society of Clinical Oncology (ASCO) Annual Meeting, May 13-17, 2005, Orlando, FL (Poster 553).
Salimi-Moosavi, H. et al., "Effect of Erbitux, Erlotinib, Gefitinib, and Rapamycin on the inhibition of EGFR dimer formation and downstream signaling pathways in different cancer cell lines," International Conference on Molecular Targets and Cancer Therapeutics, AACR-NCI-EORTC, Nov. 14-18, 2005, Philadelphia, PA: Abstract A127.
Salimi-Moosavi, H. et al., "Effect of Erbitux, Erlotinib, Gefitinib, and Rapamycin on the inhibition of EGFR dimer formation and downstream signaling pathways in different cancer cell lines," International Conference on Molecular Targets and Cancer Therapeutics, AACR-NCI-EORTC, Nov. 14-18, 2005, Philadelphia, PA (Poster A127).
Salimi-Moosavi, H. et al., "Effect of gefitinib on EGFR activation in lung cancer cell lines," Intl. Conference on Molecular Targets and Cancer Therapeutics, AACR-NCI-EORTC, Nov. 14-18, 2005, Philadelphia, PA: Abstract A124.
Salimi-Moosavi, H. et al., "Effect of gefitinib on EGFR activation in lung cancer cell lines," Intl. Conference on Molecular Targets and Cancer Therapeutics, AACR-NCI-EORTC, Nov. 14-18, 2005, Philadelphia, PA (Poster A124).
Salimi-Moosavi, H. et al., "IC50 determination for receptor-targeted compounds and downstream signaling," In: Proc. Am. Assoc. Cancer Res. AACR, Apr. 16-20, 2005, Anaheim, CA: Abstract 4567.
Shi, Y. et al., "Multiplexed assay for assessing ErbB/HER receptor pathways in formalin-fixed and paraffin-embedded cancer cell lines," In: Proc. Am. Assoc. Cancer Res. AACR Apr. 16-20, 2005 Anaheim, CA: Abstract 5762.
Shi, Y. et al., "Multiplexed assay for assessing ErbB/HER receptor pathways in formalin-fixed and paraffin-embedded cancer cell lines," American Association for Cancer Research (AACR) Annual Meeting, Apr. 16-20, 2005, Anaheim, CA (Poster 5762).
Sperinde, J. et al., "Multiplex detection of vascular endothelial growth factor receptor 2 (VEGFR2) homodimers and phosphorylation in xenografts, human tumor tissues and formalin-fixed paraffin-embedded (FFPE) samples from cell lines using the eTag™ assay system," International Conference on Molecular Targets and Cancer Therapeutics, Nov. 14-18, 2005, Philadelphia, PA: Abstract B17.
Sperinde, J. et al., "Multiplex detection of vascular endothelial growth factor receptor 2 (VEGFR2) homodimers and phosphorylation in xenografts, human tumor tissues and formalin-fixed paraffin-embedded (FFPE) samples from cell lines using the eTag™ assay system," International Conference on Molecular Targets and Cancer Therapeutics, Nov. 14-18, 2005, Philadelphia, PA (Poster B17).
Toi, M. et al., "The Correlation of ErbB/HER Activation Status with Breast Cancer Patient Response to Trastuzumab," National Cancer Research Cancer Institute (NCRI) Conference, Oct. 2-5, 2005, Birmingham, UK (Poster 1025).
Yatabe, Y et al., "Application of Proximity Based Assay to Develop Algorithms That Correlate ErbB/HER Pathway Profiling and Predictive Response to EGFR/HER1 Targeted Therapy in Lung Cancer Patients," Intl. Conference on Molecular Targets and Cancer Therapeutics, Nov. 14-18, 2005, Philadelphia, PA: Abstract A123.
Yatabe, Y et al., "Application of Proximity Based Assay to Develop Algorithms That Correlate ErbB/HER Pathway Profiling and Predictive Response to EGFR/HER1 Targeted Therapy in Lung Cancer Patients," Intl. Conference on Molecular Targets and Cancer Therapeutics, Nov. 14-18, 2005, Philadelphia, PA (Poster A123).
Duchnowska, R. et al., "Correlation between quantitative HER2 protein expression and risk of brain metastasis in HER2-positive advanced breast cancer patients receiving trastuzumab-containing therapy," Oncologist 17(1):26-35 (2012) (pub. online Jan. 10, 2012).
Han, S-W, "Correlation of HER2, p95HER2 and HER3 expression and treatment outcome of lapatinib plus capecitabine in HER2-positive metastatic breast cancer," PLoS ONE 7(7):e39943 (2012) (pub. online Jul. 27, 2012).
Bates, M. et al., "Identification of a Subpopulation of Metastatic Breast Cancer Patients with Very High HER2 Expression Levels and Possible resistance to Trastuzumab," Ann. Oncol., 22(9):2014-2020 (2011) (pub. online Feb. 11, 2011).
Defazio-Eli, L. et al., "Quantitative assays for the measurement of HER1-HER2 heterodimerization and phosphorylation in cell lines and breast tumors: applications for diagnostics and targeted drug mechanism of action," Breast Canc. Res. 13:R44 (2011) (pub. Apr. 15, 2011).
Dua, R. et al., "Detetion of hepatocyte growth factor (HGF) ligand-C-met receptor activation in formalin-fixed, paraffin-embedded specimens by a novel proximity assay," PLOS One 6(1): e15932 (2011) (pub. online Jan. 21, 2011).
Joensuu, H. et al., "Very high quantitative tumor HER2 content and outcome in early breast cancer," Ann. Oncol. 22(9): 2007-2013 (2011) (pub. online Feb. 1, 2011).
Ghosh, M. et al., "Trastuzumab has preferential activity against breast cancers driven by HER2 homodimers," Cancer Res. 71(5):1871 (2011) (pub. online Feb. 15, 2011).
Mukherjee, A. et al., "Profiling the HER3/PI3K Pathway in Breast Tumors Using Proximity-Directed Assays Identifies Correlations between Protein Complexes and Phosphoproteins," PLoS One 6(1): e16443 (2011) (pub. online Jan. 28, 2011).

(56) References Cited

OTHER PUBLICATIONS

Dua, R. et al., "EGFR over-expression and activation in high HER2, ER negative breast cancer cell lines induces trastuzumab resistance," Breast Cancer Res. Treat. 122(3):6850697 (2010) (pub. online Oct. 27, 2009).
Jain, A. et al., "HER kinase axis receptor dimer partner switching occurs in response to EGFR tyrosine kinase inhibition despite failure to block cellular proliferation," Cancer Res. 70(5):1989-1999 (2010) (pub. online Feb. 16, 2010).
Huang, Q. et al., "Comparison of central HER2 testing with quantitative total HER2 expression and HER2 homodimer measurement using a novel proximity based assay," Am. J. Clin. Pathol. 134:303-311 (2010) (pub. Aug. 2010).
Larson, J.S. et al., "Analystical validation of a highly senstivie, accurate, and reproducible assay (HERmark®) for the measurement of HER2 total protein and HER2 homodimers in FFPE breast cancer tumor specimens," Pathol. Res. Intl, 2010: Article ID 814176 (2010) (pub. online Jun. 28, 2010).
Lipton, A. et al., "Quantitative HER2 protein levels predict outcome in fluorescence in situ hybridization-positive patients with metastatic breast cancer treated with trastuzumab," Cancer 116:5168-5178 (2010) (pub. online Nov. 3, 2010).
Mamluk, R. et al., "Anti-tumor effect of CT-322 as an adnectin inhibitor of vascular endothelial growth factor receptor-2," MAbs 2(2):199-208 (2010) (pub. online Mar. 1, 2010).
Sperinde, J. et al., "Quantitation of p95HER2 in paraffin sections by using a p95-specific antibody and correlation with outcome in a cohort of trastuzumab-treated breast cancer patients," Clin. Canc. Res. 16(16):4226-4235 (2010) (pub. online Jul. 27, 2010).
Toi, M. et al., "Differential survival following trastuzumab treatment based on quantitative HER2 expression and HER2 homodimers in a clinic-based cohort of patients with metastatic breast cancer," BMC Cancer 10:56 (2010) (pub. Feb. 23, 2010) (10 pages).
Desmedt, C. et al., "Quantitation of HER2 expression or HER2:HER2 dimers and differential survival in a cohort of metastatic breast cancer patients carefully selected for trastuzumab treatment primarily by FISH," Diagn. Mol. Pathol. 18(1):22-29 (2009) (pub. Mar. 2009).
Shi, Y. et al., "A novel proximity assay for the detection of proteins and protein complexes: quantitation of HER1 and HER2 total protein expression and homodimerization in formalin-fixed, paraffin-embedded cell lines and breast cancer tissue," Diagn. Mol. Pathol. 18(1):11-21 (2009) (pub. Mar. 2009).
Chan-Hui, P-Y et al., "Applications of eTag™ assay platform to systems biology approaches in molecular oncology and toxicology studies," Clin. Immun. 111:162-174 (2004) (pub. online Mar. 11, 2004).
Tian, H. et al., "Multiplex mRNA assay using electrophoretic tags for high-throughput gene expression analysis," Nucl. Acid Res. 32(16):e126 (pub. online Sep. 8, 2004).
Arribas, J. et al., "HER2 Fragmentation and Breast Cancer Stratification," 2010, Clin. Cancer Res., 16(16):4071-4073.
Arribas, J. et al., "p97HER2 and Breast Cancer," 2011, Cancer Res., 71(5):1-5.
Amler, L. et al, "Downregulation of HER3 may predict clinical benefit in ovarian cancer from pertuzumab, a HER2 dimerization-inhibiting antibody," 2008 Molecular Markers Meeting, Amer. Soc. Clin. Onc., Abstract 25.
Arkin, M. and Moasser, M., "HER-2-directed, small-molecule antagonists," Curr. Opin. Investig. Drugs 9(12):1264-1276 (2008).
Bacus, S. et al., "The expression of HER B receptors and their ligands as predicting factors for response to chemotherapy," European J. Cancer 36(5):Abstract S103 (2000).
Baselga, J. et al., "Phase II Study of Weekly Intravenous Recombinant Humanized Anti-p185$^{HER2}$ Monoclonal Antibody in Patients With HER2/neu-Overexpressing Metastatic Breast Cancer," J. Clin. Oncol. 14(3):737-744 (1996).
Baselga, J., "Herceptin® Alone or in Combination with Chemotherapy in the Treatment of HER2-Positive Metastatic Breast Cancer: Pivotal Trials," Oncology 61(supp 2):14-21 (2001).

Basic Methods in Antibody Production and Characterization, Howard, G. and Bethel, D., eds., CRC Press (2001).
Bianco, R. et al., "Rational bases for the development of EGFR inhibitors for cancer treatment," Intl. J. Biochem. Cell Biol. 39:1416-1431 (2007).
Bioconjugate Techniques, Hermanson, G. ed., Academic Press, NY (1996).
Britten, C.D., "Targeting ErbB receptor signaling: A pan-ErbB approach to cancer," Molec. Canc. Ther. 3(10):1335-1342 (2004).
Buck, E. et al., "Inactivation of Akt by the epidermal growth factor receptor inhibitor erlotinib is mediated by HER-3 in pancreatic and colorectal tumor cell lines and contributes to erlotinib sensitivity," Mol. Cancer Ther. 5(8):2051-2059 (2006).
Burgess, A. et al., "An Open-and-Shut Case? Recent Insights into the Activation of EGF/ErbB Receptors," Mol. Cell 12:541-552 (2003).
Burgess, A., "EGFR family: Structure physiology signaling and therapeutic targets," Growth Factors 26(5):263-274 (2008).
Buzdar, A. et al., "Significantly Higher Pathologic Complete Remission Rate After Neoadjuvant Therapy With Trastuzumab, Paclitaxel, and Epirubicin Chemotherapy: Results of a Randomized Trial in Human Epidermal Growth Factor Receptor 2-Positive Operable Breast Cancer," J. Clin. Oncol. 23:3676-3685 (2005).
Cappuzzo, F. et al., "HER3 genomic gain and sensitivity to gefitinib in advanced non-small-cell lung cancer patients," Brit. J. Cancer 93:1334-1340 (2005).
Carden, C.P. et al., "From Darkness to Light With Biomarkers in Early Clinical Trials of Cancer Drugs," Clin. Pharmacol. Ther. 85(2):131-133 (2009).
Christianson, T. et al., "NH2-terminally Truncated HER 2/neu Protein: Relationship with Shedding of the Extracellular Domain and with Prognostic Factors in Breast Cancer," Cancer Res. 58:5123-5129 (1998).
Citri, A. et al., "The deaf and the dumb: the biology of ErbB-2 and ErbB-3," Experimental Cell Res. 284:54-65 (2003).
Cobleigh, M. et al., "Multinational Study of the Efficacy and Safety of Humanized Anti-HER2 Monoclonal Antibody in Women Who Have HER2-Overexpressing Metastatic Breast Cancer That Has Progressed After Chemotherapy for Metastatic Disease," J. Clin. Oncol. 17(9):2639-2648 (1999).
Column Handbook for Size Exclusion Chromatography, Wu, C. ed., Academic Press, San Diego, CA (1999).
De Alva, E. et al., "Neuregulin Expression Modulates Clinical Response to Trastuzumab in Patients With Metastatic Breast Cancer," J. Clin. Oncol. 25:2656-2663 (2007).
Dhani, N. And Siu, L., "Clinical trials and biomarker development with molecularly targeted agents and radiotherapy," Cancer Metastasis Rev. 27:339-349 (2008).
Fountzilas, G. et al., "Weekly paclitaxel as first-line chemotherapy and trastuzumab in patients with advanced breast cancer," Ann. Oncol. 12:1545-1551 (2001).
Frolov, A. et al., "ErbB3 Expression and Dimerization with EGFR Influence Pancreatic Cancer Cell Sensitivity to Erlotinib," Cancer Biol. Ther. 6(4):e1-e7 (2007).
Fuchs, B. et al., "Epithelial-to-Mesenchymal Transition and Integrin-Linked Kinase mediate Sensitivity to Epidermal Growth Factor Receptor Inhibition in Human Hepatoma Cells," Cancer Res. 68:2391-2399 (2008).
Fuchs, I. et al., "Epidermal Growth Factor Receptor Changes During Breast Cancer Metastasis," Anticancer Res. 26:4397-4402 (2006).
Garcia-Castillo, J., et al., "HER2 Carboxyl-Terminal Fragments Regulate Cell Migration & Cortactin Phosphorylation," J. Biol. Chem. 284(37):25301-25313 (2009).
Hamburger, A., "The Role of ErbB3 and its Binding Partners in Breast Cancer Progression and Resistance to Hormone and Tyrosine Kinase Directed Therapies," J. Mammary Gland Biol. Neoplasia 13:225-233 (2008).
Harries, M. and Smith, I., "The development and clinical use of trastuzumab (Herceptin)," Endocrine-Related Cancer 9:75-85 (2002).
Haughland, R., "Handbook of Fluorescent Probes and Research Products," 9$^{th}$ Ed., Gregory, J. ed., Molecular Probes, Eugene, OR (2002).

(56) References Cited

OTHER PUBLICATIONS

"HER3/ErbB3 (1B2) Rabbit mAb," Apr. 2, 2010, XP055072082, (retrieved on Jul. 19, 2013 from http://www.cellsignal.com/pdf/4754).
High Resolution Chromatography: A Practical Approach, Millner, P. ed., Oxford University Press, NY (1999).
HPLC of macromolecules: a practical approach, Oliver, R. ed., Oxford University Press, Oxford, England (1989).
Jahanzeb, M., "Trastuzumab-Based Combinations in Metastatic Breast Cancer: How to Make a Choice," Clin. Breast Cancer, 4(1):28-38 (2003).
Joensuu, H. et al., "Adjuvant Docetaxel or Vinorelbine with or without Trastuzumab for Breast Cancer," N. Eng. J. Med. 354:809-890 (2006).
Knowlden, J.M. et al., "c-erbB3 and c-erbB4 expression is a feature of the endocrine responsive phenotype in clinical breast cancer," Oncogene 17:1949-1957 (1998).
Kraus, M. et al., "Isolation and characterization of ERBB3, a third member of the ERBB/epidermal growth factor receptor family: Evidence for overexpression in a subset of human mammary tumors," Proc. Natl. Acad. Sci. USA 86:9193-9197 (1989).
Latch, D. and McNeill, K. "Microheterogeneity of Singlet Oxygen Distributions in Irradiated Humic Acid Solutions," Science 311:1743-1747 (2006).
Lee, J. et al., "Biomarker Assay Translation from Discovery to Clinical Studies in Cancer Drug Development: Quantification of Emerging Protein Biomarkers," Advances in Cancer Research 96:269-298 (2007).
Lee-Hoeflich, S. et al., "A Central Role for HER3 in HER2-Amplified Breast Cancer: Implications for Targeted Therapy," Cancer Res. 68(14):5878-5887 (2008).
Ludwig, J. and Weinstein, J., "Biomarkers in Cancer Staging, Prognosis and Treatment Selection," Nature Reviews Cancer 5:845-856 (2005).
Ma, C. and Bose, R., "Current and Future Roles of Lapatinib in HER2-Positive Breast Cancer," E-Updates in HER1 and HER2 Targeting in Breast Cancer vol. 2 (Sep. 1) (2008).
Makhija, S. et al., "HER pathway gene expression analysis in a phase II study of pertuzumab + gemcitabine vs. gemcitabine + placebo in patients with platinum-resistant epithelial ovarian cancer," J. Clin. Oncol. (May 20 Supplement) 26: ASCO Abstract 5552 (2008).
Menendez, J. and Lupu, R., "Transphosphorylation of kinase-dead HER3 and breast cancer progression: a new standpoint or an old concept revisited?" Breast Cancer Res. 9:111 (5 pp.) (2007).
"Mouse (monoclonal) anti-ErbB3/Her3 (C-terminus) Product Analysis Sheet," Nov. 1, 2008, XP055072081 (retrieved on Jul. 19, 2013 from http//userimg.fantibody.com/files/ts/dixfile/2013-05/29/15/feSxnJ4wJXnFFnWz.pdf).
Mukherjee, A., "The use of ErbB/HER activation status as prognostic markers in breast cancer patients treated with trastuzumab," J. Clin. Oncol. 23(16S)(Jun. 1 Suppl.):553 (2005).
Nagy, P. et al., "Lipid rafts and the local density of ErbB proteins influence the biological role of homo- and heteroassociations of ErbB2," Cell Science 115:4251-4262 (2002).
NCBI Accession No. NM_001982.2, *Homo sapiens* v-erb-b2 erythroblastic leukemia viral oncogene homolog 3 (avian) (ERBB3), transcript variant 1, mRNA, Oct. 24, 2010.
NCBI Accession No. P00533 (protein) Epidermal growth factor receptor, Sep. 7, 2010.
NCBI Accession No. P21860 (protein) Receptor tyrosine-protein kinase erbB-3, Aug. 10, 2010.
Ning, L., "Recent advances of dual tyrosine kinases inhibitor lapatinib in breast cancer therapy," J. Intl. Oncol. 34(5):362-365 (2007).
Normanno, N. et al., "Epidermal growth factor receptor (EGFR) signaling in cancer," Gene 366:2-16 (2006).

Ono, M. and Kuwano, M., "Molecular Mechanisms of Epidermal Growth Factor Receptor (EGFR) Activation and Response to Gefitinib and Other EGFR-Targeting Drugs," Clin. Cancer Res. 12(24):7242-7251 (2006).
Osipo, C. et al., "Role for HER2/neu and HER3 in fulvestrant-resistant breast cancer," Intl. J. Oncol. 30:509-520 (2007).
Pedersen, K. et al., "A Naturally Occurring HER2 Carboxy-Terminal Fragment Promotes Mammary Tumor Growth and Metastasis," Mol. Cell. Biol. 29(12):3319-3331 (2009.
Plowman, G. et al., "Molecular cloning and expression of an additional epidermal growth factor receptor-related gene," Proc. Natl. Acad. Sci. USA 87:4905-4909 (1990).
Practical HPLC Method Development, $3^{rd}$ edition, Snyder, L. et al. eds., John Wiley & Sons, NY (1988).
Prigent, S. et al., "Expression of the c-cerb-3 protein in normal human adult and fetal tissues," Oncogene 7(7):1273-1278 (1992).
Rajkumar, T. et al., "Expression of the c-erbB-3 protein in gastrointestinal tract tumours determined by monoclonal antibody RTJI," J. Pathol. 170(3):271-278 (1993).
Reschke, M. et al., "HER3 is a determinant for poor prognosis in melanoma," Clin. Cancer Res. 14(16):5188-5197 (2008).
Schaap, A., et al., "Polymer-Based Sensitizers for Photooxidations. II," J.Amer. Chem. Soc. 97:3741-3745 (1975).
Scaltriti, M. et al., "Expression of p95HER2, a Truncated Form of the HER2 Receptor, and Response to Anti-HER2 Therapies in Breast Cancer," J. Natl. Cancer Inst. 99:628-638 (2007).
Sergina, N. et al., "Escape from HER-family tyrosine kinase inhibitor therapy by the kinase-inactive HER3," Nature 445:437-441 (2007).
Sithanandam, G. and Anderson, L.M., "The ERBB3 receptor in cancer and cancer gene therapy," Cancer Gene Therapy 15"413-448 (2008).
Slamon, D. et al., "Use of Chemotherapy Plus a Monoclonal Antibody Against HER2 for Metastatic Breast Cancer that Overexpresses HER2," N. Engl. J. Med. 344:783-792 (2001).
Stern, D., "ERBB3/HER3 and ERBB2/HER2 Duet in Mammary Development and Breast Cancer," J. Mammary Gland Biol. Neoplasia 13:215-223 (2008).
Tandon, A. et al., "HER-2/neu Oncogene Protein and Prognosis in Breast Cancer," J. Clin. Oncol.7(8):1120-1128 (1989).
Tovey, S. et al., "Low expression of HER2 protein in breast cancer is biologically significant," J. Pathol. 210:358-362 (2006).
Vogel, C. et al., "Efficacy and Safety of Trastuzumab as a Single Agent in First-Line Treatment of HER2-Overexpressing Metastatic Breast Cancer," J. Clin. Oncol. 20:719-726 (2002).
Winslow J. et al., "Characterization of a novel proximity immunoassay for the quantitative determination of HER2 protein expression and HER2 homodimerization in formalin-fixed, paraffin-embedded breast cancer tissue," Breast Cancer Research and Treatment, Dec. 13, 2007, 106(1):588.
Wolff, A. et al., "American Society of Clinical Oncology/College of American Pathologists Buidline Recommendations for Human Epidermal Growth Factor Receptor 2 Testing in Breast Cancer," Arch. Pathol. Lab. Med. 131:18-43 (2007).
Xu, F. et al., "The Outcome of Heregulin-induced Activation of Ovarian Cancer Cells Depends on the Relative Levels of HER-2 and HER-3 Expression," Clin. Cancer Res. 5:3653-3660 (1999).
Yuan, C. et al., "Purification of Her-2 extracellular domain and identification of its cleavage site," Prot. Expr. & Purif. 29:217-222 (2003).
Canada Patent Application No. 2,711,843, Office Action dated Nov. 8, 2013.
Chinese Patent Application No. 201080009543.X, Office Action dated Mar. 13, 2014.
Chinese Patent Application No. 201080009543.X, Office Action dated Jul. 1, 2013.
Chinese Patent Application No. 201080009543.X, Office Action, dated Jun. 24, 2014.
Chinese Patent Application No. 201080009544.4, Office Action dated Sep. 26, 2013.
Chinese Patent Application No. 201080009544.4, Office Action dated Jun. 19, 2014.

(56) References Cited

OTHER PUBLICATIONS

European Patent Application No. 09831007.1, Supplemental Search Report dated Mar. 6, 2013.
European Patent Application No. 09831007.1, Examination Report dated Feb. 17, 2014.
European Patent Application No. 08868829.6, Extended European Search Report dated Apr. 5, 2011.
European Patent Application No. 10732178.8, Examination Report dated Mar. 10, 2014.
European Patent Application No. 10732178.8, Office Action dated Feb. 27, 2013.
European Patent Application No. 10732183.8, Office Action dated Jul. 24, 2013.
European Patent Application No. 10732183.8, Supplementary Search Report dated Jun. 14, 2012.
European Patent Application No. 10732178.8, Extended European Search Report, dated Aug. 28, 2012.
Intl. Application No. PCT/EP2009/056976, International Search Report dated Dec. 7, 2009.
Israel Patent Application No. 216731, Office Action dated Jan. 29, 2014.
Israel Patent Application No. 216731, Office Action dated Feb. 24, 2013.
Israel Patent Application No. 214072, Office Action dated Jan. 2, 2014.
Israel Patent Application No. 216731, Office Action, dated Jul. 30, 2014.
Japanese Patent Application No. 2011-546408, Office Action dated Jul. 18, 2013.
Japanese Patent Application No. 2011-546410, Office Action, dated Jun. 12, 2014.
Singapore Patent Application No. 2011092582, Written Opinion, dated Sep. 22, 2014.
Singapore Patent Application No. 201105100-0, Written Opinion, dated Jun. 15, 2012.
Singapore Patent Application No. 2011050994, Written Opinion, dated Sep. 18, 2014.
Singapore Patent Application No. 201109258-2, Written Opinion dated May 30, 2013.
Singapore Patent Application No. 201105100-0, Examination Report dated Mar. 4, 2013.
Singapore Patent Application No. 201105099-4, Written Opinion dated Jun. 8, 2012.
U.S. Appl. No. 12/340,436, Office Action dated Oct. 5, 2010.
U.S. Appl. No. 12/340,436, Office Action dated Jun. 24, 2011.
U.S. Appl. No. 13/607,508, Office Action, dated Oct. 28, 2014.
U.S. Appl. No. 13/911,329, Office Action, dated Oct. 16, 2014.
Anti-c-erbB-2 (HER-2/neu) [CB11], BioGenex, Doc. No. 932-134MR, Rev. D; Release Date Jul. 25, 2016; available via the Internet at http://store.biogenex.com/download.php?filename=C-erbB-2_Antibody_Clone_SP3.pdf.
Foreman, P. et al., "ErbB3 Inhibitory Surrobodies Inhibit Tumor Cell Proliferation in Vitro and in Vivo," Mol. Cancer Ther. 11:1141-1420 (2012).
Gabos, Z. et al., "Prognostic Significance of Human Epidermal Growth Factor Receptor Positivity for the Development of Brain Metastasis After Newly Diagnosed Breast Cancer," J. Clin. Oncol. 24(36):5658-5663 (2006).

* cited by examiner

FIGURE 1 p95.D series

| Hit | Her2-D pep | Her2-hFc | Her2-A pep |
|---|---|---|---|
| D1 | 0.837 | 0.563 | 1.553 |
| D3 | 2.306 | 0.089 | 0.134 |
| D4 | 3.941 | 1.683 | 0.107 |
| D5 | 3.417 | 0.094 | 0.108 |
| D6 | 0.902 | 1.720 | 0.086 |
| D7 | 2.087 | 0.115 | 0.093 |
| D8 | 3.701 | 0.219 | 0.084 |
| D9 | 3.460 | 0.311 | 0.084 |
| D10 | 3.120 | 0.087 | 0.094 |
| D11 | 3.392 | 0.103 | 0.081 |
| D12 | 3.871 | 4.000 | 0.092 |
| D13 | 1.189 | 0.092 | 0.096 |
| Her2 Ab5 | | 3.929 | |
| A3 | | | 3.130 |

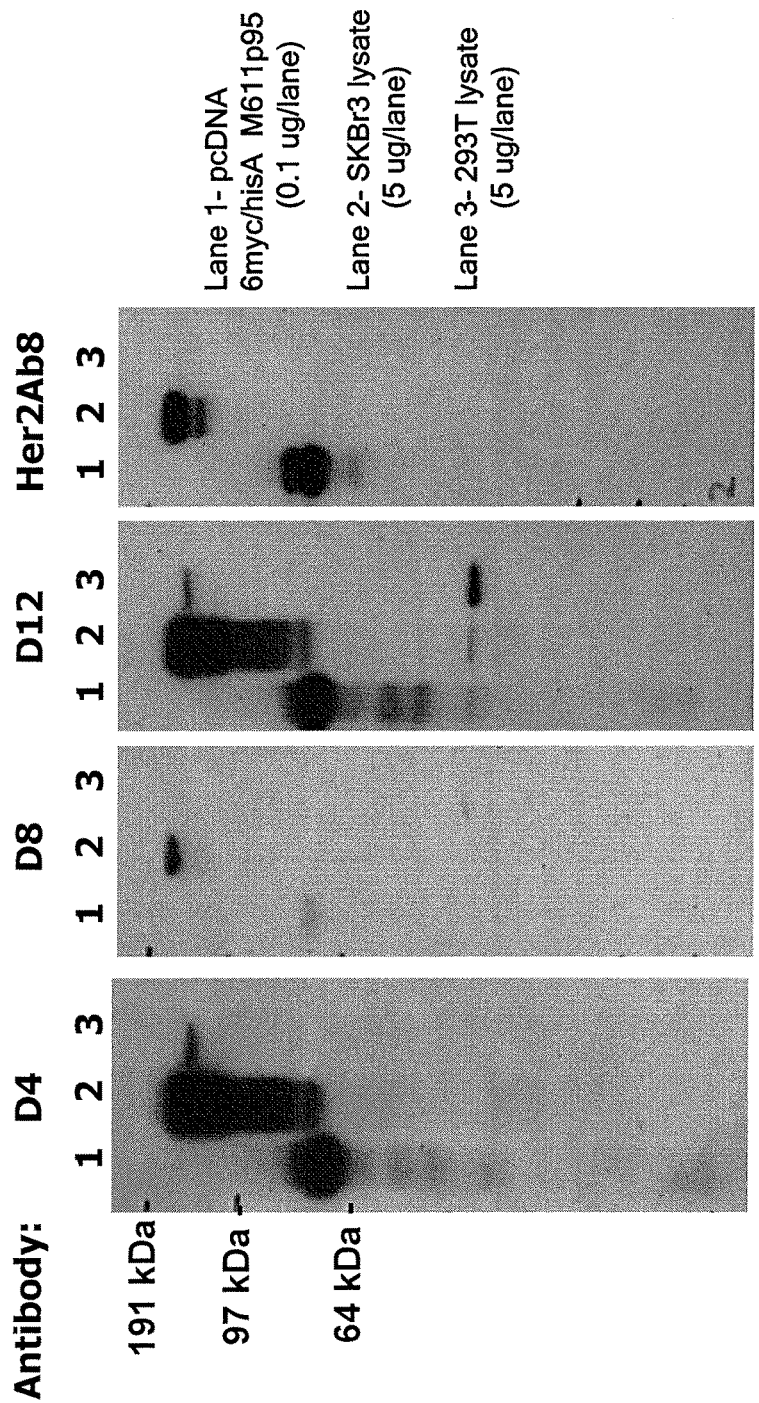

p95.D series - native FACS stain p95.D fixed / permanent FACS stain p95 and HER2 Expression

FIGURE 5a
Veratag Assay Workflow
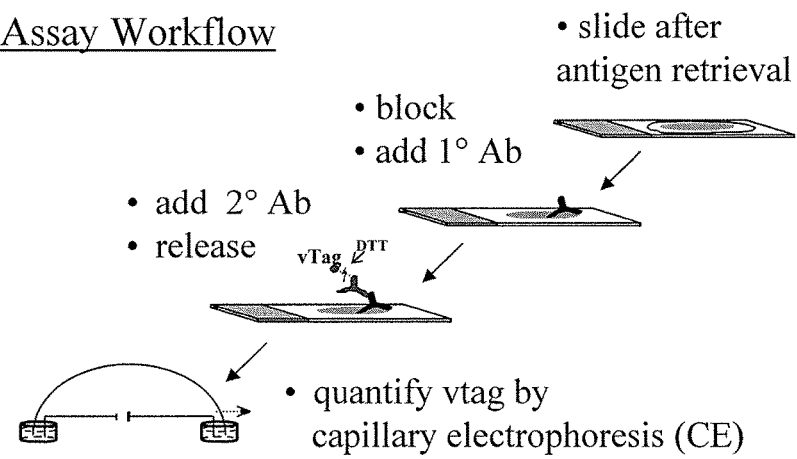
- slide after antigen retrieval
- block
- add 1° Ab
- add 2° Ab
- release
- quantify vtag by capillary electrophoresis (CE)
p95 Assay Configuration
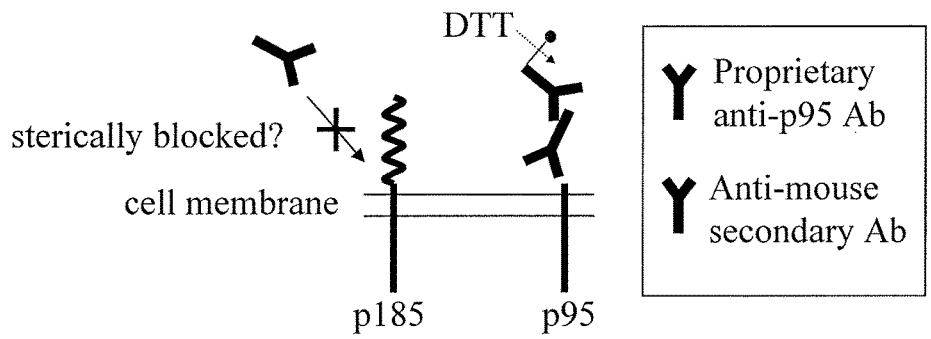
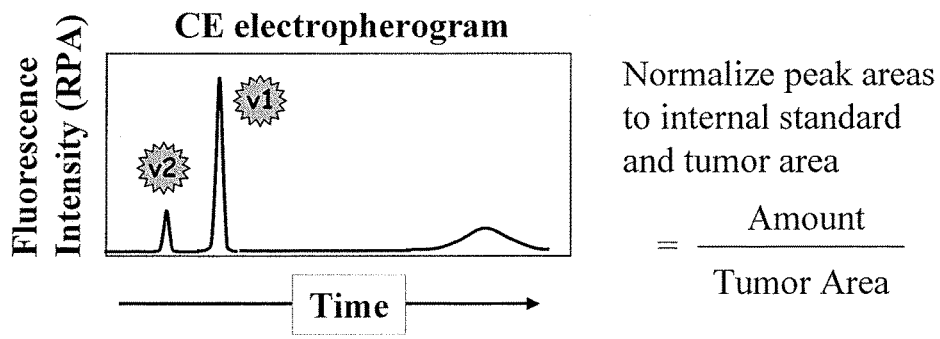
Normalize peak areas to internal standard and tumor area
$$= \frac{\text{Amount}}{\text{Tumor Area}}$$

Tumor Reproducibility

Use of Standards to Achieve Consistency Over Time

- Batch to batch consistency achieved using normalization standards
- Here a range of p95 and ADAM10 transfectants were tested representing a range of p95

3 two-way comparisons between operators:

CV's <30% for a range of batches/operators over entire dynamic range

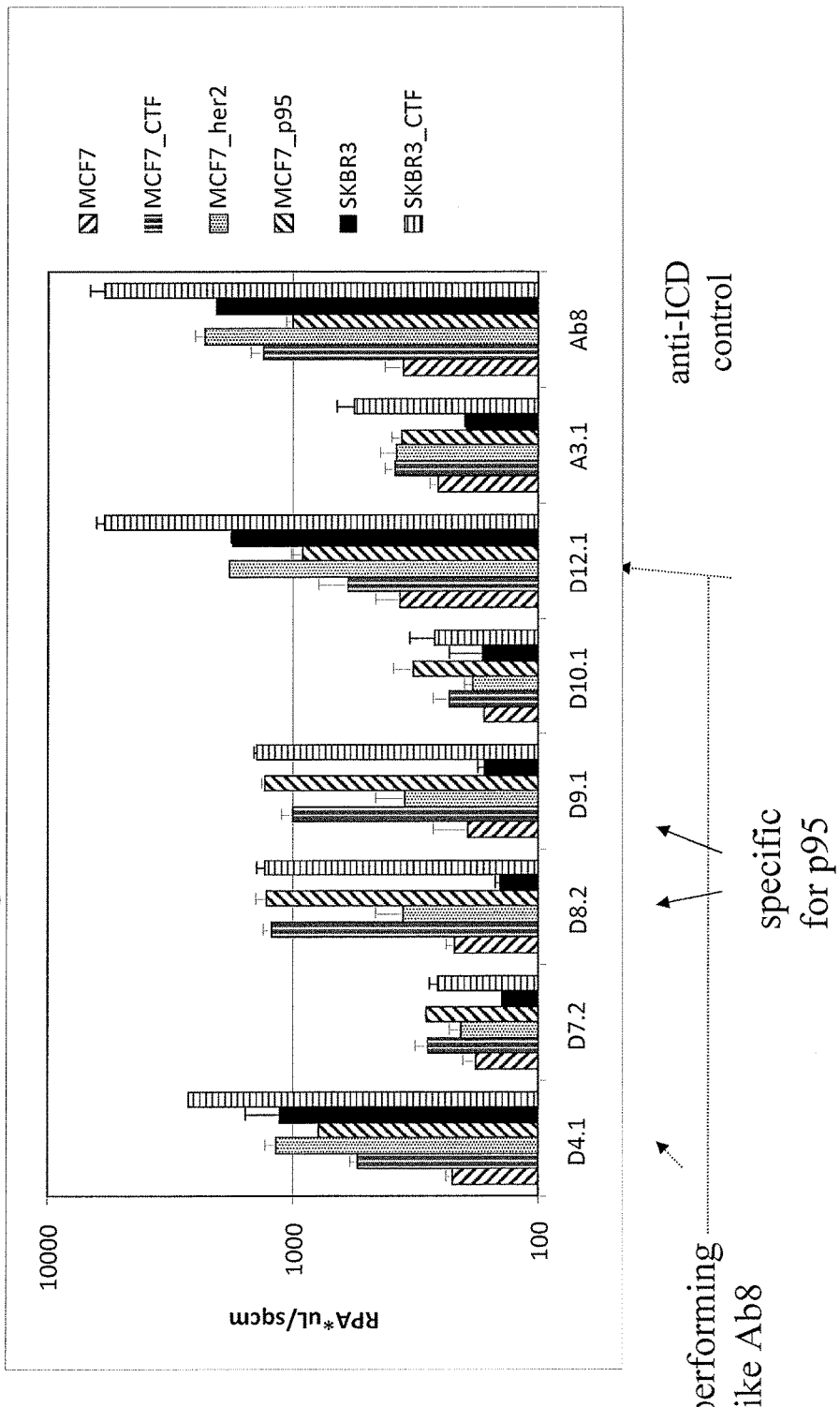

Figure 7a    Measurement in Tumors
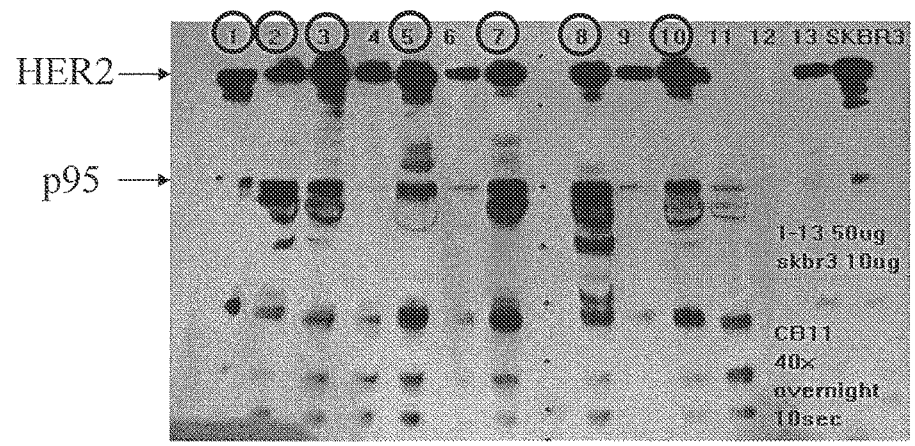
Figure 7b
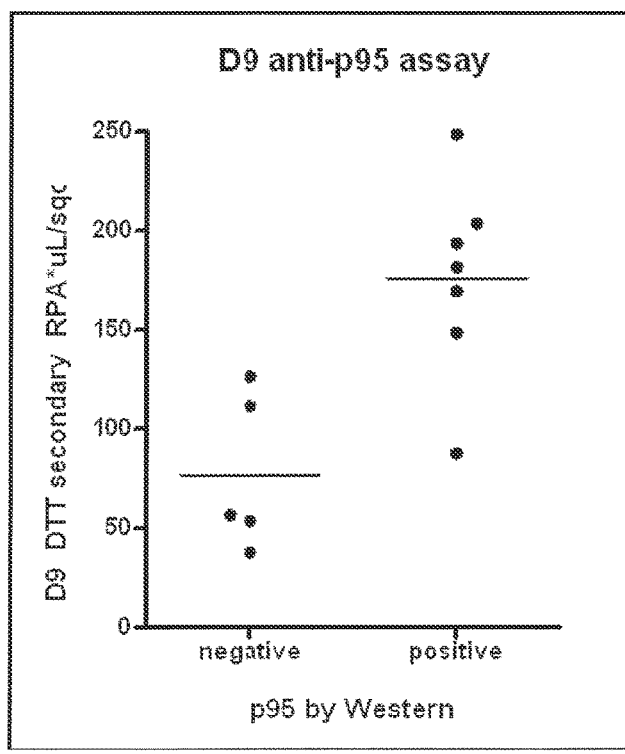

Figure 8a
Isotype Control Experiment
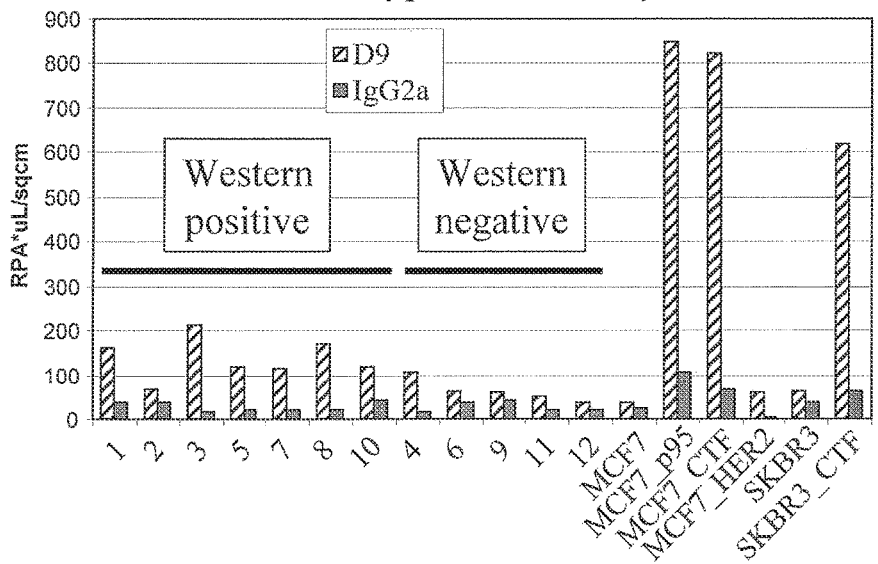
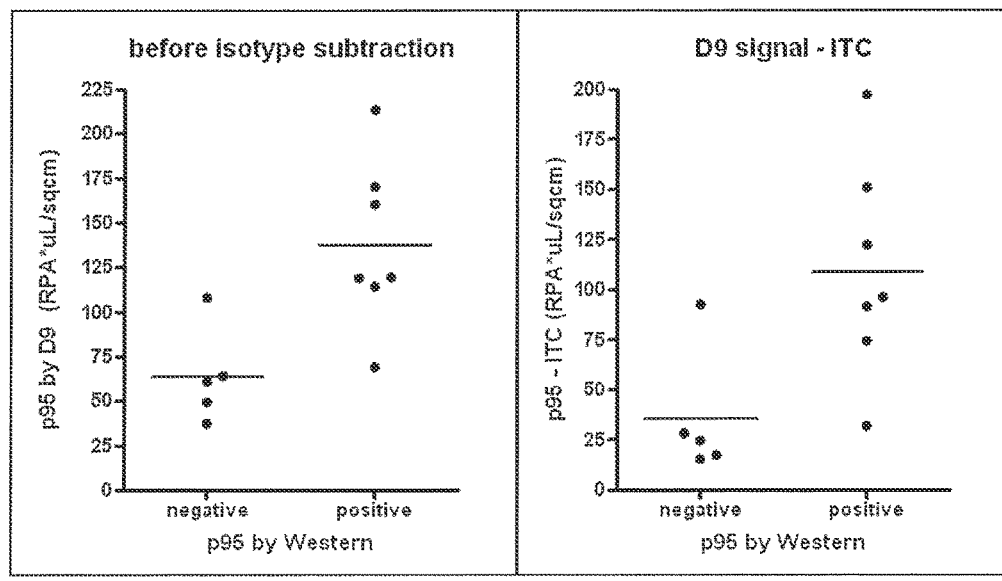
Figure 8b
Figure 8c IHC with anti-p95 clone D9.1 in cell lines

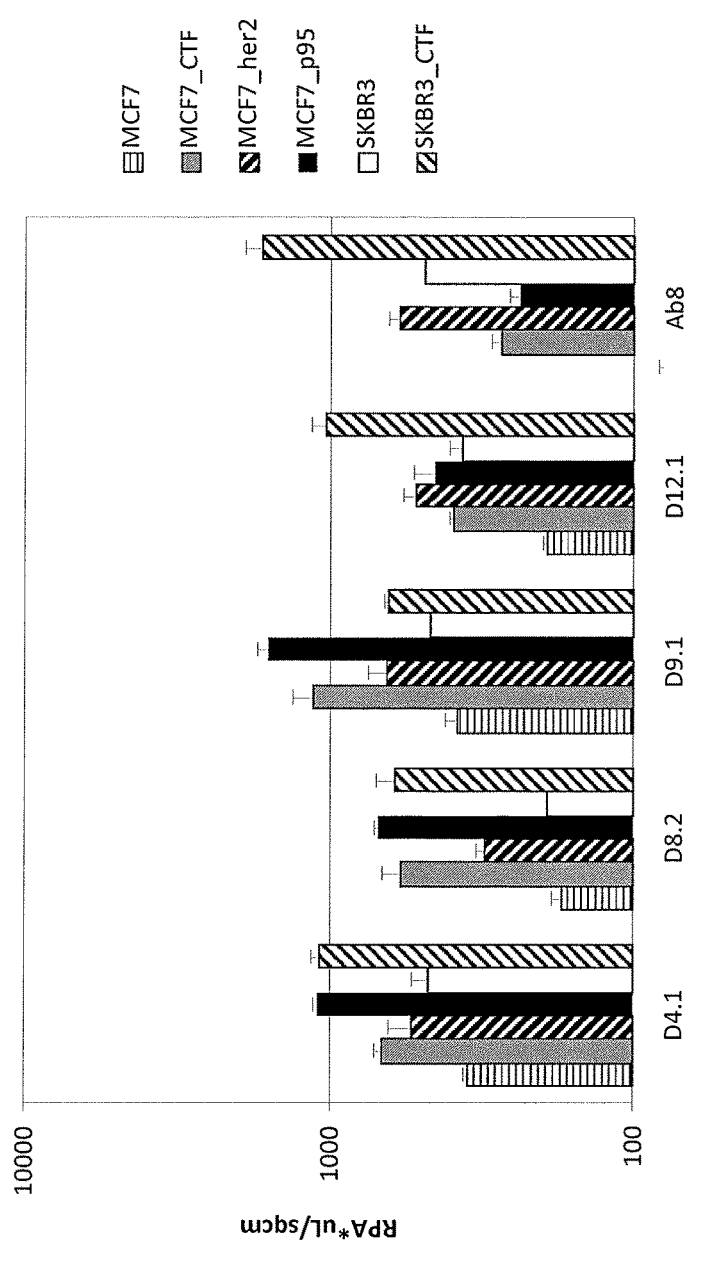

Measurement in Tumors

Cell Line Standards

Outcome as a Function of HER2

- HER2 (H2T) was measured by VeraTag.

- Probability of progression at 12 months was calculated for bins of 30 patients ordered smallest to largest H2T.

- A trend of increasing probability of remaining progression-free past 12 months was observed for increasing H2T.

- A discontinuity in this trend was observed for bins with mean H2T of ~70.

Patients with very high HER2 outcomes similar to FISH

FIGURE 15
(continued)

| FISH Status | HER2 Total Status | n | Median TTP (mo) | TTP HR (p-value) v. FISH(-) | Median OS (mo) | OS HR (p-value) v. FISH(-) |
|---|---|---|---|---|---|---|
| FISH− | log(H2T)<1.25 | 19 | 4.5 | 1 (1) | 28.7 | 1 (1) |
| FISH+ | 1.25<log(H2T)<1.95 | 51 | 12.6 | 0.34 (p<0.0001) | 39.6 | 0.56 (0.085) |
| FISH+ | log(H2T)>1.95 | 15 | 4.6 | 0.87 (0.68) | 28.6 | 0.79 (0.58) |

- The H2T VeraTag assay identified patients with tumors having highly overexpressed HER2 and poor performance on trastuzumab.
- Results were similar when the 9 patients who received trastuzumab-only were excluded (vs. FISH-neg, TTP HR=0.36 (p=0.0004) and 0.92 (p=0.8) for intermediate and highest H2T, respectively).
- Results were similar when the 4 IHC 2+ patients were excluded (vs. FISH-neg, TTP HR=0.35 (p<0.0001) and 0.79 (p=0.5) for intermediate and highest H2T, respectively).
- Inclusion of only p95 negatives in the OS analysis increases the distinction between the intermediate H2T group and the FISH-negative: HR=0.37 (p=0.013).

TTP

METHODS OF PRODUCING ANTIBODIES SPECIFIC FOR P95

PRIORITY

This application is a continuation of U.S. patent application Ser. No. 13/911,329, filed Jun. 6, 2013, which is a divisional of U.S. patent application Ser. No. 12/629,037, filed Dec. 1, 2009, issued as U.S. Pat. No. 8,470,542 on Jun. 25, 2013, which claims the benefit of U.S. Provisional Application No. 61/118,975, filed Dec. 1, 2008, U.S. Provisional Application No. 61/182,282, filed May 29, 2009, and U.S. Provisional Application No. 61/187,960, filed Jun. 17, 2009, the disclosures of each of which are incorporated by reference herein in their entireties.

REFERENCE TO A "SEQUENCE LISTING," A TABLE, OR A COMPUTER PROGRAM LISTING APPENDIX SUBMITTED AS AN ASCII TEXT FILE

The Sequence Listing written in file SequenceListing 57618-946380.txt, created on Jun. 11, 2015, 3,125 bytes, machine format IBM-PC, MS-Windows operating system, is hereby incorporated by reference in its entirety for all purposes.

BACKGROUND OF THE INVENTION

A biomarker is generally a characteristic that is objectively measured and evaluated as an indicator of normal biological processes, pathogenic processes or pharmacological responses to a therapeutic intervention. See Atkinson et al., 2001, *Clin. Pharmacol. Ther.* 69:89-95. Biomarkers vary widely in nature, ease of measurement and correlation with physiological states of interest. See, e.g., Frank et al., 2003, *Nature Reviews Drug Discovery* 2:566-580. It is widely believed that the development of new validated biomarkers will lead both to significant reductions in healthcare and drug development costs and to significant improvements in treatment for a wide variety of diseases and conditions. Thus, a great deal of effort has been directed to using new technologies to find new classes of biomarkers. See, e.g., Petricoin et al., 2002, *Nature Reviews Drug Discovery*, 1:683-695; and Sidransky, 2002, *Nature Reviews Cancer* 2:210-219.

The interactions of cell surface membrane components play crucial roles in transmitting extracellular signals to a cell in normal physiology and in disease conditions. In particular, many types of cell surface receptors undergo dimerization, oligomerization or clustering in connection with the transduction of an extracellular event or signal into a cellular response, such as, e.g., proliferation, increased or decreased gene expression or the like. See, e.g., George et al., 2002, *Nature Reviews Drug Discovery* 1:808-820; Mellado et al, 2001, *Ann. Rev. Immunol.* 19:397-421; Schlessinger, 2000, *Cell* 103:211-225; and Yarden, 2001, *Eur. J. Cancer* 37:S3-S8. The role of such events in diseases, such as cancer, has been the object of intense research and has led to the development of several new drugs and drug candidates. See, e.g., Herbst and Shin, 2002, *Cancer* 94:1593-1611; Yarden and Sliwkowski, 2001, *Nature Reviews Molecular Cell Biology* 2:127-137; McCormick, 1999, *Trends in Cell Biology* 9:53-56 (1999); and Blume-Jensen and Hunter, 2001, *Nature* 411:355-365.

Expression levels of individual cell surface receptors, such as Her-2 in breast cancer, have been used as biomarkers, especially to determine patient prognosis or whether a patient will or will not respond to certain treatments. Conventional immunohistochemical (IHC) or fluorescence in situ hybridization (FISH) analyses have been used to detect Her-2 overexpression to determine whether treatment with a Her2-acting agent, e.g., trastuzumab, is warranted. Unfortunately, IHC and FISH have certain limitations as diagnostic tools in that they are not necessarily accurate and also prone to different interpretations by different laboratory personnel. Her-2 is also over-expressed in other cancers such as ovarian cancer, non-small cell lung cancer, colon cancer, prostate cancer and pancreatic cancer. See Mosession et al., 2004, *Semin. Cancer. Biol.* 14:262-270.

A subgroup of Her-2-overexpressing tumors also have p95Her-2 (p95), an N-terminal truncated version of Her-2 that has shed the ectodomain, to which trastuzumab binds. Data suggest that the presence of p95 correlates to the extent of lymph node involvement, suggesting that p95 may be an important prognostic factor for breast cancer metastases. See Molina et al., 2002, *Clin. Can. Res.* 8:347-353. Interestingly, trastuzumab binds Her-2 but cannot bind the p95 truncated Her-2 so trastuzumab is ineffective in patients with high levels of p95.

BRIEF DESCRIPTION OF THE INVENTION

In a first aspect, the invention is drawn to a method of measuring and/or quantifying the presence and/or amount of p95 and/or p95 complex in a sample, the method comprising providing a sample and determining the presence and/or quantity of p95 and/or p95 complex in the sample. In a preferred embodiment, the sample is a biological sample. In a preferred embodiment, the sample is a tissue sample. In a preferred embodiment, the sample is a fixed sample, a frozen sample or a lysate. In a preferred embodiment, the sample is a tumor sample. In a preferred embodiment, the sample is a frozen tumor tissue sample. In a preferred embodiment, the sample comprises a tumor lysate. In a preferred embodiment, the sample comprises a breast cancer sample. In a preferred embodiment, the sample is an FFPE sample. In a preferred embodiment, the sample is a blood, plasma or lymph sample. In a preferred embodiment, the blood or plasma sample contains circulating tumor cells. In a preferred embodiment, the sample contains exosomes and/or other vesicles. In a preferred embodiment, the sample comprises cell lines. In a preferred embodiment, the measurement may be quantitative across a wide dynamic range.

In a second aspect, the invention is drawn to a method of measuring and/or quantifying the presence and/or quantity of p95 and/or p95 complex in a sample, the method comprising mixing a sample with a binding compound and determining the presence and/or quantity of binding compound bound to p95 and/or p95 complex. In a preferred embodiment, the binding compound is capable of specifically binding p95. In a preferred embodiment, the binding compound comprises an antibody. In a preferred embodiment, the antibody was raised against one of the peptides having SEQ ID NOs 1-7.

SEQ ID NO 1
MPIWKFPDEEGACQPCPINCTHSCVDLDDKGCPAEQRASPLTSIIS

SEQ ID NO 2
ASPLTSIIS

-continued

```
                                          SEQ ID NO 3
PAEQRASPLTSIIS

SEQ ID NO 4
QPCPINCTHSCVDLDDKGCPA

SEQ ID NO 5
MPIWKFPDEEGA

SEQ ID NO 6
PSGVKPDLSYMPIWK

SEQ ID NO: 7
Ac-QPCPINCTHSCVDLDDKGCPAKK(eNH)-[KLH]
  (shown as conjugated to KLH)
```

In certain embodiments, the antibody is or comprises one of the antibodies produced by hybridoma cell lines deposited with the ATCC having accession number PTA-9738 (p95.D3.4), PTA-9739 (p95.D8.2) and PTA-9740 (p95.D9.1). In one embodiment, the antibody is p95.D9.1. In a preferred embodiment, the sample is a biological sample. In a preferred embodiment, the sample is a tissue sample. In a preferred embodiment, the sample is a fixed sample, a frozen sample or a lysate. In a preferred embodiment, the sample is a tumor sample. In a preferred embodiment, the sample is a frozen tumor tissue sample. In a preferred embodiment, the sample comprises a tumor lysate. In a preferred embodiment, the sample comprises a breast cancer sample. In a preferred embodiment, the sample is an FFPE sample. In a preferred embodiment, the sample is a blood, plasma or lymph sample. In a preferred embodiment, the blood or plasma sample contains circulating tumor cells. In a preferred embodiment, the sample contains exosomes and/or other vesicles. In a preferred embodiment, the sample comprises cell lines. In a preferred embodiment, the measurement may be quantitative across a wide dynamic range.

In a preferred embodiment, determining the presence and/or quantity of binding compound bound to p95 further comprises providing a second binding compound, the second binding compound being able to specifically bind the binding compound bound to p95 and determining the presence and/or quantity of the second binding compound as correlative of the presence and/or quantity of the binding compound bound to p95. In a preferred embodiment, the second binding compound is an antibody.

In a third aspect, the invention is drawn to a method of measuring and/or quantifying the presence and/or quantity of p95 and/or a p95 complex in a sample, the method comprising: mixing (i) a sample that may contain p95 and/or p95 complex; (ii) a proximity probe that is capable of binding p95 and/or at least one other analyte in a p95 complex, the proximity probe having an effective proximity; and (iii) at least one binding compound, the at least one binding compound being capable of binding p95 and/or at least one other analyte and having one or more signaling molecules attached, wherein binding of the proximity probe and binding compound within the effective proximity produces a signal from the molecular tags that correlates with the presence and/or quantity of p95 and/or the p95 complex. In a preferred embodiment, the proximity probe and/or binding compound is capable of specifically binding p95 or the at least one other analyte. In a preferred embodiment, the proximity probe and/or binding compound further comprises an antibody. In a preferred embodiment, the proximity probe and/or the binding compound further comprises an antibody, and each antibody binds to a specific epitope on p95. In a preferred embodiment, the antibody was raised against one of the peptides having SEQ ID NOs 1-6. In certain embodiments, the antibody is or comprises one of the antibodies produced by hybridoma cell lines deposited with the ATCC having accession number PTA-9738 (p95.D3.4), PTA-9739 (p95.D8.2) and PTA-9740 (p95.D9.1). In one embodiment, the antibody is p95.D9.1.

In a preferred embodiment, the proximity probe comprises an antibody and a first nucleic acid and the binding compound comprises an antibody and a second nucleic acid, wherein the first and the second nucleic acids are complementary to each other and able to hybridize to determine the effective proximity and produce the signal, directly or indirectly, through hybridization. Hybridization may be quantified by any method known to one skilled in the art such as, for example, measuring molecular tags attached to the nucleic acid molecules or measuring hybridization with any method known to one skilled in the art. In a preferred embodiment, hybridization is measured through a nucleic acid amplification method such as, for example, the rolling circle amplification method. In a preferred embodiment, the antibody was raised against one of the peptides having SEQ ID NOs 1-7. In certain embodiments, the antibody is or comprises one of the antibodies produced by hybridoma cell lines deposited with the ATCC having accession number PTA-9738 (p95.D3.4), PTA-9739 (p95.D8.2) and PTA-9740 (p95.D9.1). In one embodiment, the antibody is p95.D9.1 In a preferred embodiment, the sample is a biological sample. In a preferred embodiment, the sample is a tissue sample. In a preferred embodiment, the sample is a fixed sample, a frozen sample or a lysate. In a preferred embodiment, the sample is a tumor sample. In a preferred embodiment, the sample is a frozen tumor tissue sample. In a preferred embodiment, the sample comprises a tumor lysate. In a preferred embodiment, the sample comprises a breast cancer sample. In a preferred embodiment, the sample is an FFPE sample. In a preferred embodiment, the sample is a blood, plasma or lymph sample. In a preferred embodiment, the blood or plasma sample contains circulating tumor cells. In a preferred embodiment, the sample contains exosomes and/or other vesicles. In a preferred embodiment, the sample comprises cell lines. In a preferred embodiment, the measurement may be quantitative across a wide dynamic range.

In a preferred embodiment, the proximity probe comprises a cleaving probe that has a cleavage inducing moiety and the at least one binding compound has one or more molecular tags attached to the binding compound by a cleavable linkage, wherein the cleavable linkage may be cleaved within the effective proximity producing a signal that correlates with the presence and/or quantity of p95 and/or p95 complex. In a preferred embodiment, the binding compound and/or the cleaving probe further comprises an antibody, and each antibody binds to a specific epitope on p95 and/or at least one other analyte in a p95 complex. In a preferred embodiment, the antibody was raised against one of the peptides having SEQ ID NOs 1-7. In certain embodiments, the antibody is or comprises one of the antibodies produced by hybridoma cell lines deposited with the ATCC having accession number PTA-9738 (p95.D3.4), PTA-9739 (p95.D8.2) and PTA-9740 (p95.D9.1). In one embodiment, the antibody is p95.D9.1. In a preferred embodiment, the sample is a biological sample. In a preferred embodiment, the sample is a tissue sample. In a preferred embodiment, the sample is a fixed sample, a frozen sample or a lysate. In a preferred embodiment, the sample is a tumor sample. In a preferred embodiment, the sample is a frozen tumor tissue sample. In a preferred embodiment, the sample comprises a tumor lysate. In a preferred embodiment, the sample comprises a breast cancer sample. In a preferred embodiment, the sample is an FFPE sample. In a preferred embodiment, the sample is a blood, plasma or lymph sample. In a preferred embodiment, the blood or plasma sample contains circulating tumor cells. In a preferred embodiment, the sample contains exosomes and/or other vesicles. In a preferred embodiment, the sample comprises cell lines. In a preferred embodiment, the measurement is quantitative across a wide dynamic range.

In a fourth aspect, the invention is drawn to a purified antibody that binds to p95. In a preferred embodiment, the purified antibody binds specifically to p95. In a preferred embodiment, the antibody binds specifically to the extracellular domain of p95 but not full length HER2. In a preferred embodiment, the antibody is a polyclonal antibody or a monoclonal antibody. In a preferred embodiment, the antibody is a monoclonal antibody. In a preferred embodiment, the antibody was raised against one of the peptides having SEQ ID NOs 1-7. In certain embodiments, the antibody is or comprises one of the antibodies produced by hybridoma cell lines deposited with the ATCC having accession number PTA-9738 (p95.D3.4), PTA-9739 (p95.D8.2) and PTA-9740 (p95.D9.1). In one embodiment, the antibody is p95.D9.1.

In a fifth aspect, the invention is drawn to a method for determining whether a subject with a cancer is likely to respond to treatment with a targeted therapy, for predicting a time course of disease and/or for predicting probability of a significant event in the time course of the subject's cancer based on a measurement of an amount of p95 and/or a p95 complex in a sample. In one embodiment, the invention is drawn to a method for determining whether a subject with a cancer is likely to respond to treatment with a Her-2 acting agent. In another embodiment, the method is drawn to a method of predicting a time course of a disease in a subject with a cancer. In another embodiment, the method is drawn to predicting the probability of a significant event in a subject with a cancer.

In a preferred embodiment, a time course is measured by determining the time between significant events in the course of a patient's disease, wherein the measurement is predictive of whether a patient has a long time course. In a preferred embodiment, the significant event is the progression from primary diagnosis to death. In a preferred embodiment, the significant event is the progression from primary diagnosis to metastatic disease. In a preferred embodiment, the significant event is the progression from primary diagnosis to relapse. In a preferred embodiment, the significant event is the progression from surgery to death. In a preferred embodiment, the significant event is the progression from surgery to metastases. In a preferred embodiment, the significant event is the progression from surgery to relapse. In a preferred embodiment, the significant event is the progression from metastatic disease to death. In a preferred embodiment, the significant event is the progression from primary diagnosis to relapse. In a preferred embodiment, the significant event is the progression from metastatic disease to relapse. In a preferred embodiment, the significant event is the progression from relapse to death. In a preferred embodiment, the time course is measured with respect to overall survival rate, time to progression and/or using the RECIST or other response criteria.

In a preferred embodiment, the subject's cancer is breast cancer. In a preferred embodiment, the targeted therapy comprises a Her-2 acting agent. In a preferred embodiment, the Her-2 acting agent is trastuzumab and/or pertuzumab. In a preferred embodiment, the Her-2 acting agent is a tyrosine kinase inhibitor and if the amount of p95 is high, then the patient is likely to respond to the targeted therapy, the patient is likely to have a long time course and/or the patient is not likely to have a significant event. In a preferred embodiment, the Her-2 acting agent is lapatinib. In a preferred embodiment, the targeted therapy is an inhibitor, such as a protease inhibitor, and if the amount of p95 is high, then the patient is likely to respond to the targeted therapy, the patient is likely to have a long time course and/or the patient is not likely to have a significant event. In a preferred embodiment, the inhibitor inhibits metalloproteases including, but not limited to, matrix metalloproteases and/or member(s) of the ADAM family of proteases. In a preferred embodiment, the inhibitor inhibits ADAM10.

In a preferred embodiment, determining whether an amount of p95 is low is done by comparing the amount of p95 in the subject's cancer to an optimal cutoff. Such optimal cutoffs are disclosed herein, and certain embodiments of the invention are meant to include amounts that are approximate to the amounts mentioned and disclosed herein. In certain embodiments, the amount of p95 in the subject is compared to an optimal cutoff, and the optimal cutoff is used to determine whether a patient will respond to an appropriate treatment.

In a further aspect, the invention provides methods of treating a subject with cancer. In one aspect, the methods comprise determining that the subject is afflicted with a cancer that is likely to respond to treatment and/or has a long time course according to a method of the invention, and administering an effective amount of compound to the subject as a result of said determination. In another aspect, the methods comprise determining that a subject is afflicted with a cancer that is likely to respond to treatment according to a method of the invention, then advising a medical professional of the treatment option of administering to the subject an effective amount of an agent. In another aspect, the agent is at least two agents and the medical professional is advised of treatment options based upon the methods of the invention.

BRIEF DESCRIPTION OF THE DRAWINGS

FIG. 1 shows ELISA data for antibodies generated against a p95 peptide (shown as SEQ ID No. 5). Conditioned media from individual hybridoma clones (D1-D13, listed in column 1) were tested in ELISA assays against the p95 peptide used for immunizing the mice from which the hybridomas were derived (labeled Her2-D pep, shown in column 2), the HER2 extracellular domain (HER2-ECD, labeled as Her2-hFc, shown in column 3), and a peptide different from that used in immunization (labeled as Her2-A pep, shown in column 4). Positive controls for both the HER2-ECD and the Her2-A peptide are also shown. Highlighted cells in the table show positive reactivity in the ELISA test. Several clones show reactivity to the p95 peptide used for immunization but little reactivity with the HER2-ECD (clones D3, D5, D7-11 and D13). Others show reactivity to both the p95 peptide and the HER2-ECD (clones D4, D6, and D12).

FIG. 2 shows Western blot screening of hybridoma conditioned media. 5 ug cell lysate from either 293T cells (lane 3) and SKBR3 cells (lane 2) and 1 ug cell lysate from 293T cells transfected with pcDNA6-p95 (an expression vector for p95, lane 1) were separated on 4-12% NuPAGE gels (Invitrogen). The gels were blotted to PVDF membranes that were stained with conditioned media from hybridomas D4, D8, D12 or Her2 Ab8. Her2 Ab8 (Labvision, Fremont, Calif.) was used as positive control antibody and binds to an intracellular epitope of Her2 that is also part of pcDNA6- p95. Bound antibodies were detected with a horseradish peroxidase-conjugated anti-mouse IgG antiserum and an ECL reagent.

Figure 3A:
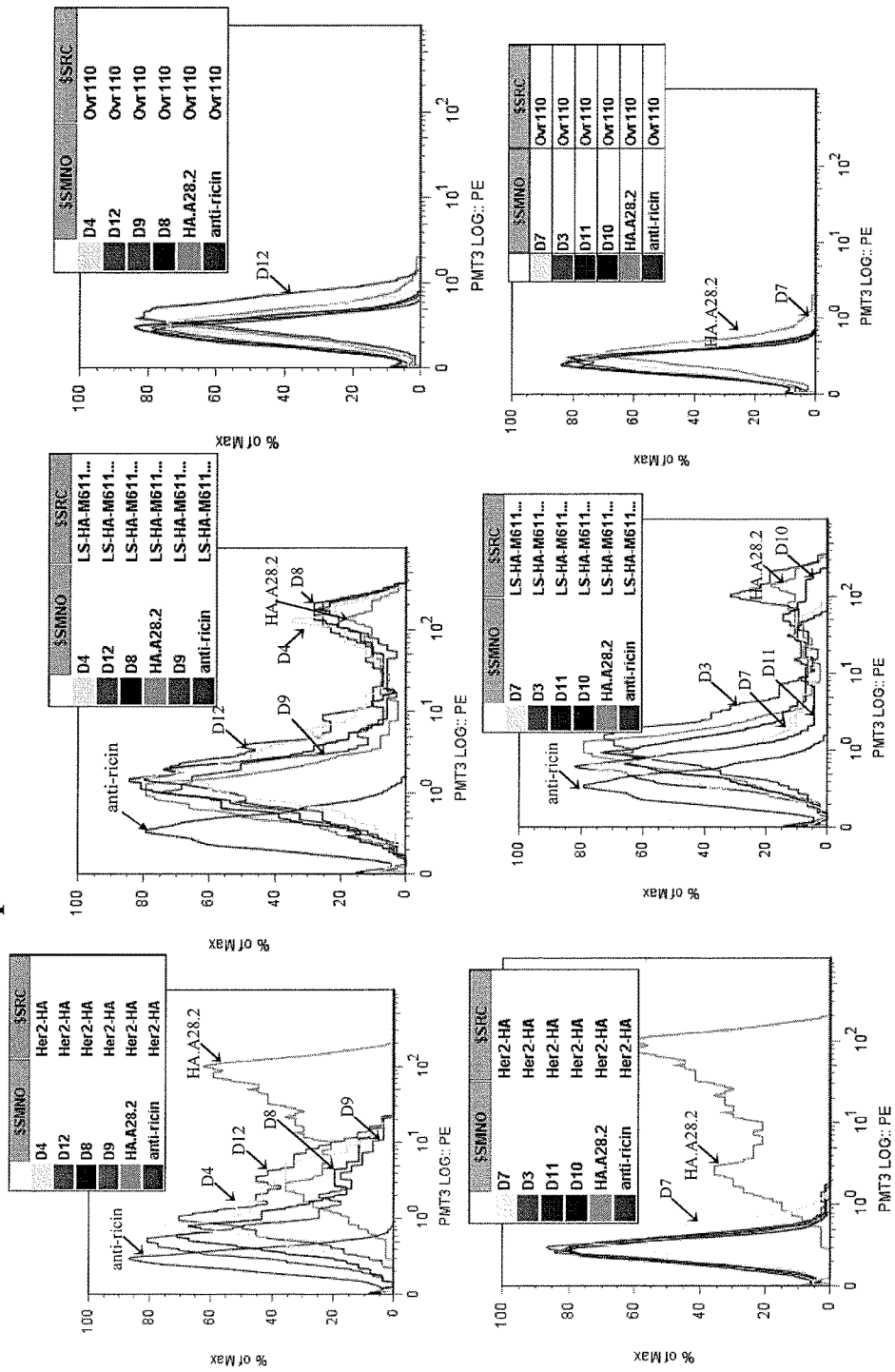
Figure 3B:
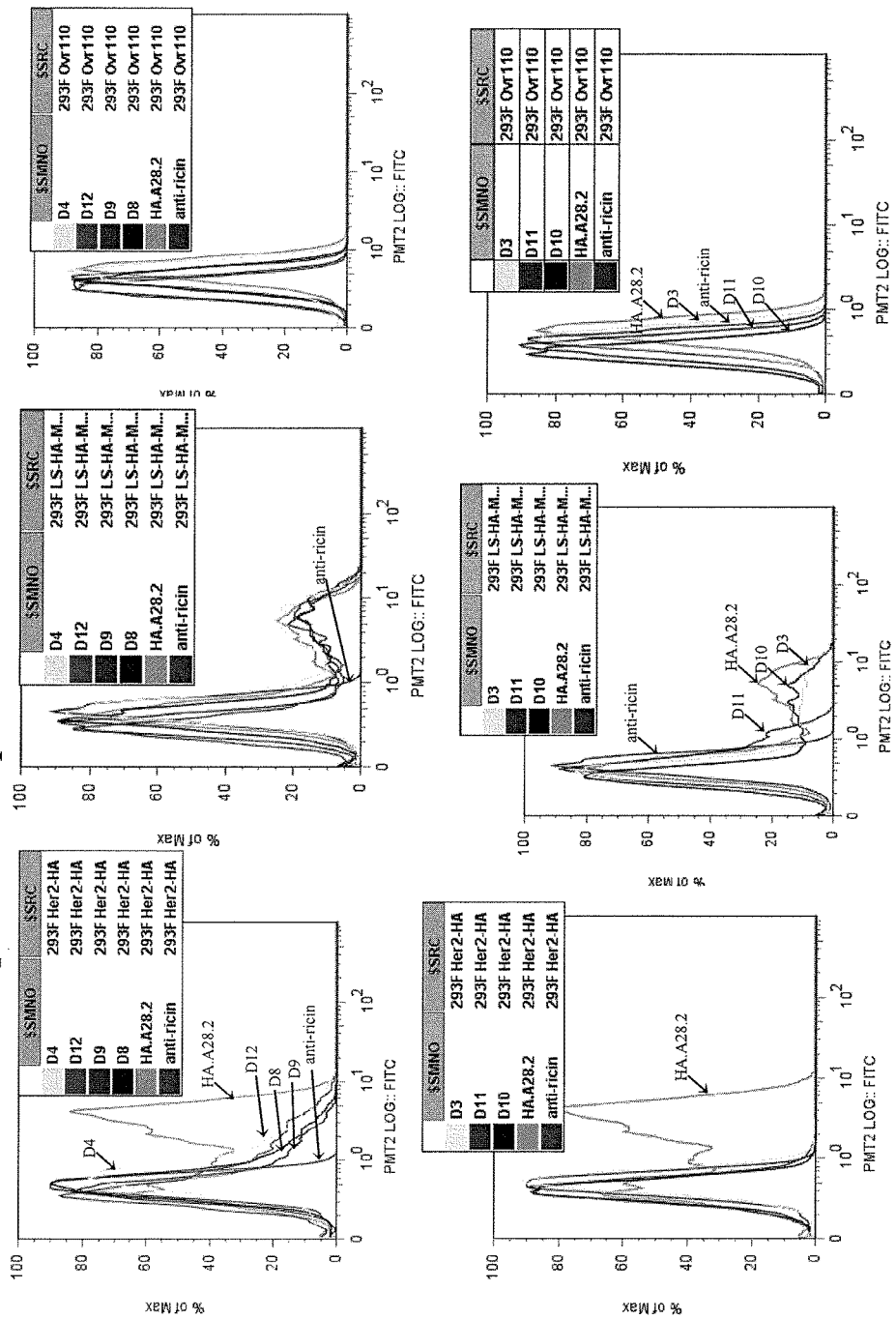

FIGS. 3a and 3b show fluorescence-activated cell sorting (FACS) results from both native cells (FIG. 3a) and cells that were permeabilized and fixed (FIG. 3b). Each panel shows the results of transfected 293T cells bound to conditioned media from different clones (D4, D8, D9 and D12 in the top rows of each figure; D3, D7, D10 and D11 in the bottom rows). Bound antibody was detected with a biotinylated anti-mouse antibody followed by streptavidin-PE. The two panels on the left side show 293T cells transfected with pcDNA6-HER2, which expresses the full length HER2 protein; the two panels in the middle show 293 cells transfected with pcDNA6myc/hisA M611-p95, which expresses p95. Both HER2 and p95 expression proteins have an N-terminal hemagglutinin tag. The two panels on the right side show 293T cells transfected with a vector that expresses an irrelevant protein. Each panel also shows a positive control (HA.A28.2, an antibody directed to the N-terminal hemagglutinin tags on the expressed p95 and HER2 proteins) and a negative control (an anti-ricin antibody). The y-axis is a histogram showing the number of events at a particular bin of PE signal on the x-axis. The binding characteristics for native vs. fixed cells were similar (except for D11), suggesting that formalin-fixed paraffin-embedded (FFPE) samples may show similar binding characteristics. Antibodies that bound strongly to p95 and weakly to HER2 included clones D4, D8, D9 and D12. Antibodies that bound strongly to p95 but not to HER2 included clones D3, D7, D10 and D11.

Figure 4:
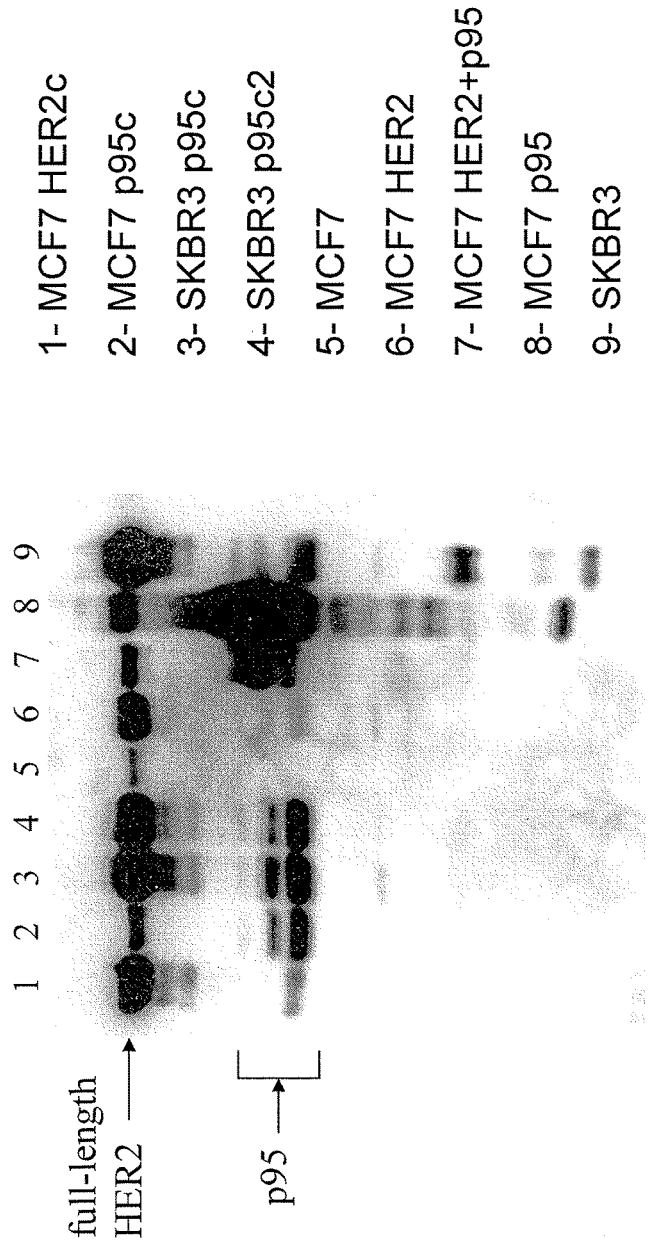

FIG. 4 shows Western blot data for the cells used subsequently in creating formalin-fixed paraffin-embedded (FFPE) blocks. Cell lysates were prepared from samples removed just prior to the addition of fixative. Proteins in these cell lysates were separated using PAGE, transferred to nitrocellulose membranes, blocked, probed with anti-HER2 Ab8 and detected using a horseradish peroxidase detection kit. Lanes 1-4 show cell lysates from MCF-7-HER2c, MCF-7-p95c, SKBR3-p95c and SKBR3-p95c2, respectively. These cells were obtained from the laboratory of Jose Baselga; they express proteins that contain no leader sequence or HA-tag. Lanes 5-8 show lysates from MCF-7 cells (lane 5) and MCF-7 cells transiently transfected with a 50:50 weight mix of pcDNA6-HER2 and empty vector (lane 6), a 50:50 weight mix of pcDNA6-HER2 and pcDNA6myc/hisA M611-p95 (lane 7) or 100% pcDNA6myc/hisA M611-p95 (lane 8). Lane 9 shows cell lysate from SKBR3 cells.

FIG. 5a shows the work flow and assay configuration of a p95 VeraTag assay on FFPE samples. The upper left section of the figure outlines the workflow for the VeraTag assay. A slide containing the sample of interest is deparaffinized and rehydrated, then blocked and p95 antibody is added. A second antibody labeled with VeraTag (i.e., "anti-mouse secondary") is added that binds to the first antibody, as shown in the right part of FIG. 5a. The sample is rinsed and VeraTag is released, captured and measured using capillary electrophoresis (CE). The lower panel of FIG. 5a shows a typical CE electropherogram.

Proprietary software (VeraTag Informer Software) is used to evaluate the raw electropherograms. The software integrates fluorescent peaks associated with the released tag as well as an internal standard, fluorescein of known concentration, used for capillary normalization to give a relative peak area (VeraTag peak area/fluorescein peak area). Separately, the tumor area revealed by hematoxylin and eosin staining is assessed by a pathologist. The relative peak area is divided by this tumor area to give the final value.

Figure 5B:
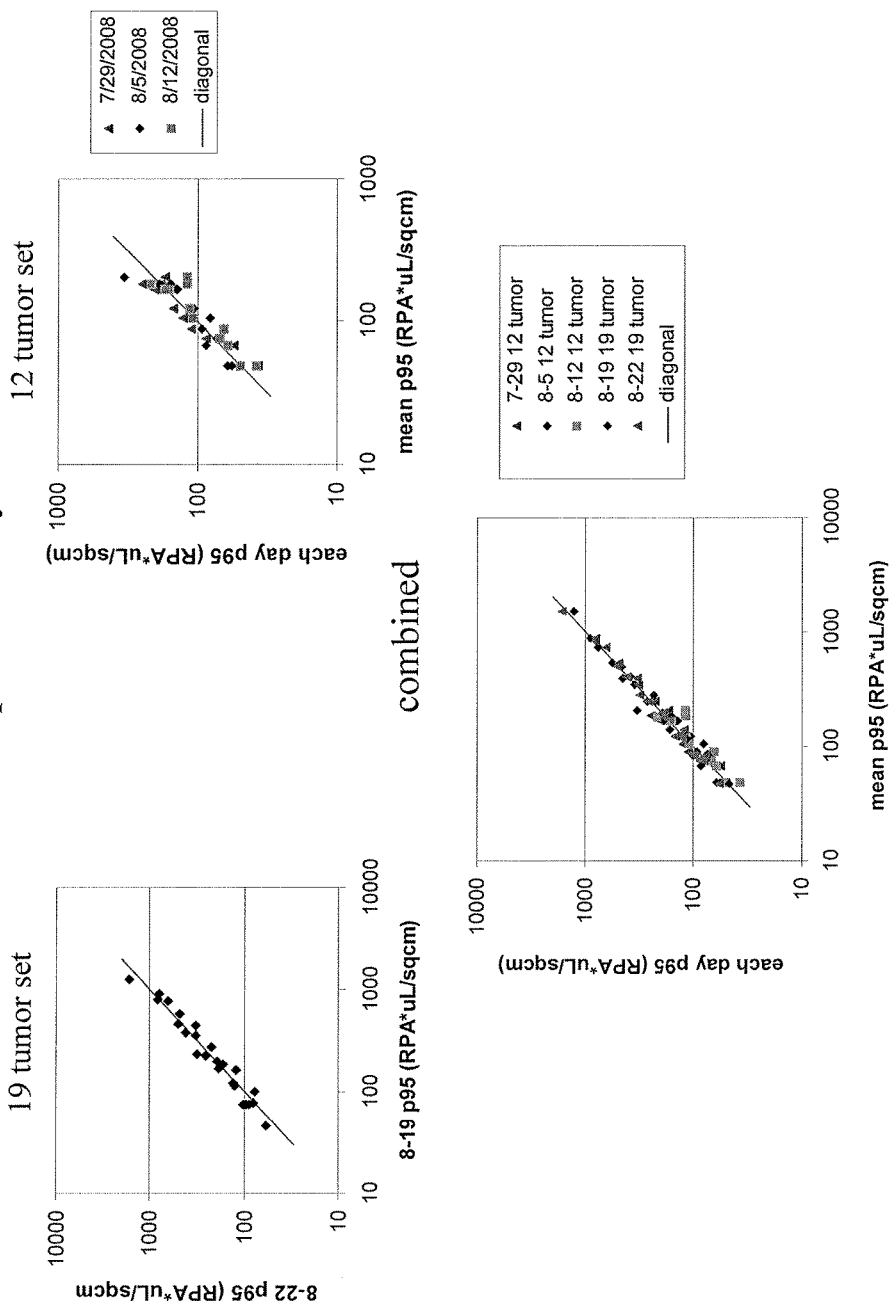

The reproducibility of the assay outlined in FIG. 5a is shown in FIG. 5b using 3 types of comparisons. The upper left panel shows a comparison of assay data accrued for 19 tumor samples on one day (x-axis, 8/19 p95 levels) vs. a second set of data on the same samples accrued on another day (y-axis, 8/22 p95 levels). The upper right panel show analyses of a set of 12 tumor samples performed on 3 different days (y-axis, p95 levels) compared to the mean p95 level (x-axis). The bottom panel of FIG. 5b shows the combined data for all 5 experimental sets (y-axis, p95 levels) compared with the mean p95 level (x-axis, p95 levels). In each panel, the diagonal line represents perfect correlation between x- and y-axis data, which is expressed as relative peak area multiplied by uL per $cm^2$ (RPA*uL/sqcm).

Figure 5C:
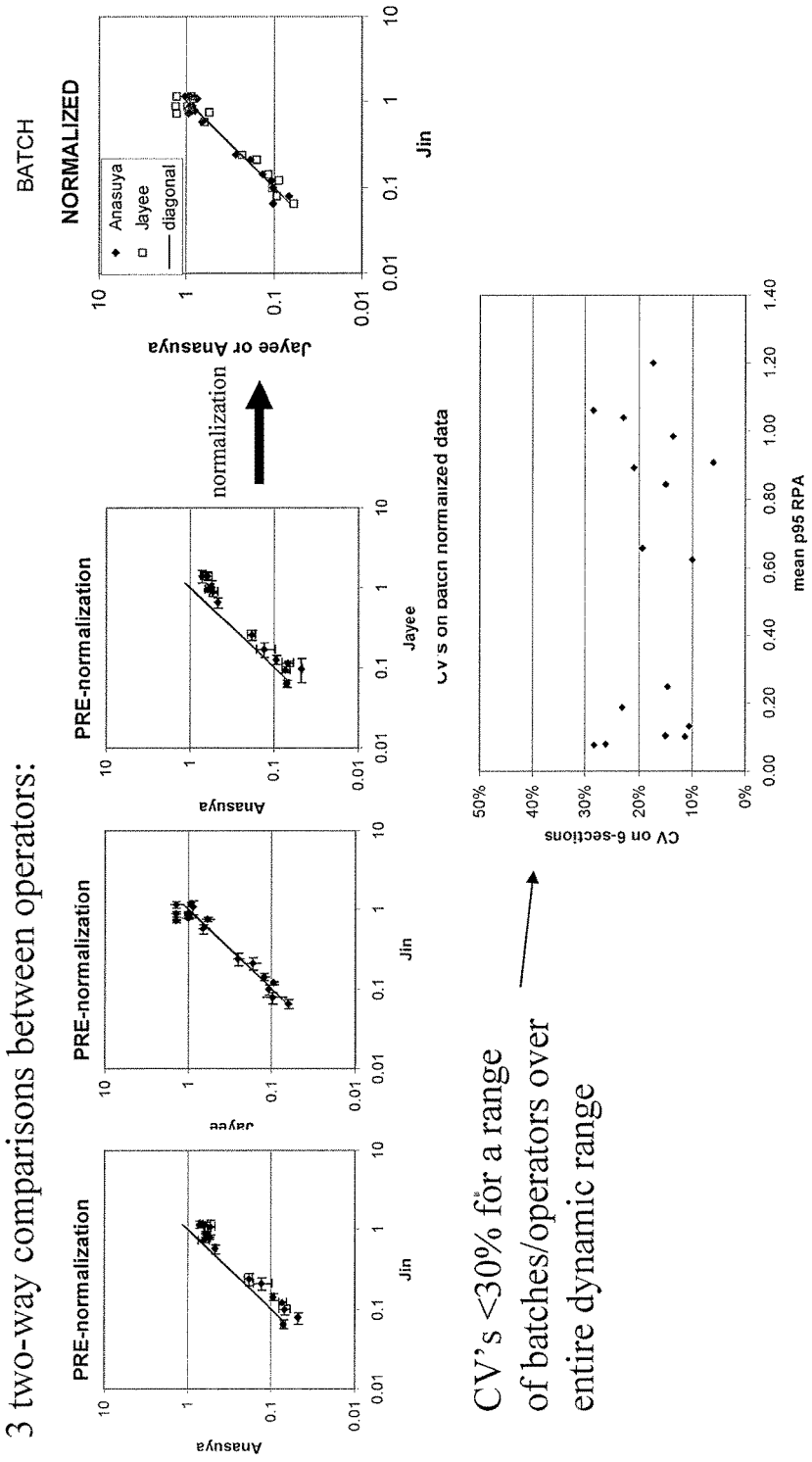

Consistency between operators and over time is critical for standardized assays. FIG. 5c shows how batch consistency was achieved using cell lines with widely varying amounts of p95 as normalization standards. In each of the first three top panels, labeled "PRE-normalization", pairwise comparisons between 3 operators are shown. In each case, the units of p95 are shown as relative peak areas multiplied by uL per $cm^2$ (RPA*uL/sqcm). On the top right panel, the same scores of two operators are plotted against the scores acquired by a third operator after normalization to internal standards. The process for normalization is described in Example 4. The bottom panel shows the coefficient of variability (CV, y-axis) between both batches/operators over a wide range of p95 levels (mean p95 plotted on the x-axis).

FIG. 6 shows the results of a VeraTag assay using different purified antibodies against MCF-7 and SKBR3 cells transfected with a C-terminal fragment (CTF) of HER2, p95 or full length HER2. HER2 CTFs, found in both the cytoplasm and nucleus, are generated by alternative initiation of translation from methionines located near the transmembrane domain of the full-length molecule. Like HER2 and p95, tumors dependent on CTFs are sensitive to kinase inhibitors and like tumors dependent on p95, they do not respond to therapeutic antibodies against HER2. The antibodies used in the VeraTag assay were generated using a peptide (SEQ ID No. 5) from p95. Each purified antibody (D4.1, D7.2, D8.2, D9.1, D10.1 and D12.1 as shown on the x-axis) was tested with 6 cell lines (listed from top to bottom in the legend and displayed from left to right in each bar graph): MCF-7, MCF-7 expressing CTF, MCF-7 expressing HER2, MCF-7 expressing p95, SKBR3 and SKBR3 expressing CTF. The y-axis is shown in Relative Peak Area multiplied by $\mu l/cm^2$ (RPA*uL/sqcm), as set forth in Example 4. Antibody A3.1 was generated by challenging mice with an irrelevant peptide. The positive control was Ab8, which targets the cytoplasmic domain of HER2. Both D4.1 and D12.1 act much like the control antibody. D8.2 and D9.1 show specificity for p95.

Figure 7C:
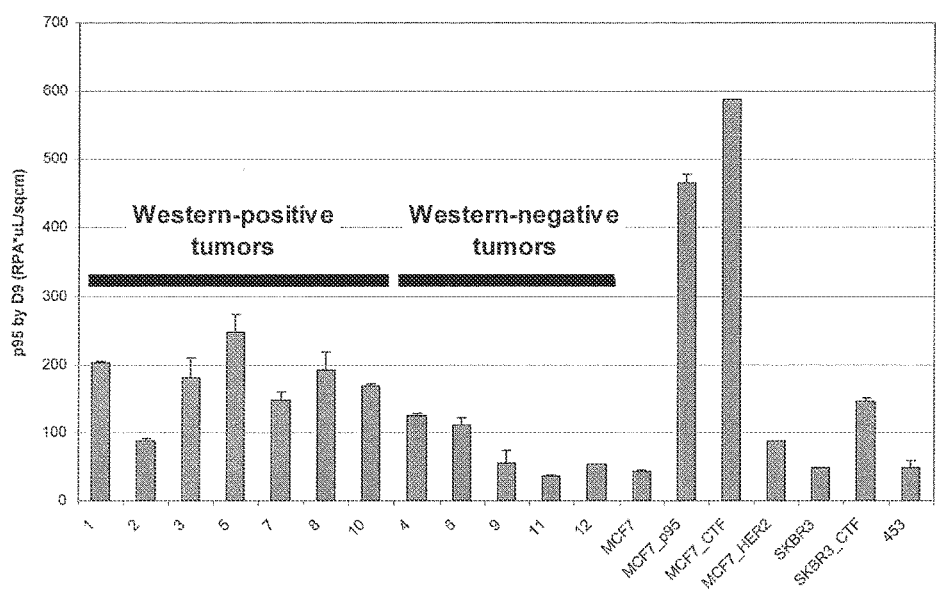

FIGS. 7a-7c show quantitation of p95 in 12 different tumor samples (Cohort A). The 12 tumor samples were chosen to be highly HER2 positive and from patients with node-positive status. Half of each tumor sample was fresh-frozen and half was formalin-fixed and paraffin-embedded. The fresh-frozen samples were used to generate cell lysates that were tested in Western blots for the ability to bind an antibody, CB11, which was raised against the intracellular domain of HER2. The Western blot results are shown in FIG. 7a. The 12 tumor samples are labeled 1 to 12, left to right. There is a marker lane between samples 7 and 8. SKBR3 cell lysate was used as a positive control (right lane). The presence of significant amounts of p95 is seen in samples 1, 2, 3, 5, 7, 8 and 10; these tumors were designated p95-positive.

FFPE slides from all 12 tumors, along with 7 cell standards, were tested in the VeraTag assay outlined in FIG. 5, using clone D9.1, which has been shown to be p95-specific (see FIG. 6). The assay results from FFPE samples of clones designated by Western blot using fresh-frozen samples to be p95-positive or p95-negative are shown in FIG. 7b. The x-axis shows p95 positive or negative by Western blot; the y-axis shows Relative Peak Area multiplied by μl/cm$^2$, as set forth in Example 4. These results have been replotted to show the results for individual clones in FIG. 7c, alongside the results for the 7 cell standards. The Western-positive clones 1, 2, 3, 5, 7, 8 and 10 are shown on the left, followed by the Western-negative clones 4, 6, 9, 11 and 12, followed by the cell standards, which are as follows: MCF-7, MCF-7-p95, MCF-7-CTF, MCF-7-HER2, SKBR3, SKBR3-CTF and MDA-MB-453. The y-axis shows p95 levels in units of Relative Peak Area multiplied by μl/cm$^2$ (RPA*uL/sqcm), as set forth in Example 4. Especially considering the likely heterogeneity between the fresh frozen cells used for the Western blot and the FFPE samples used for the assay, there is a clear correlation between the two methods of quantifying p95.

FIGS. 8a-8c demonstrate the specificity of the D9.1 antibody as compared to its isotype control. Isotype control antibodies are used to show the non-specific binding of target primary antibodies to cell surface antigens. The isotype control antibody used in this experiment is IgG2a, matching the isotype of D9.1. The assay described in FIG. 5 was used to test both Western-positive and Western-negative FFPE tumor samples, along with 6 cell standards. In FIG. 8a, the Western-positive clones 1, 2, 3, 5, 7, 8 and 10 are shown on the left, followed by the Western-negative clones 4, 6, 9, 11 and 12, followed by the cell standards, which are as follows: MCF-7, MCF-7-p95, MCF-7-CTF, MCF-7-HER2, SKBR3 and SKBR3-CTF. In each sample, the binding to monoclonal antibody D9.1 is shown on the left, the binding to the isotype control antibody, IgG2a, is shown on the right. The y-axis shows p95 levels in Relative Peak Area multiplied by μl/cm$^2$ (RPA*uL/sqcm), as set forth in Example 4. In FIG. 8b (lower left panel), the results for Western-negative and Western-positive samples prior to subtracting non-specific binding are shown; in FIG. 8c (lower right panel), the results for Western-negative and Western-positive samples are shown after the non-specific isotype binding has been subtracted. The x-axis shows p95 negative or positive by Western blot; the y-axis shows p95 levels in Relative Peak Area multiplied by μl/cm$^2$ (RPA*uL/sqcm), as set forth in Example 4. The difference in the means between p95-positive and p95-negative clones is about 4-fold with a dynamic range of approximately 10-fold.

Figure 9A:
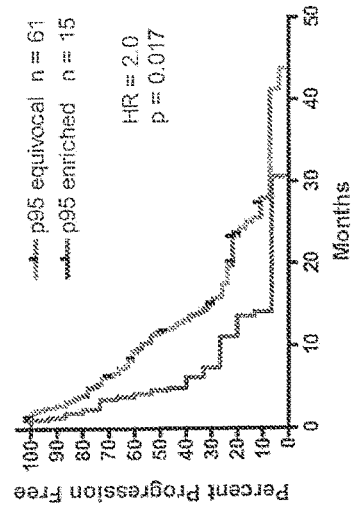

FIGS. 9a-9d show data demonstrating that p95-positive tumors are more likely to be highly HER2-positive, as shown by the VeraTag HER2-total (H2T) assay. The tumor samples described in FIGS. 7 and 8 were tested in the H2T assay (Cohort A). The data are shown in FIG. 9a. The tumors spanned the range of the HER2 positivity, but the mean score of samples deemed p95-positive by Western blot data were significantly higher than the p95-negatives (see, the Mann-Whitney test as set forth in Conover, W. J. (1980), Practical Nonparametric statistics (3$^{rd}$ Ed.)).

Figure 9C:
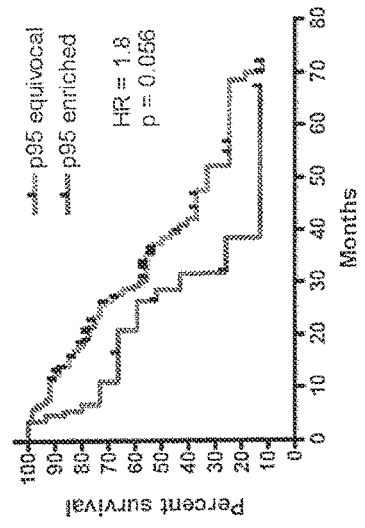
Figure 9B:
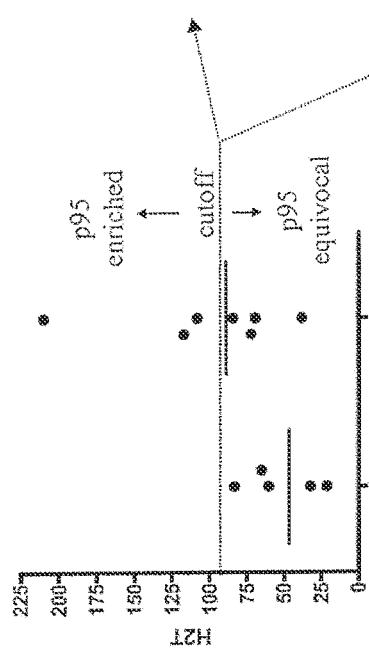
Figure 9D:
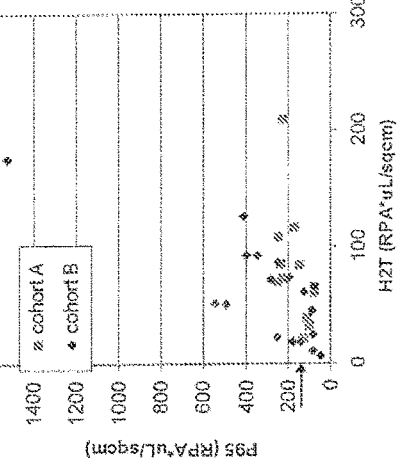

A second set of 18 FFPE tumor samples (Cohort B, diamonds) was tested using both the p95 assay as well as the H2T assay. FIG. 9b shows the correlative results. Cohort A (squares) corresponds to the tumor set measured in FIG. 7c. The approximate cutoff for Western positivity inferred from FIG. 7b is shown by the arrow on the y-axis in FIG. 9b. In general, a higher p95 signal is more likely to be found associated with a high H2T signal in both cohorts.

A large cohort of trastuzumab-treated patients whose tumors had previously been assessed for H2T were investigated to determine if there was any correlation between poor outcomes and samples in the high HER2 range theoretically enriched for p95. This cohort was derived from the International Serum Her2/neu Study Group (ISHSG) and is called the Lipton cohort. These patients were selected primarily by IHC performed at a central location—the University of Vienna in Austria—by a single pathologist. 90% of the patients were IHC3+, and 80/92 received trastuzumab in combination with chemotherapy while 12 received trastuzumab as a single drug. 88/92 patient had metastatic breast cancer and they could have received trastuzumab either as a first, second or third line therapy. For the high HER2 range, a cut-off value of $\log_{10}(H2T) \geq 1.95$ was established just above the highest p95-negative sample (the cut-off is shown in FIG. 9a). Above this H2T cutoff, tumors could be described as p95-enriched while those below the cutoff would be p95-equivocal. Among those patients confirmed to be HER2-FISH-positive, those in the p95-enriched group had significantly shorter time-to-progression (shown in FIG. 9c) and overall survival (shown in FIG. 9d) than those that were in the p95-equivocal group.

Figure 10A:
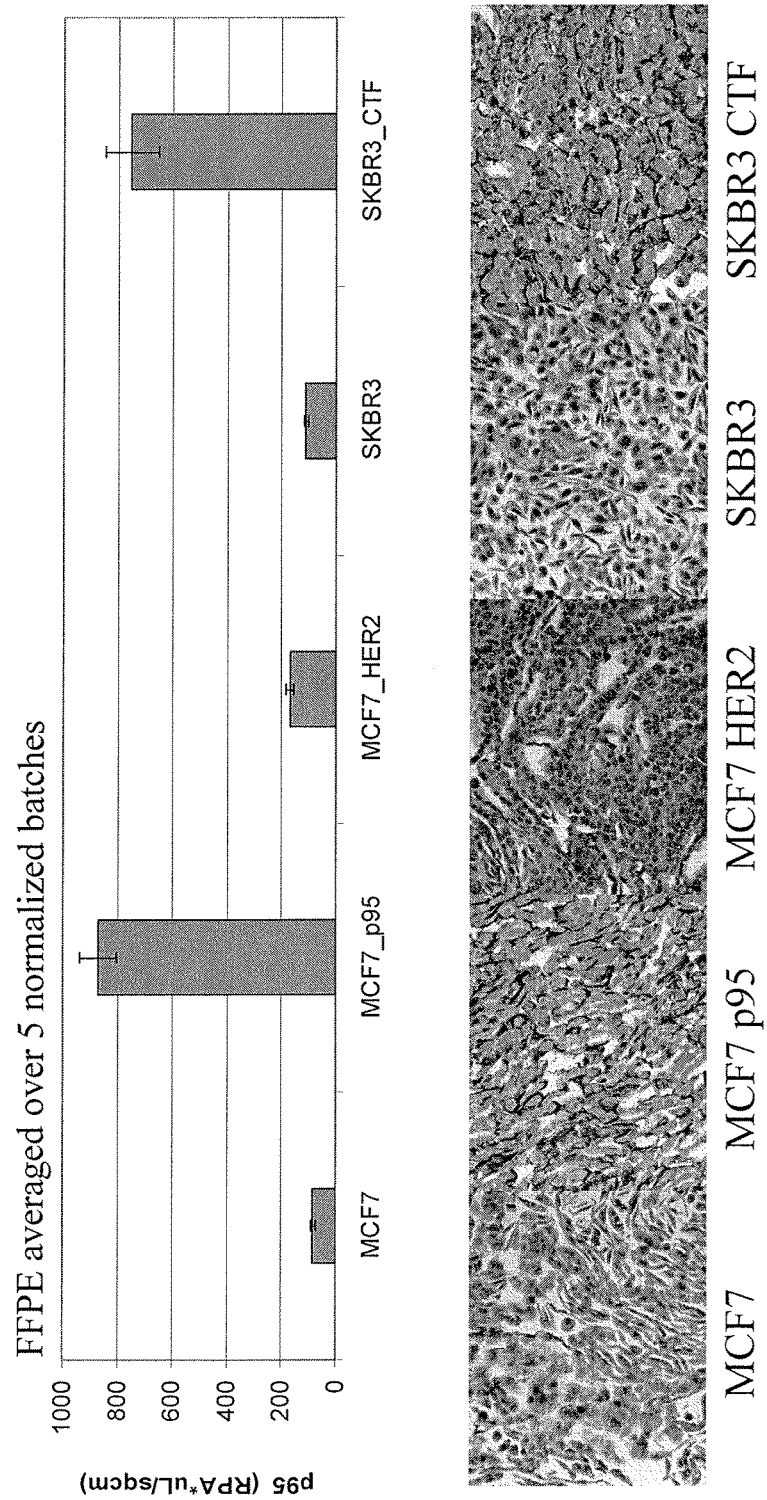
Figure 10B:
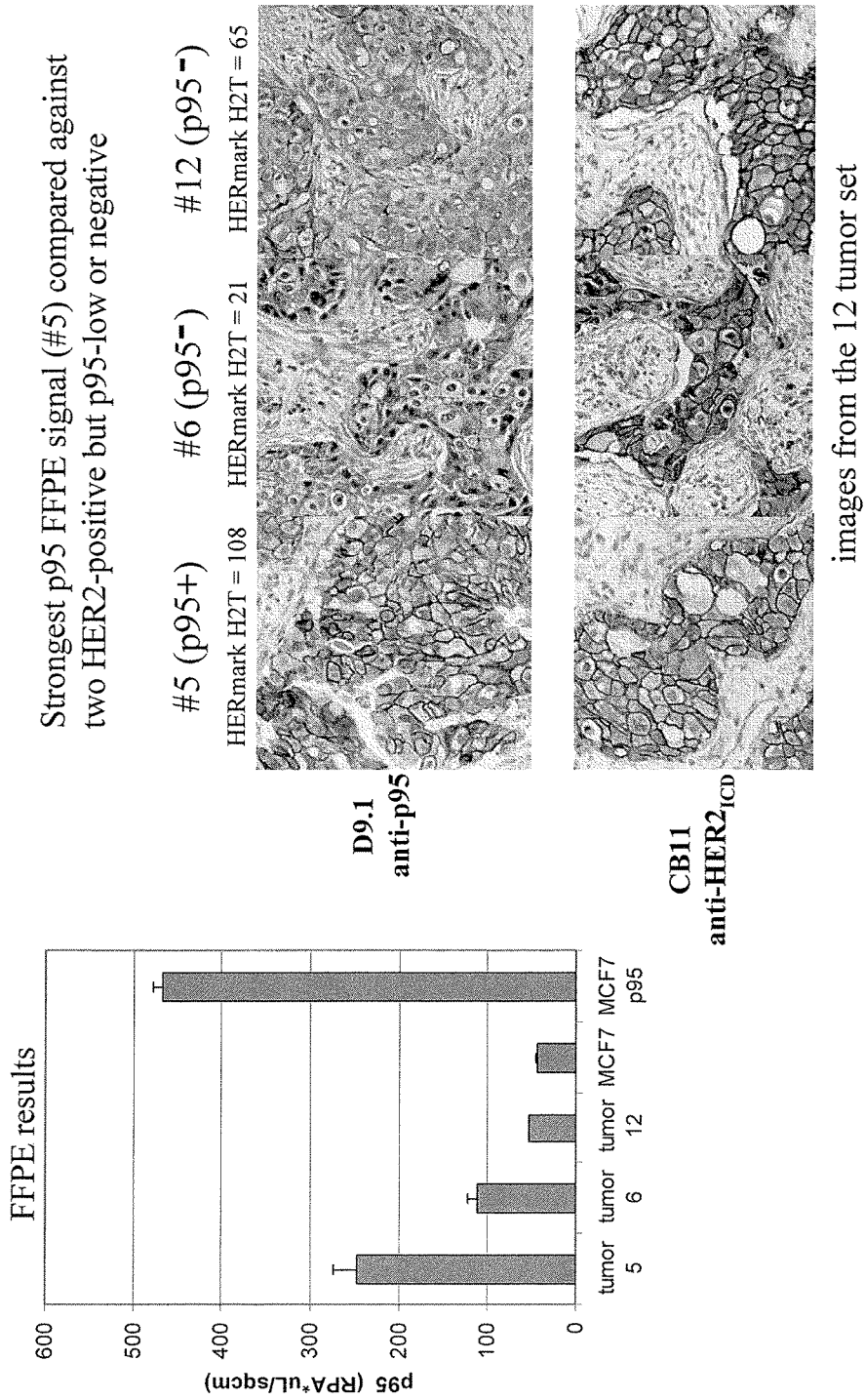

FIGS. 10a and 10b show colorimetric immunohistochemistry (IHC) of FFPE cell lines and tumor samples that are positive or negative for p95. In FIG. 10a, both assay data (top panel) for p95 levels (expressed in RPA*uL/sqcm) and IHC data (bottom panel) of FFPE cell lines probed with D9.1 are shown. The cell lines shown are MCF7, MCF7 transfected with either p95 or full-length Her2, SKBR3 and SKBR3 transfected with CTF, the C-terminal fragment of HER2 that is found in both the nucleus and cytoplasm. MCF7 is known to express little Her2, while the SKBR3 parental cell line is known to express high amounts of full-length HER2 and low levels of p95. MCF7 and SKBR3 cells stained with D9.1 show little staining, consistent with the low level of p95. MCF7-p95 cells stained with D9.1 show staining localized primarily to the cell membrane, consistent with the location of the p95. The IgG2a control isotype antibody showed no cell membrane staining, demonstrating the specificity of the D9 antibody (data not shown). The results of the IHC are consistent with the results seen using the VeraTag assay.

FIG. 10b shows both assay and IHC data for FFPE tumor samples. In the left panel, p95 assay data is shown for three tumor samples (#s 5, 6 and 12), as well as two cell lines (MCF7 and MCF7 transfected with p95). The units for the p95 levels are expressed as RPA*uL/sqcm). In the right panel, IHC data is shown for FFPE samples probed with either D9.1, a p95-specific antibody (top panels) or CB11, an antibody targeted to the intracellular domain of HER2 (bottom panels). All three tumors show staining with the CB11 antibody, consistent with the presence of full-length HER2, while only tumor 5, shown in both Western blots and the VeraTag assay to be p95-positive, stains with D9.1. These data further suggest that the epitope recognized by the D9.1 antibody is found in naturally-occurring forms of p95 found in breast tumor tissue.

FIG. 11 shows the results of quantitation studies of p95 using anti-p95 antibodies labeled directly with molecular tags. The experiment was performed as outlined in FIG. 5, except that the antibodies were labeled directly with molecular tags rather than using a secondary anti-mouse antibody.

The purified monoclonal antibodies used in these studies were D4.1, D8.2, D9.1 and D12.1 as shown on the x-axis; the y-axis is shown in Relative Peak Area multiplied by μl/cm$^2$, as set forth in Example 4. The anti-HER2 antibody Ab8 was used as a positive control. The cell lines tested were, from top to bottom in the legend and from left to right in the bar graph, MCF-7, MCF-7-CTF, MCF-7-her2, MCF-7-p95, SKBR3 and SKBR3-CTF. The results shown are very similar to those shown in FIG. 6, except for a reduction in the dynamic range between the p95-high-expressing cell lines (MCF-7-CTF, MCF-7-p95 and SKBR3-CTF) and the p95-low-expressing cell lines (MCF-7, MCF-7-Her2 and SKBR3).

Figure 12A:
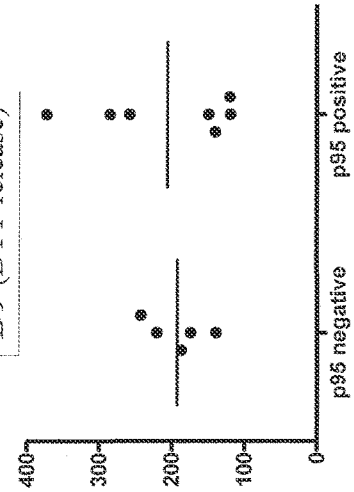
Figure 12B:
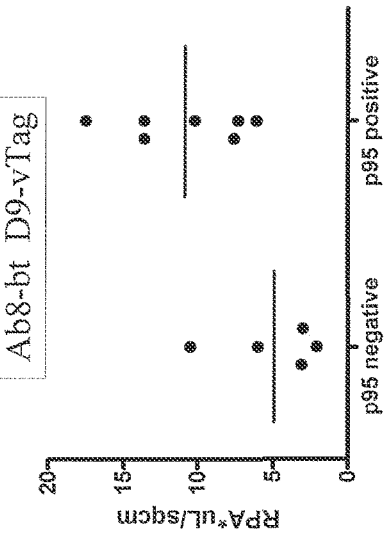

FIGS. 12a-12d show two sets of results using the D9.1 antibody to measure p95 levels in cell line standards and tumors, left and right, respectively. In FIGS. 12a and 12b, D9.1 is labeled with VeraTag to quantitate p95 in cell line standards (FIG. 12a) and tumor samples from Cohort A (FIG. 12b) using a single antibody assay. The cell line standards tested are, from left to right on the x-axis as shown in FIG. 12a, MCF-7, MCF-7-p95, MCF-7-CTF, MCF-7-HER2, SKBR3, SKBR3-CTF and MDA-MB-453. The y-axis shows p95 levels in Relative Peak Area multiplied by μl/cm$^2$, as set forth in Example 4. In FIG. 12b, the results of the single antibody assay are shown for tumor samples from Cohort A, which have been classified as p95-positive or p95-negative based on Western blot data. The x-axis shows p95 negative or p95 positive cell lines; the y-axis shows p95 levels in Relative Peak Area multiplied by μl/cm$^2$.

Figure 12C:
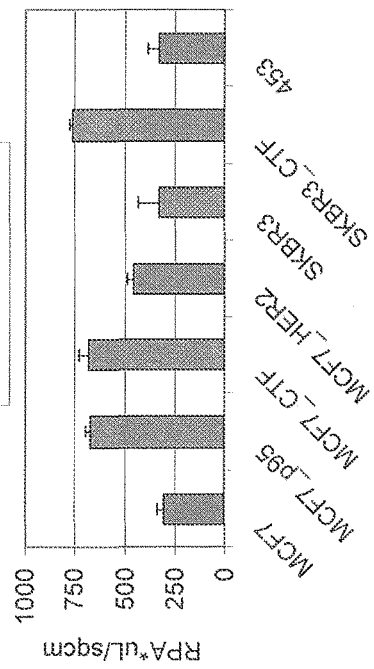
Figure 12D:
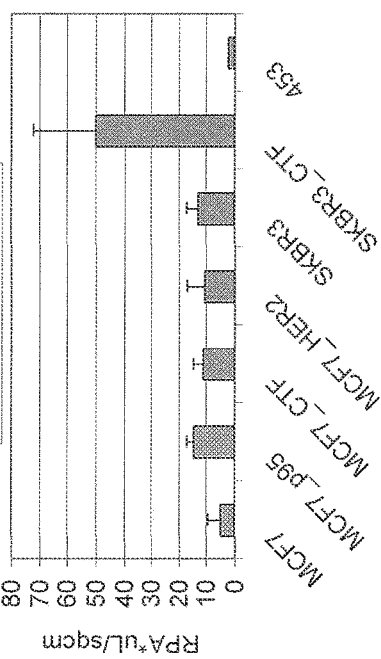

FIGS. 12c and 12d show the same cell line standards and tumor samples tested using a two antibody assay system in which both D9.1, which is p95-specific, and Ab8, which is specific for the intracellular domain of HER2, are used to detect p95. The Ab8 antibody is labeled with biotin; the D9.1 antibody has a cleavable VeraTag, allowing for a proximity assay in which the presence of the two antibodies within the distance of the same p95 molecule causes the release of the fluorophor on the VeraTag. As the data show, separation of p95-negative and p95-positive subgroups are retained with this form of the assay. The x-axis shows p95 negative or p95 positive cell lines; the y-axis shows p95 levels in Relative Peak Area multiplied by μl/cm$^2$.

Figure 13:
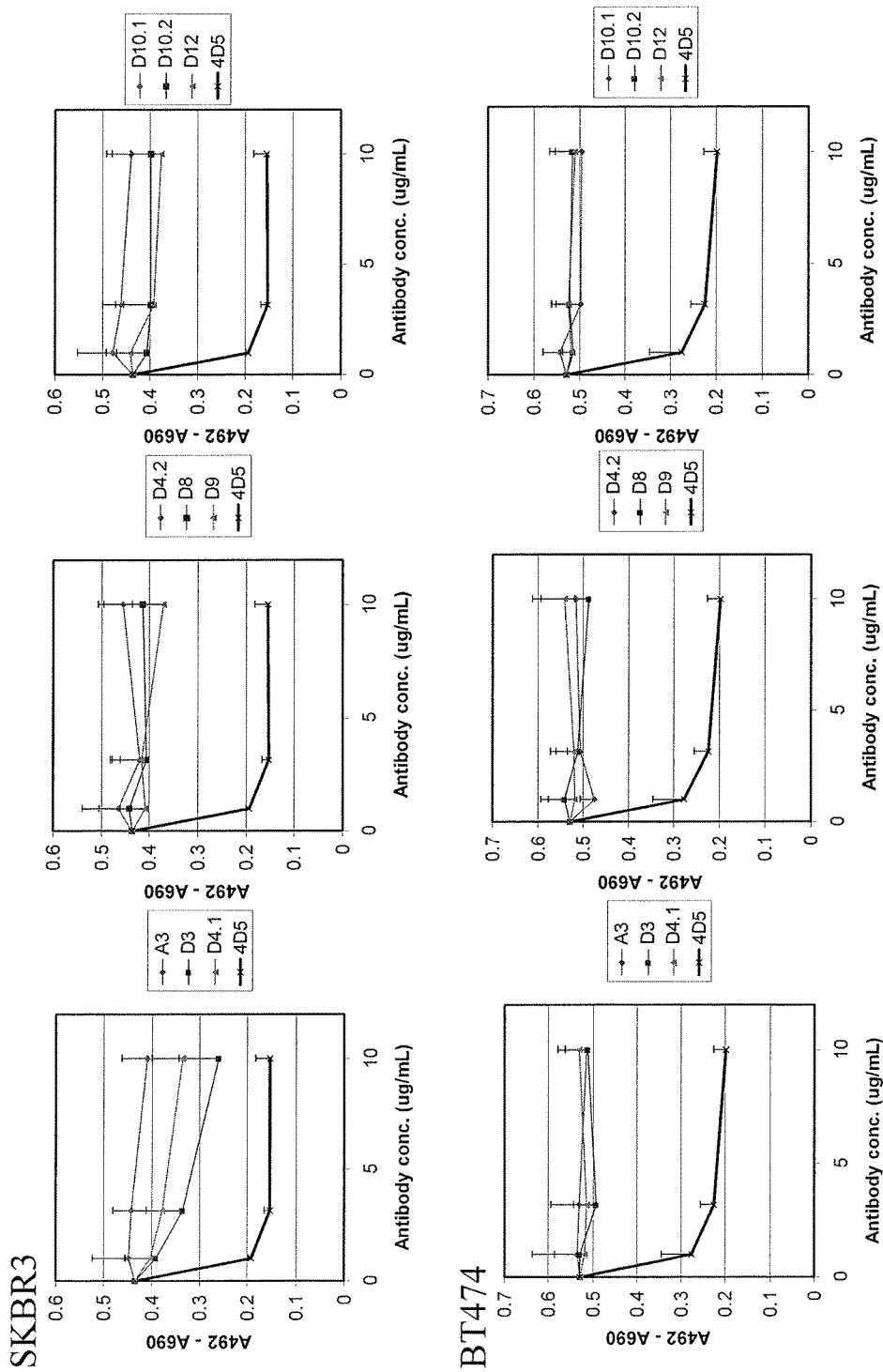

FIG. 13 shows the growth inhibition of breast cancer cell line SKBR3 and BT474 using anti-p95 antibodies compared to 4D5, the mouse version of trastuzumab. Several monoclonal antibodies generated from mice challenged with the D peptide from p95 were tested for their ability to inhibit growth in SKBR3 and BT474 cells, both of which are known to express high levels of HER2. 4D5 was used as a positive control. An antibody (A3) to an unrelated peptide was used as a negative control. The top 3 panels show results for SKBR3 cells; the bottom 3 panels show results for BT474 cells. The x-axis shows antibody concentration; the y-axis shows the difference in absorbance at 492 nM and 690 nM. In this experiment, cells were grown for 3 days in the presence of an antibody, then growth was assessed using the XTT assay. The results suggest that D3.4 and D4.1 inhibit the growth of SKBR3 cells but not BT474 cells.

Figure 14:
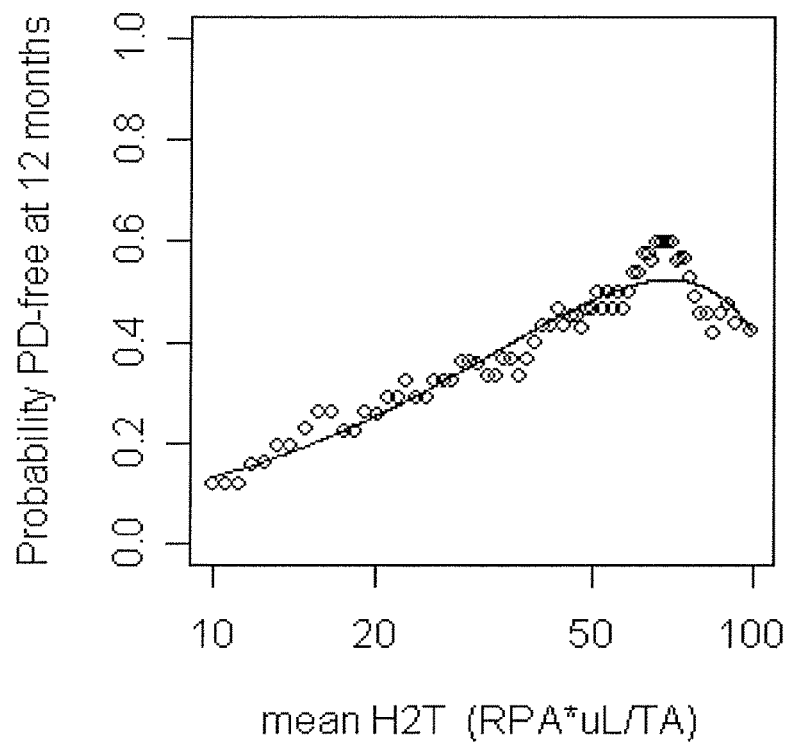

FIG. 14 shows a sub-population treatment effect pattern plot (STEPP), generated to examine the progression-free survival (PFS) rate at 12 months after treatment with trastuzumab across the distribution of H2T. Bins of 30 patients were ordered smallest to largest H2T. A trend of increasing probability of remaining progression-free past 12 months was observed for increasing H2T. However, at the highest levels of H2T, an abrupt decrease in the PFS rate was observed, consistent with a reduction in susceptibility to trastuzumab.

Figure 15:
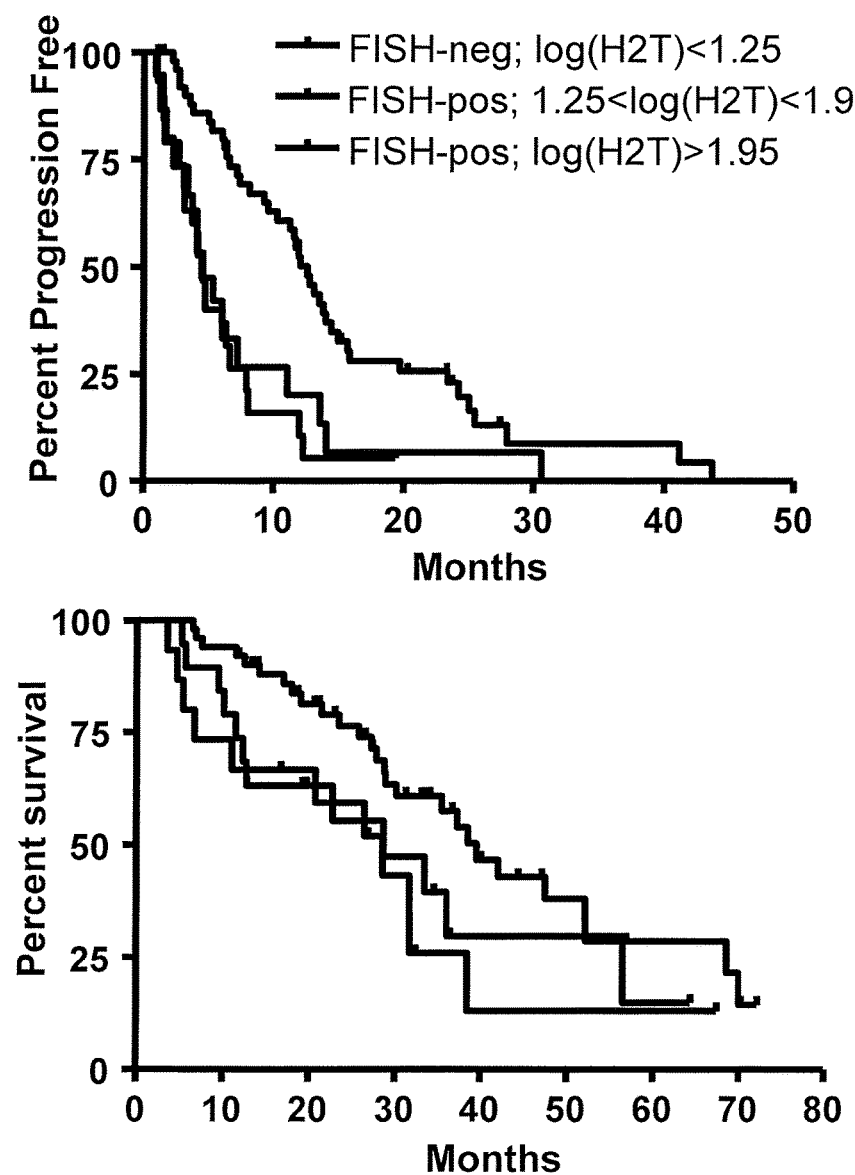

FIG. 15 shows a Kaplan-Meier (KM) analyses comparing the PFS of FISH(−), H2T low ($\log_{10}$H2T<1.25) patients with those of FISH(+), H2T high ($\log_{10}$H2T≥1.95 and FISH(+), H2T intermediate (1.25<$\log_{10}$H2T<1.95). Cut-offs were identified by lowest p-value in a positional scanning analysis. KM analyses demonstrated that patients who were FISH(+), H2T intermediate had a significantly longer PFS than patients who were FISH(−), H2T low (median PFS 12.6 vs. 4.5 months; hazard ratio (HR)=0.34; p<0.0001). Patients that were FISH(+), H2T high experienced a PFS that was no better than patients that were FISH(−), H2T low (median PFS 4.6 vs. 4.5 months; HR=0.87; p=0.68).

Figure 16:
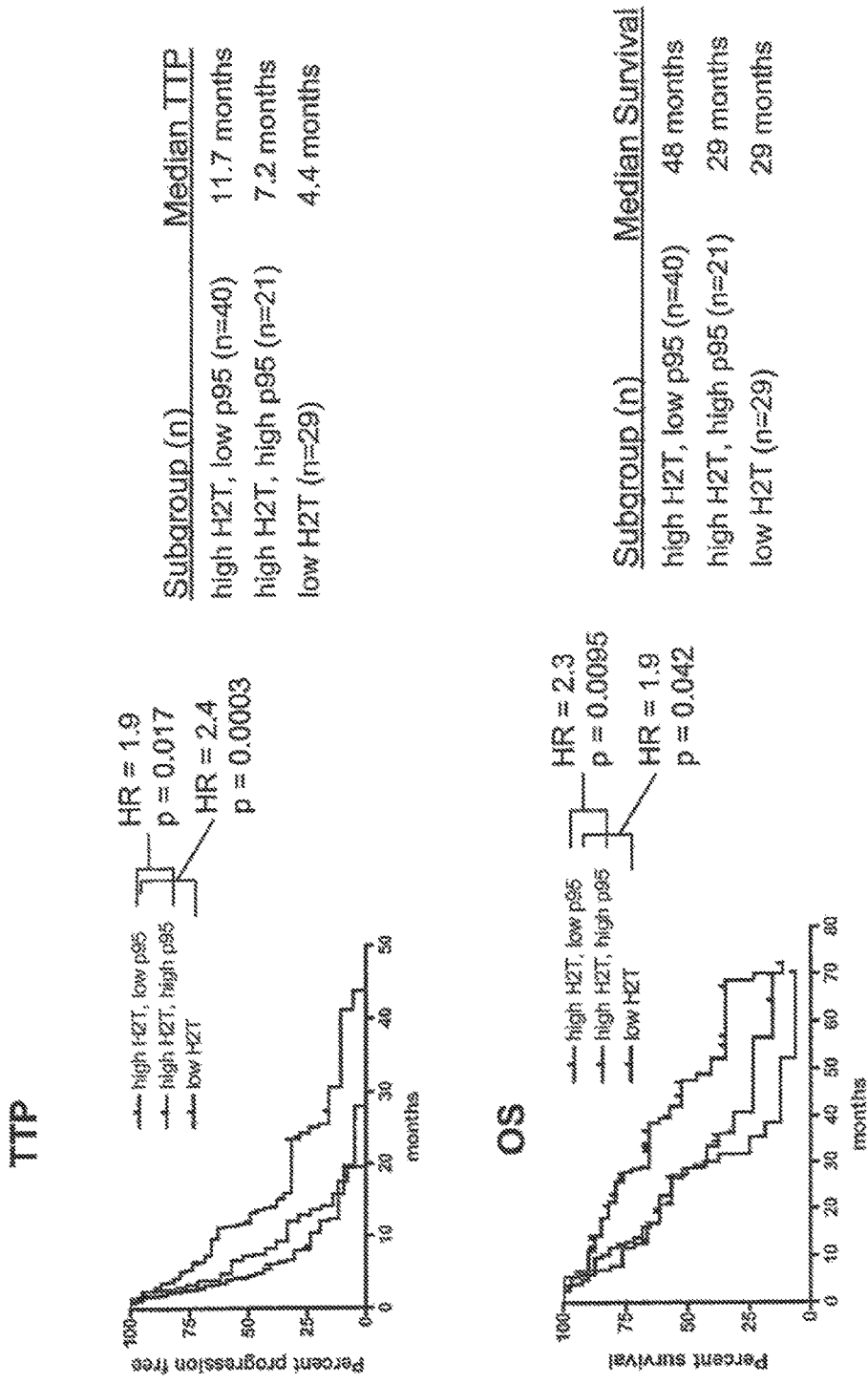

FIG. 16 shows the discrimination of patient populations by H2T and p95 (N=90). Previous analyses of this cohort using VeraTag measures of HER2 protein expression (H2T) identified an H2T-high subgroup with longer TTP than the H2T-low subgroup. A Cut-off for p95 was identified by lowest p-value in a positional scanning analysis This Figure shows Kaplan-Meier (KM) analyses comparing the % progression free (TTP) of H2T low (log 10H2T<1.25) patients with those of H2T high (Log 10H2T≥1.25 or linear >13.8) and low p95 (log 10H2T<90) with patients with high H2T (Log 10H2T≥1.25) and high p95 (log 10H2T>90).

KM analyses demonstrated that patients who were H2T low had a significantly shorter median TTP (in response to trastuzumab) than patients with High H2T, low 95 (median TTP 4.4 vs. 11.7; hazard ratio (HR)=2.4; p=0.0003). Patients that were high H2T, high p95 also experienced a significantly shorter median TTP compared with patients with High H2T/low p95 (median TTP 7.2 vs 11.7 months; hazard ratio (HR)=1.9, p=0.017). Similar results were seen with overall survival, such that KM analyses for OS demonstrated that patients who were H2T low had a significantly shorter median OS (in response to trastuzumab) than patients with High H2T, low 95 (median OS 29 vs. 48 months; hazard ratio (HR)=1.9; p=0.042). Patients that were high H2T, high p95 also experienced a significantly shorter median OS compared with patients with High H2T/low p95 (median OS 29 months vs 48 months; hazard ratio (HR)= 2.3, p=0.0095).

Figure 17:
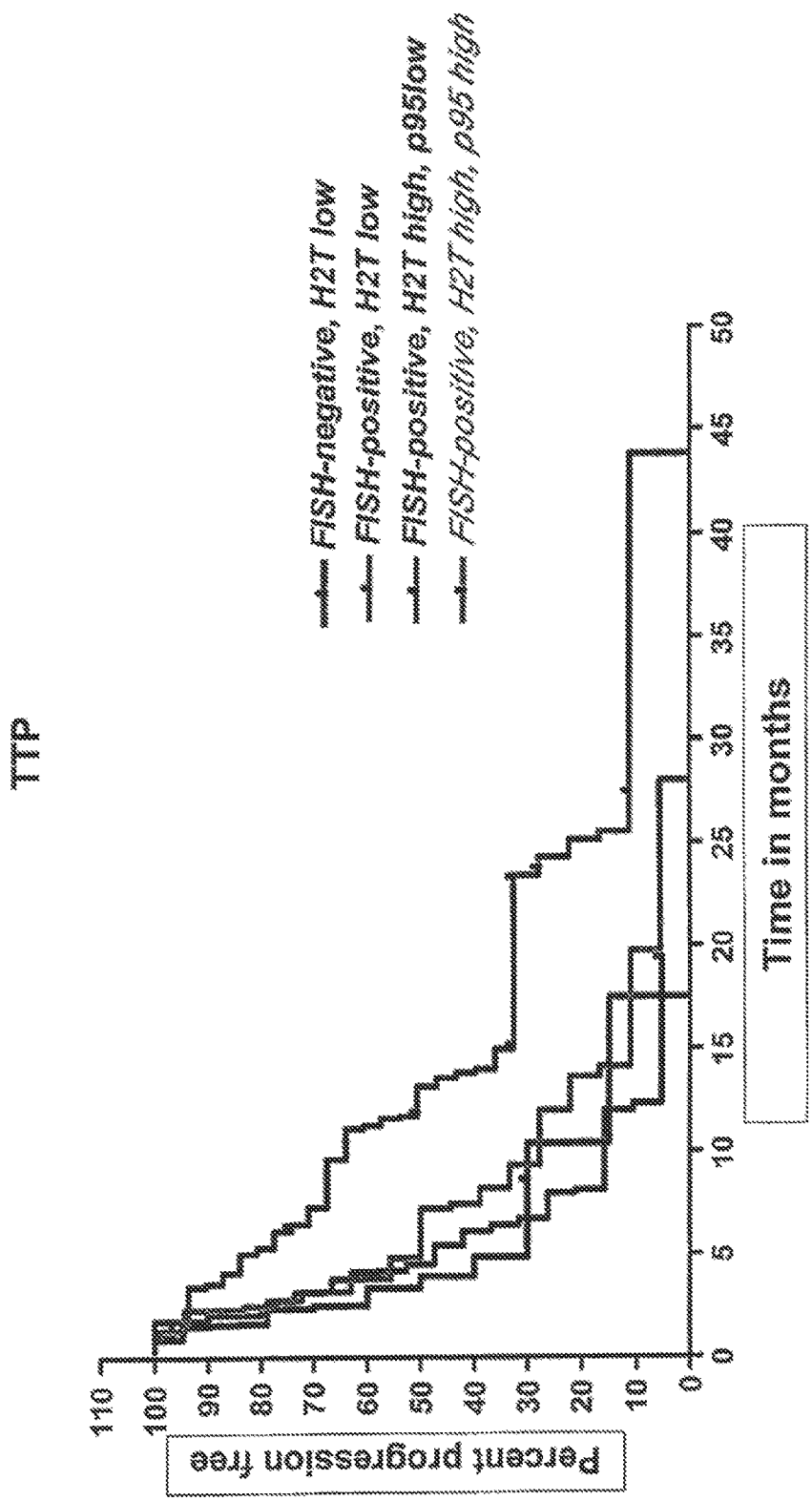

FIG. 17 shows Kaplan-Meier (KM) analyses comparing the percent progression free (time to progression, TTP) of various subgroups from the Lipton cohort, as defined by VeraTag measurements of HER2 total (H2T high or low), and p95HER2 (p95 high or low). Cut-offs were identified by lowest p-value in a positional scanning analysis. H2T high= (log 10H2T>1.25 or on a linear scale, >13.8). Low H2T=log 10H2T<=1.25 or on a linear scale, <=13.8. p95 low=p95<=90 and p95 high=p95>90 (on a linear scale).

KM analyses demonstrated that patients who were FISH positive, H2T high, p95 low (green line) had a (significantly) longer median TTP than patients who were FISH negative, H2T low (red line). Patients that were FISH-positive, H2T low (blue line) experienced a PFS that was superimposable (i.e., no better) than patients that were FISH negative, H2T low (red line). In addition, patients that were FISH positive, H2T high, and p95 high (orange line) experienced PFS that was again, nearly superimposable on the other 2 less-favored groups indicated by the red and blue lines (FISH negative, H2T low and FISH positive, H2Tlow, respectively). The group with the best outcomes in this study was the group in green, who were FISH positive, H2T high, and p95 low.

DETAILED DESCRIPTION OF THE INVENTION

"Antibody" means an immunoglobulin that binds to, and is thereby defined as complementary with, a particular spatial and polar organization of another molecule. The antibody can be monoclonal, polyclonal or recombinant and can be prepared by techniques that are well known in the art such as immunization of a host and collection of sera (polyclonal) or by preparing continuous hybrid cell lines and collecting the secreted protein (monoclonal) or by cloning and expressing nucleotide sequences or mutagenized versions thereof coding at least for the amino acid sequences required for binding. Antibodies may include a complete immunoglobulin or fragment thereof, which immunoglobulins include the various classes and isotypes, such as IgA, IgD, IgE, IgG1, IgG2a, IgG2b and IgG3, IgM, etc. Fragments thereof may include Fab, Fv and F(ab')2, Fab' and the like. Antibodies may also be single-chain antibodies, chimeric antibodies, humanized antibodies or any other antibody derivative known to one of skill in the art that retains binding activity that is specific for a particular binding site. In addition, aggregates, polymers and conjugates of immunoglobulins or their fragments can be used where appropriate so long as binding affinity for a particular binding site is maintained. Guidance in the production and selection of antibodies and antibody derivatives for use in immunoassays, including such assays employing releasable molecular tags (as described below) can be found in readily available texts and manuals, e.g., Harlow and Lane, 1988, *Antibodies: A Laboratory Manual*, Cold Spring Harbor Laboratory Press, New York; Howard and Bethell, 2001, *Basic Methods in Antibody Production and Characterization*, CRC Press; Wild, ed., 1994, *The Immunoassay Handbook*, Stockton Press, New York.

"Binding compound" shall refer to a molecule capable of binding to another molecule of interest. A binding compound may be an antibody, a peptide, a peptide or non-peptide ligand for a cell surface receptor, a protein, an oligonucleotide, an oligonucleotide analog, such as a peptide nucleic acid, a lectin or any other molecular entity that is capable of specifically binding to a target molecule or complex. In one embodiment, the target molecule is a protein or protein complex. In another embodiment, a binding compound further comprises a proximity probe. In one embodiment, a binding compound comprises one or more molecular tags attached to a binding moiety. In another embodiment, a second binding compound may be bound to the binding compound and measured or quantified as a correlative for the presence of the binding compound, which is bound to the target protein. As another specific example, either the first or second binding compound may generate molecule that acts in conjunction with a proximity probe with an effective proximity, producing a signal that correlates with the presence of the target protein. Further, in another embodiment, binding compounds may have molecular tags that interact with one another within an effective proximity to form a complex that generates a signal or can be detected and measured in a manner that correlates with the presence of the target protein. More specifically, the target protein or complex may be p95 or a p95 complex.

"Binding moiety" means any molecule to which molecular tags can be directly or indirectly attached that is capable of binding to an analyte. Binding moieties include, but are not limited to, antibodies, peptides, proteins, nucleic acids and organic molecules having a molecular weight of up to about 1000 Daltons and containing atoms selected from the group consisting of hydrogen, carbon, oxygen, nitrogen, sulfur and phosphorus. Preferably, binding moieties are antibodies.

"Cell lines" refers to cells that have been separated from their original tissue, clonally multiplied and/or maintained in culture. As specific examples, cell lines may be derived from each type of cancer and multiple different cell lines may be derived from samples of the same type of cancer. Examples of different types of cell lines include, but are not limited to, breast cancer cell lines, such as MCF-7, MDA-MB-231, SK-BR-3, T-47D and ZR-75-1.

"Chemotherapeutic agent" means a chemical substance that is used to treat a condition, particularly cancer.

A "cleavable linkage," as used herein, refers to a chemical linking group that may be cleaved to release a detectable molecular tag connected to a binding moiety with the cleavable linkage.

A "cleavage-inducing moiety," or "cleaving agent," as used herein, is a group that produces an active species that is capable of cleaving a cleavable linkage. Preferably, the active species is a chemical species that exhibits short-lived activity so that its cleavage-inducing effects are only in the proximity of the site of its generation.

A "cleaving probe," as used herein, refers to a reagent that comprises a cleavage-inducing moiety, as defined herein, and a binding compound such as an antibody, a peptide, a peptide or non-peptide ligand for a cell surface receptor, a protein, such as streptavidin, a small molecule, such as biotin, an oligonucleotide, an oligonucleotide analog, such as a peptide nucleic acid, a lectin or any other molecular entity that is capable of binding to a target protein or molecule or stable molecular complex.

"Effective proximity," as used herein, describes the distance between two binding compounds that is sufficient to generate a detectable signal, indicating the presence of the target molecule. For example, a proximity probe and a binding compound that are bound on p95 (or with another analyte of interest) within an effective proximity will generate a detectable signal, indicating and/or quantifying the presence of p95 and/or a p95 complex. Preferably, the effective proximity range for many detection systems is less than 400 nM, preferably less than 300 nM, preferably less than 200 nM, preferably less than 100 nM, preferably, less than 50 nM.

"Epitope" refers to a site on the surface of a molecule, usually a protein, to which an antibody molecule or other binding compound binds. Generally, a protein has several or many different epitopes, also called antigenic determinants, and reacts with antibodies of different specificities. A preferred antigenic determinant is a phosphorylation site of a protein. Preferred antigenic determinants are cryptic epitopes found in the amino acid sequence of Her2 that are not accessible for binding (e.g., by binding compounds) in the full length molecule but rather are revealed and accessible for binding in the truncated p95 version of Her2.

"Exosome" refers to a membrane vesicle that has been released from a cell membrane into an extracellular environment. Exosomes and other membrane vesicles contain membrane-bound moieties, such as proteins, and they may be used, for example, in assays to detect these moieties, such as p95.

"Extracellular domain" refers to a portion of a molecule that lies outside the membrane of a cell. An example of an extracellular domain, without limitation, would be the portion of a trans-membrane protein that lies outside the cell. More specifically, an example would be the extracellular domain of HER-2, which can be cleaved to generate a shed ecto-domain and a truncated membrane-bound p95 protein.

"FFPE" shall refer to a formalin-fixed paraffin-embedded sample or samples. Such samples are typically, for example, without limitation, used in an assay for proteins and receptor complexes in the form of thin sections, e.g. 3-10 µm thick, of fixed tissue mounted on a microscope slide or equivalent surface. Such samples also typically undergo a conventional re-hydration procedure, and optionally, an antigen retrieval procedure as a part of, or preliminary to, assay measurements.

"Her-2", "ErbB2", "c-Erb-B2", "HER2", "Her2" and "neu" are used interchangeably herein and refer to native Her-2, and allelic variants thereof, as described, for example, in Semba et al., 1985, *P.N.A.S. USA* 82:6497-650 and Yamamoto et al., 1986, *Nature* 319:230-234 and Genbank accession number X03363. Unless indicated otherwise, the terms "Her-2", "ErbB2", "c-Erb-B2", "HER2" and "Her2" when used herein refer to the human protein. The gene encoding Her2 is referred to herein as "erbB2."

"Her-2-acting agent," as used herein, refers to a compound that can inhibit a biological activity of Her-2 or a Her-2 expressing cell or a Her-2 positive cancer cell. Such biological activities include, but are not limited to, dimerization, autophosphorylation, phosphorylation of another receptor, signal transduction and the like. Biological activities can include, without limitation, cell survival and cell proliferation and inhibition of such activities by a Her-2 acting agent could be direct or indirect cell killing (eg, ADCC), disruption of protein complexes or complex formation, modulation of protein trafficking or enzyme inhibition. Biological activities can also include patient response as set forth in this application. Exemplary Her-2-acting agents include, but are not limited to BIBW 2992, HKI-272, 4D5, pertuzumab, trastuzumab, Herceptin-DM-1, AEE-788 and lapatinib.

"High" refers to a measure that is greater than a standard such as a predetermined measure or a subgroup measure or that is relatively greater than another subgroup measure. For example, high Her-2 or p95 may refer to a measure that is equal to or greater than a predetermined cutoff. High Her-2 or p95 may also refer to a measure of Her-2 or p95 wherein a high Her-2 or p95 subgroup has relatively greater levels of Her-2 or p95 than another subgroup. For example, without limitation, according to the present specification, two distinct patient subgroups can be created by dividing samples around a mathematically determined point, such as, without limitation, a median, thus creating a subgroup whose measure is high (i.e., higher than the median) and another subgroup whose measure is low. Her-2 or p95 can be measured by any method known to one skilled in the art such as, for example, without limitation, using VeraTag or using any standard immunohistochemical (IHC) method such as HercepTest®.

"Likely to," as used herein, refers to an increased probability that an item, object, thing or person will occur. Thus, in one example, a subject that is likely to respond to treatment with trastuzumab has an increased probability of responding to treatment with trastuzumab relative to a reference subject or group of subjects.

"Long," as used herein, refers to a time measure that is greater than a predetermined measure or a subgroup measure that is relatively longer than another subgroup measure. For example, with respect to a patient's longevity, a long time progression refers to time progression that is longer than expected. Whether a time progression is long or not may be determined according to any method available to one skilled in the art.

"Low" is a term that refers to a measure that is less than a standard such as a predetermined measure or a subgroup measure that is relatively less than another subgroup measure. For example, low Her-2 or p95 may mean a method that is less than a predetermined measure, such as a predetermined cutoff. Low Her-2 or p95 may also mean a measure wherein a low Her-2 or p95 subgroup is relatively lower than another subgroup. For example, without limitation, according to the present specification, two distinct patient subgroups can be created by dividing samples around a mathematically determined point, such as, without limitation, a median, thus creating a group whose measure is low (i.e., less than the median) with respect to another group whose measure is high (i.e., greater than the median). Her-2 or p95 can be measured by any method known to one skilled in the art such as, for example, without limitation, using the VeraTag method or using any standard immunohistochemical (IHC) method such as HercepTest®.

A "molecular tag," as used herein, refers to a molecule that can be measured directly or indirectly, can be distinguished from other molecules based on one or more physical, chemical or optical differences among the molecules being separated, including but not limited to, electrophoretic mobility, molecular weight, shape, solubility, pKa, hydrophobicity, charge, charge/mass ratio, polarity or the like. In one embodiment, molecular tags in a plurality or set differ in electrophoretic mobility and optical detection characteristics and can be separated by electrophoresis. In another embodiment, molecular tags in a plurality or set may differ in molecular weight, shape, solubility, pKa, hydrophobicity, charge, polarity and can be separated by normal phase or reverse phase HPLC, ion exchange HPLC, capillary electrochromatography, mass spectroscopy, gas phase chromatography or a like technique.

Measurement of molecular tags may also involve using secondary molecular interactions, with or without further modification, to detect, enhance or amplify a measurable signal that acts as a correlative for the presence and/or quantity of an analyte, such as p95 or a p95 complex. In one embodiment, a set of two or more molecular tags may interact within an effective proximity to produce a measurable signal. As molecular tags, a measurable signal may be generated, for example, by detection of two complementary nucleic acid sequences which will hybridize when the complementary sequences are within an effective proximity. Other examples that either generate a measurable signal or that can be measured using detection methods know in the art include, but are not limited to, FRET, BRET, BiFC, LCI and QPCR.

"Optimal cutoff" as used herein, refers to the value of a predetermined measure on subjects exhibiting certain attributes that allow the best discrimination between two or more categories of an attribute. For example, an optimal cutoff that allows one to best discriminate between two categories such as high p95 expression and low p95 expression for determining overall survival would be useful. Optimal cutoffs may be used to separate the subjects with values lower than or higher than the optimal cutoff to optimize the prediction model.

"Overall survival" or "OS" refers to a time as measured from the start of treatment to death or censor. Censoring may come from a study end or change in treatment. Overall survival can refer to a probability as, for example, a probability when represented in a Kaplan-Meier plot of being alive at a particular time, that time being the time between the start of the treatment to death or censor.

"p95" refers to an N-terminally truncated, C-terminal portion of HER-2. "p95" has also been referred to as "truncated ErbB2 receptor", "p95$^{ErbB2}$", "p95HER2", and more generally as "NH$_2$-terminally truncated HER-2/neu" and "HER2 C-terminal fragments" to reflect the fact that "p95" represents a family of truncated HER2 proteins similar, but not identical in size to that originally identified as having an apparent molecular weight of 95 kiloDaltons. p95 is thought to be produced by at least two distinct mechanisms. p95 may result from the proteolytic cleavage of full-length HER-2. p95 may also result from an alternative translational start downstream from the canonical first methionine including but not limited to M611 and M687

"p95 complex" refers to a complex of proteins at least one member of which is p95. Examples, without limitation, of possible p95 complexes include p95 homodimers, as well as heterodimers comprised of p95 and full-length Her2 and also other members of the epidermal growth factor receptor family including Her1, Her3 and Her4.

A "proximity probe," as used herein, refers to a reagent that comprises a moiety capable of acting within effective proximity to a molecular tag on a binding compound to generate a detectable signal and an antibody, a peptide, a peptide or non-peptide ligand for a cell surface receptor, a protein, such as streptavidin, a small molecule, such as biotin, an oligonucleotide, an oligonucleotide analog, such as a peptide nucleic acid, a lectin or any other molecular entity that is capable of specifically binding to a target protein or molecule or stable complex. For example, a proximity probe comprised of a p95-targeted antibody with a molecular tag may be capable of binding to p95 within an effective proximity to one or more p95 binding compounds, or a binding compound of another protein of interest, that has one or more molecular tags attached. In one embodiment, a proximity probe comprises a binding molecule and a first nucleic acid and a binding molecule comprises an antibody and a second nucleic acid, wherein the first and second nucleic acids are complementary to each other and each is a predetermined length so that when the nucleic acids are within an effective proximity of one another, they hybridize. Hybridization may be measured by any method known to one skilled in the art. For example, fluorophores may be attached to the nucleic acids as indicators of hybridization. In a preferred embodiment, hybridization is measured with a nucleic acid amplification method such as, for example, without limitation, the rolling circle amplification method (see, for example, Lizardi et al., (1998) *Nat Genet.* 19: 225-232).

"RECIST" shall mean "Response Evaluation Criteria in Solid Tumours" and is a set of published rules that define when cancer patients improve ("respond"), stay the same ("stable") or worsen ("progression") during treatments. Response as defined by RECIST criteria have been published, for example, at *Journal of the National Cancer Institute*, Vol. 92, No. 3, Feb. 2, 2000 and RECIST criteria may include other similar published definitions and rule sets.

"Respond" to treatment, and other forms of this verb, as used herein, refer to the reaction of a subject to treatment with an agent. As an example, a subject responds to treatment if growth of a tumor in the subject is retarded about 10%, 20%, 30%, 40%, 50%, 60%, 70%, 80%, 90% or more. In another example, a subject responds to treatment if a tumor in the subject shrinks by about 5%, 10%, 20%, 30%, 40%, 50% or more as determined by any appropriate measure, e.g., by mass or volume. In another example, a subject responds to treatment with a Her2-acting agent if the subject experiences a life expectancy extended by about 5%, 10%, 20%, 30%, 40%, 50% or more beyond the life expectancy predicted if no treatment is administered. In another example, a subject responds to treatment with an agent if the subject has an overall survival or increased time to progression. Several methods may be used to determine if a patient responds to a treatment including the RECIST criteria, as set forth herein.

"Sample" or "tissue sample" or "patient sample" or "patient cell or tissue sample" or "specimen" each refer to a collection of similar cells obtained from a tissue of a subject or patient. The source of the tissue sample may be solid tissue as from a fresh tissue, frozen and/or preserved organ or tissue or biopsy or aspirate; blood or any blood constituents, bodily fluids such as cerebral spinal fluid, amniotic fluid, peritoneal fluid or interstitial fluid or cells from any time in gestation or development of the subject. The tissue sample may contain compounds that are not naturally intermixed with the tissue in nature such as preservatives, anticoagulants, buffers, fixatives, nutrients, antibiotics or the like. Cells may be fixed in a conventional manner, such as in an FFPE manner.

"Short," as used herein, refers to a time measure that is shorter than a standard such as a predetermined measure or a subgroup measure that is relatively shorter than another subgroup measure. For example, with respect to a patient's longevity, a short time progression refers to time progression that is shorter than predicted. Whether a time progression is short or not may be determined according to any method available to one skilled in the art.

"Significant event," as used herein, shall refer to an event in a patient's disease that is important as determined by one skilled in the art. Examples of significant events include, for example, without limitation, primary diagnosis, death, recurrence, the determination that a patient's disease is metastatic, relapse of a patient's disease or the progression of a patient's disease from any one of the above noted stages to another. A significant event may be any important event used to assess OS, TTP and/or using the RECIST or other response criteria, as determined by one skilled in the art.

As used herein, the terms "subject" and "patient" are used interchangeably. As used herein, the terms "subject" and "subjects" refer to an animal, preferably a mammal including a non-primate (e.g., a cow, pig, horse, donkey, goat, camel, cat, dog, guinea pig, rat, mouse or sheep) and a primate (e.g., a monkey, such as a cynomolgus monkey, gorilla, chimpanzee or a human).

"Targeted therapy" refers to therapeutic treatment that attempts to identify and treat specific cells involved in disease without harming or altering normal cells. Targeted therapeutics may be comprised of, but not limited to, small molecules, such as lapatinib, imatinib (such as Iressa®) and gefitinib (GLEEVEC®), monoclonal antibodies, such as trastuzumab or nucleic acids, such as siRNAs used to block expression of gene products involved in disease processes. Targeted therapies are useful in the treatment of many disease processes, such as cancer. As used herein, "time course" shall refer to the amount of time between an initial event and a subsequent event. For example, with respect to a patient's cancer, time course may relate to a patient's disease and may be measured by gauging significant events in the course of the disease, wherein the first event may be diagnosis and the subsequent event may be metastasis, for example.

"Time to progression" or "TTP" refers to a time as measured from the start of the treatment to progression or a cancer or censor. Censoring may come from a study end or from a change in treatment. Time to progression can also be represented as a probability as, for example, in a Kaplan-Meier plot where time to progression may represent the probability of being progression free over a particular time, that time being the time between the start of the treatment to progression or censor.

"Treatment," and other forms of this word refer to the administration of an agent to impede a disease, such as the growth of a cancer, to cause a cancer to shrink by weight or volume, to extend the expected survival time of the subject and/or time to progression of the tumor or the like. Treatment may also refer to any course which one skilled, for example, a treating physician, deems expedient.

"Tumor lysate" refers to the solution produced when the cell membranes of tumors are disrupted, whether by physical or chemical methods. Tumor lysates typically contain representative components of the cell, including but not limited to, protein markers, enzymes, nucleic acids and complexes of proteins and other molecules that can subsequently be measured in various assays.

The term "VeraTag" refers to single and multiplexed and multi-label assays, materials, methods and techniques for performing and utilizing such assays, including but not limited to reagents, analytical procedures and software related to those assays. The terms VeraTag, vTag and eTag shall be used interchangeably.

In a first aspect, the invention is drawn to a method of measuring and/or quantifying the presence and/or amount of p95 or p95 complex in a sample, the method comprising providing a sample and determining the presence and/or quantity of p95 or p95 complex in the sample. In a preferred embodiment, the sample is a biological sample. In a preferred embodiment, the sample is a tissue sample. In a preferred embodiment, the sample is a fixed sample, a frozen sample or a lysate. In a preferred embodiment, the sample is a tumor sample. In a preferred embodiment, the sample is a frozen tumor tissue sample. In a preferred embodiment, the sample comprises a tumor lysate. In a preferred embodiment, the sample comprises a breast cancer sample. In a preferred embodiment, the sample is an FFPE sample. In a preferred embodiment, the sample is a blood, plasma or lymph sample. In a preferred embodiment, the blood or plasma sample contains circulating tumor cells. In a preferred embodiment, the sample contains exosomes and/or other vesicles. In a preferred embodiment, the sample comprises cell lines. In a preferred embodiment, the measurement may be quantitative across a wide dynamic range.

In a second aspect, the invention is drawn to a method of measuring and/or quantifying the presence and/or quantity of p95 in a sample, the method comprising mixing a sample with a binding compound and determining the presence and/or quantity of binding compound bound to p95. In a preferred embodiment, the binding compound is capable of specifically binding p95. In a preferred embodiment, the binding compound comprises an antibody. In a preferred embodiment, the antibody was raised against one of the peptides having SEQ ID NOs 1-7. In certain embodiments, the antibody is or comprises one of the antibodies produced by hybridoma cell lines deposited with the ATCC having accession number PTA-9738 (p95.D3.4), PTA-9739 (p95.D8.2) and PTA-9740 (p95.D9.1). In one embodiment, the antibody is p95.D9.1. In a preferred embodiment, the sample is a biological sample. In a preferred embodiment, the sample is a tissue sample. In a preferred embodiment, the sample is a fixed sample, a frozen sample or a lysate. In a preferred embodiment, the sample is a tumor sample. In a preferred embodiment, the sample is a frozen tumor tissue sample. In a preferred embodiment, the sample comprises a tumor lysate. In a preferred embodiment, the sample comprises a breast cancer sample. In a preferred embodiment, the sample is an FFPE sample. In a preferred embodiment, the sample is a blood, plasma or lymph sample. In a preferred embodiment, the blood or plasma sample contains circulating tumor cells. In a preferred embodiment, the sample contains exosomes and/or other vesicles. In a preferred embodiment, the sample comprises cell lines. In a preferred embodiment, the measurement may be quantitative across a wide dynamic range.

In a preferred embodiment, determining the presence and/or quantity of binding compound bound to p95 further comprises providing a second binding compound, the second binding compound being able to specifically bind the binding compound bound to p95 and determining the presence and/or quantity of the second binding compound as correlative of the presence and/or quantity of the binding compound bound to p95. In a preferred embodiment, the second binding compound is an antibody.

The use of a second binding compound that is capable of specifically binding the first binding compound and has one or more molecular tags may have practical advantages. For example, multiple p95-specific first binding compounds may be tested using a single second binding compound to which is attached one or more molecular tags, abrogating the need for attaching molecular tags to each of the multiple p95-specific first binding compounds. In a preferred embodiment, the first binding compound is a mouse antibody and the second binding compound is an anti-mouse antibody raised in a non-mouse species (e.g., goat anti-mouse antibodies) to which cleavable molecular tags have been attached.

Second binding compounds are typically labeled with probes useful for detection. Detection systems commonly used for detecting second binding compounds include but are not limited to cleavable molecular tags, as described herein; radiolabels (i.e., radioisotopes such as I-125); enzymes that convert a chemical into a measurable colorimetric, fluorescent or electrochemical signal (e.g., peroxidases) and fluorescent proteins (e.g., green fluorescent protein and its many derivatives). One of the most commonly used detection systems, for example, for immunohistochemistry, is to conjugate horseradish peroxidase (HRP) to an antibody or other binding compound. A substrate can then be oxidized by HRP, yielding a product detectable by a spectrophotometric method. Substrates for HRP include both chromogenic substrates (e.g., 3,3',5,5'-tetramethylbenzidine [TMB] or 3,3'-diaminobenzidine [DAB]), which yield colored products and chemiluminescent substrates (e.g., enhanced luminol chemiluminescence [ECL]), which yield light. Immunohistochemistry detection methods using secondary binding compounds and peroxidases typically involve either tagging the primary binding compound with a small molecule that can be bound with a second binding compound to which a peroxidase has been conjugated (e.g., a streptavidin/biotin system) or using a secondary antibody that has been conjugated with peroxidase targeted to the first antibody (e.g., a goat-anti-mouse antibody). Substrate is then added under conditions that will allow the conversion to product in a relatively quantitative manner and spectrophotometric methods are then used to detect the product.

The antibody can be monoclonal, polyclonal or recombinant and can be prepared by techniques that are well known in the art. Antibodies may include a complete immunoglobulin or fragment thereof, which immunoglobulins include the various classes and isotypes, such as IgA, IgD, IgE, IgG1, IgG2a, IgG2b and IgG3, IgM, etc. Fragments thereof may include Fab, Fv and F(ab')2, Fab' and the like. Antibodies may also be single-chain antibodies, chimeric antibodies, humanized antibodies or any other antibody derivative known to one of skill in the art that retains binding activity that is specific for a particular binding site. In addition, aggregates, polymers and conjugates of immunoglobulins or their fragments can be used where appropriate so long as binding affinity is maintained.

To facilitate the development of methods to measure p95 in biological samples, p95-specific monoclonal antibodies were created. Mice were immunized against peptides from p95 and standard methods as set forth further herein and as known to one skilled in the art were used to create hybridomas. Many methods are known for the creation and production of monoclonal antibodies, for example, the hybridoma method as first described by Koehler et al. (1975) *Nature* 256:495-497 or other methods described in the literature (see Goding, J W (1980) *J. Immunol. Methods* 34:285-308; Harlow E and Lane D (1988) in *Antibodies: A Laboratory Manual*, Chapter 6; Kennett R H et al. (1980) *Monoclonal Antibodies*, Plenum Press; Zola H (1987) *Monoclonal Antibodies: A Manual of Techniques*, CRC Press).

In one embodiment, the method of creating hybridomas begins with immunizing a host animal, such as a mouse, to elicit the production of lymphocytes that produce antibodies targeted to the peptide or protein(s) of interest. Lymphocytes may also be immunized in vitro. The antigen used may be a peptide, a protein or a cell displaying the antigen on the cell surface. Lymphocytes are collected then fused by chemical (e.g., with PEG) or electrical (e.g., by electrofusion) methods with myeloma cells to form hybridoma cells, typically under conditions that prevent the growth and/or survival of the parent myeloma cells. Fused cells are allowed to grow because they contain enzymes that facilitate survival in the culture medium. In a preferred embodiment, the culture medium contains hypoxanthine, aminopterin and thymidine (HAT medium), which prevents the growth of cells lacking hypoxanthine quinine phosphoribosyl transferase (HPRT). The HPRT is supplied to the fused cell by the lymphocyte partner, allowing survival of the hybridoma but preventing survival of the parent myeloma cells, which lack HPRT.

Culture media in which hybridomas are grown (i.e., conditioned media) are typically assayed for the production of monoclonal antibodies directed against the antigen using a variety of techniques (see Voller, et al. (1978) *J. Clin. Pathol.* 31:507-520), including but not limited to, immunoprecipitation or an in vitro binding assay such as enzyme-linked immunosorbant assay (ELISA; see Engvall E (1977) in *Biomedical Applications of Immobilized Enzymes and Proteins*, edited by TMS Chang, 2:87-96, Plenum Press), radioimmunoassay (RIA; see Sonksen P H (1974) *Brit. Med. Bull.* 30:1-103), Western blots or flow cytometry. Conditioned media from the hybridomas were profiled in a series of assays including ELISA (FIG. 1), Western blot (FIG. 2) and flow cytometry (FIG. 3). In preferred embodiments, studies using both native and permeabilized and fixed cells are performed to identify antibodies that may perform well in applications that use fixed cells or tissues, such as immunohistochemistry (IHC). Clones of interest may be subcloned by limiting dilution or single cell flow cytometry.

As will be known to those skilled in the art, monoclonal antibodies secreted by hybridoma clones (or subclones) can be purified using conventional purification procedures such as, but not limited to, dialysis, affinity chromatography, gel electrophoresis or protein A-sepharose (or protein L-agarose) chromatography.

Many methods and reagents are commonly used to prepare biological samples for analysis. Several methods are outlined or referenced herein and many others are known to those skilled in the art. Samples containing p95 suitable for use as biomarkers may come from a wide variety of sources, including cell cultures, animal or plant tissues, patient biopsies, blood or the like. Preferably, samples are human patient samples. Samples are prepared for assays of the invention using conventional techniques, which may depend on the source from which a sample is taken. For biopsies and medical specimens, guidance is provided in the following references: Bancroft J D & Stevens A, eds. 1977, *Theory and Practice of Histological Techniques*, Churchill Livingstone, Edinburgh; Pearse, 1980, *Histochemistry. Theory and applied.* $4^{th}$ ed., Churchill Livingstone, Edinburgh.

Examples of patient tissue samples that may be used include, but are not limited to, tissues of breast, prostate, ovary, colon, lung, endometrium, stomach, salivary gland or pancreas. The tissue sample can be obtained by a variety of procedures including surgical excision, aspiration or biopsy. The tissue may be fresh or frozen. In one embodiment, the biological sample may be cells cultured in vitro and collected by centrifugation as a cell pellet. In one embodiment, the samples may be patient blood samples or specific blood cell types or subsets of blood cell types (e.g., buffy coats). In one embodiment, the biological sample may be exosomes or samples containing exosomes. Exosomes are small (30-200 nm) vesicles that can be secreted by most cell types, including tumor cells (see Mignot et al (2006) *J. Cell. Mol. Med.* 10:376-388), in vivo and in vitro. Tumor-derived exosomes are thought to play a role in the ability of tumors to evade the immune system and have potential for both diagnostic and therapeutic applications (see Taylor and Black (1985) *J. Natl. Cancer Inst.* 74:859-867) and are therefore biological samples of interest.

In a preferred embodiment, the sample is a tumor sample. Examples of types of tumor samples include cancers such as, without limitation, carcinomas, sarcomas, myelomas, leukemias, lymphomas and mixed type cancers. In one embodiment, the cancer is a bone cancer, for example, Ewing's sarcoma, osteosarcoma and rhabdomyosarcoma and other soft-tissue sarcomas. In another embodiment, the cancer is a brain tumor, for example, oligodendroglioma, ependymoma, menengioma, lymphoma or schwannoma ormedulloblastoma. In another embodiment, the cancer is breast cancer. In another embodiment, the cancer is an endocrine system cancer, for example, adrenal, pancreatic, parathyroid, pituitary and thyroid cancers. In another embodiment, the cancer is a gastrointestinal cancer, for example, anal, colorectal, esophogeal, gallbladder, gastric, liver, pancreatic and small intestine cancers. In another embodiment, the cancer is a gynecological cancer, for example, cervical, endometrial, uterine, fallopian tube, gestational trophoblastic disease, choriocarcinoma, ovarian, vaginal and vulvar cancers. In another embodiment, the cancer is a head and neck cancer, for example, laryngeal, oropharyngeal, parathryoid or thyroid cancer. In another embodiment, the cancer is a leukemic cancer, for example, acute lymphocytic leukemia, acute myelogenous leukemia, chronic lymphocytic leukemia, chronic myelogenous leukemia, hairy cell leukemia or a myeloproliferative disorder. In another embodiment, the cancer is a lung cancer, for example, a mesothelioma or non-small cell lung cancer. In another embodiment, the cancer is a lymphoma, cutaneous T cell lymphoma, Hodgkin's disease or non-Hodgkin's disease. In another embodiment, the cancer is metastatic cancer. In another embodiment, the cancer is a myeloma, for example, a multiple myeloma. In another embodiment, the cancer is penile cancer. In another embodiment, the cancer is prostate cancer. In another embodiment, the cancer is testicular cancer. In another embodiment, the cancer is thyroid cancer, for example, papillary, follicular, medullary or anaplastic or undifferentiated thyroid carcinoma. In another embodiment, the cancer is urinary tract cancers, for example, bladder, kidney or urethral cancers.

Methods for preparing cells cultured in vitro as fresh, frozen or fixed samples are known to those with skill in the art and exemplary methods are described herein. In one embodiment, assays of the invention are carried out on tissue samples that have been fixed and embedded in paraffin and a step of deparaffination may be carried out. A tissue sample may be fixed (i.e., preserved) by conventional methodology. See, e.g., Lee G. Luna, H T (ASCP) Ed., 1960, *Manual of Histological Staining Method of the Armed Forces Institute of Pathology* 3$^{rd}$ edition, The Blakston Division McGraw-Hill Book Company, New York; Ulreka V. Mikel, Ed., 1994, *The Armed Forces Institute of Pathology Advanced Laboratory Methods in Histology and Pathology*, Armed Forces Institute of Pathology, American Registry of Pathology, Washington, D.C. One of skill in the art will appreciate that the choice of a fixative is determined by the purpose for which the tissue is to be histologically stained or otherwise analyzed. One of skill in the art will also appreciate that the length of fixation depends upon the size of the tissue sample and the fixative used.

Generally, a tissue sample is first fixed and is then dehydrated through an ascending series of alcohols, infiltrated and embedded with paraffin or other sectioning media so that the tissue sample may be sectioned. Alternatively, one may section the tissue and fix the sections obtained. By way of example, the tissue sample may be embedded and processed in paraffin by conventional methodology according to conventional techniques or as described herein. Once the tissue sample is embedded, the sample may be sectioned by a microtome according to conventional techniques. Sections may have a thickness in a range from about three microns to about twelve microns, and preferably, a thickness in a range of from about 5 microns to about 10 microns. In one embodiment, a section may have an area of from about 10 mm$^2$ to about 1 cm$^2$. Once cut, the sections may be attached to slides by several standard methods. Examples of slide adhesives include, but are not limited to, silane, gelatin and poly-L-lysine. Paraffin-embedded sections may be attached to positively charged slides and/or slides coated with poly-L-lysine.

If paraffin has been used as the embedding material, the tissue sections are generally deparaffinized and rehydrated prior to detection of biomarkers. Tissue sections may be deparaffinized by several conventional standard methodologies. For example, xylenes and a gradually descending series of alcohols may be used according to conventional techniques described by the references provided herein. Alternatively, commercially available deparaffinizing non-organic agents such as Hemo-De® (CMS, Houston, Tex.) may be used.

Cell lysates of mammalian tissue culture cells or fresh or frozen tissues may be prepared by conventional cell lysis techniques (e.g., 0.14 M NaCl, 1.5 mM MgCl$_2$, 10 mM Tris-Cl (pH 8.6), 0.5% Nonidet P-40, and protease and/or phosphatase inhibitors as required). For fresh mammalian tissues, sample preparation may also include a tissue disaggregation step, such as crushing, mincing, grinding or sonication.

Cell lysates were prepared and tested in Western blots against Ab8 or CB11, anti-Her2 antibodies that bind an intracellular epitope of Her2 and are thus capable of detecting both full length Her2 and p95. The results confirm that both the SKBR3 and MCF7 cell lines transfected with the p95 expression vectors express p95 and that transfected full length Her2 is also expressed in MCF7 cells. The SKBR3 cell line expresses endogenous high levels of Her2, as well as some p95, which is expected because SKBR3 is known to shed Her2-ECD (see Zabrecky et al. (1991) *J. Biol. Chem.* 266:1716-1720).

Six cell lines were tested using the putative p95-specific monoclonal antibodies: MCF7; MCF7 transfected with either full length Her2, p95 or CTF; SKBR3 and SKBR3 transfected with HER2 carboxy terminal fragments (CTF). CTF and p95 are used interchangeably to describe the family of truncated HER2 with PAGE apparent molecular weights similar to 95 kiloDaltons (see definition of p95 and Anido et al. (2006) *EMBO J.* 12:3234-3244). The results are shown in FIG. 6. Two monoclonal antibodies were shown to be specific for p95, D8.2 and D9.1.

The ability of the p95-specific antibody D9.1 to detect p95 in tumors was tested in tumor samples, which were selected to have a high probability of containing p95. Her2-positive tumor samples from patients with node-positive status (both factors correlating with p95-positivity) were obtained as matched fresh-frozen and formalin-fixed, paraffin-embedded samples. Western blots were prepared with lysates from the fresh-frozen material and probed with CB11, a commercially-available antibody targeted to the intracellular domain of Her2. The results, shown in FIG. 7a, allowed assignation of p95-positive status to 7 of the 12 tumor samples. The FFPE samples of all 12 tumors were then tested in the VeraTag assay using the D9.1 antibody as described in Example 4 (also see, for example, FIGS. 7b and 7c). Tumor samples are heterogeneous in nature, so some differences in the p95 levels of fresh-frozen and FFPE samples were expected.

Isotype controls are typically performed to eliminate the possibility that the binding results are due to the particular isotype of the antibody rather than the individual antibody. Additionally, one skilled in the art will appreciate that any signal "noise" seen in the isotype controls can be subtracted from the total signal, potentially yielding a more refined result. When an isotype control experiment was performed (see FIGS. 8a and 8b) and the control result subtracted from the test result with D9.1, the difference between the median p95-positive and p95-negative populations was retained and significant (approximately 4-fold different with a dynamic range of approximately 10-fold; see FIG. 8c).

In a third aspect, the invention is drawn to a method of measuring and/or quantifying the presence and/or quantity of p95 or a p95 complex in a sample, the method comprising: mixing (i) a sample that may contain p95 or a p95 complex; (ii) a proximity probe that is capable of binding p95 or an analyte which binds p95 or a p95 complex, the proximity probe having an effective proximity and (iii) at least one binding compound, the at least one binding compound being capable of binding p95, or an analyte which binds p95. and having one or more molecular probes attached, wherein binding of the proximity probe and binding compound within the effective proximity produces a signal from the molecular probes that correlates with the presence and/or quantity of p95 or p95 complex. In a preferred embodiment, the proximity probe and/or binding compound is capable of specifically binding p95. In a preferred embodiment, the proximity probe and/or binding compound further comprises an antibody. In a preferred embodiment, the proximity probe and/or the binding compound further comprises an antibody, and each antibody binds to a specific epitope on p95. In a preferred embodiment, the antibody was raised against one of the peptides having SEQ ID NOs 1-7. In certain embodiments, the antibody is or comprises one of the antibodies produced by hybridoma cell lines deposited with the ATCC having accession number PTA-9738 (p95.D3.4), PTA-9739 (p95.D8.2) and PTA-9740 (p95.D9.1). In one embodiment, the antibody is p95.D9.1.

In a preferred embodiment, the proximity probe comprises an antibody and a first nucleic acid and the binding compound comprises an antibody and a second nucleic acid, wherein the first and the second nucleic acids are complementary to each other and able to hybridize to determine the effective proximity and produce the signal through hybridization. Hybridization may be quantified by any method known to one skilled in the art such as, for example, measuring molecular tags attached to the nucleic acid molecules or measuring hybridization with any method known to one skilled in the art. In a preferred embodiment, hybridization is measured through a nucleic acid amplification method such as, for example, the rolling circle amplification method. In a preferred embodiment, the antibody was raised against one of the peptides having SEQ ID NOs 1-7. In certain embodiments, the antibody is or comprises one of the antibodies produced by hybridoma cell lines deposited with the ATCC having accession number PTA-9738 (p95.D3.4), PTA-9739 (p95.D8.2) and PTA-9740 (p95.D9.1). In one embodiment, the antibody is p95.D9.1. In a preferred embodiment, the sample is a biological sample. In a preferred embodiment, the sample is a tissue sample. In a preferred embodiment, the sample is a fixed sample, a frozen sample or a lysate. In a preferred embodiment, the sample is a tumor sample. In a preferred embodiment, the sample is a frozen tumor tissue sample. In a preferred embodiment, the sample comprises a tumor lysate. In a preferred embodiment, the sample comprises a breast cancer sample. In a preferred embodiment, the sample is an FFPE sample. In a preferred embodiment, the sample is a blood, plasma or lymph sample. In a preferred embodiment, the blood or plasma sample contains circulating tumor cells. In a preferred embodiment, the sample contains exosomes and/or other vesicles. In a preferred embodiment, the sample comprises cell lines. In a preferred embodiment, the measurement may be quantitative across a wide dynamic range. Examples of proximity probes and binding compounds, as set forth herein, can be found, for example, in U.S. Pat. Nos. 7,306,904; 7,320,860 and 7,351,528, each of which is incorporated by reference herein, including any drawings.

Proximity assays are increasingly useful for the understanding of the biological role of molecular complexes, as well as in the study of biomarkers. For example, binding compounds that specifically bind p95 or a p95 complex can be coupled with many different detection systems to measure the presence and/or quantity of p95 or a p95 complex. Any method known to one of skill in the art to be useful for determining an amount of p95 or a p95 complex can be used in accordance with the present invention. Such methods include but are not limited to Foerster resonance energy transfer (FRET), bioluminescence resonance energy transfer (BRET), biomolecular fluorescence complementation, proximity ligation assay (PLA), scintillation proximity assays (SPA) and rolling circle amplification (RCA) or any other method for detecting nucleic acid duplexes formed by the proximity of a binding probe and a proximity probe with complementary strands of nucleic acids.

In conducting the methods of the invention, a combination of the assay components is made, including the sample being tested, the binding compounds and optionally the proximity probe. Generally, assay components may be combined in any order. In certain applications, however, the order of addition may be relevant. For example, one may wish to monitor competitive binding, such as in a quantitative assay. Or one may wish to monitor the stability of an assembled complex. In such applications, reactions may be assembled in stages.

The amounts of each reagent can generally be determined empirically. The amount of sample used in an assay will be determined by the predicted number of target complexes present and the means of separation and detection used to monitor the signal of the assay. In general, the amounts of the binding compounds and the proximity probe can be provided in molar excess relative to the expected amount of the target molecules in the sample, generally at a molar excess of at least about 1.5, more desirably about 10-fold excess, or more. In specific applications, the concentration used may be higher or lower, depending on the affinity of the binding compound or proximity probe and the expected number of target molecules present on a single cell.

The assay mixture can be combined and incubated under conditions that provide for binding of the probes to the cell surface molecules, usually in an aqueous medium, generally at a physiological pH (comparable to the pH at which the cells are cultured), maintained by a buffer at a concentration in the range of about 10 to 200 mM. Conventional buffers may be used, as well as other conventional additives as necessary, such as salts, growth medium, stabilizers, etc. Physiological and constant temperatures are normally employed. Incubation temperatures normally range from about 4° to 70° C., usually from about 15° to 45° C., more usually about 25° to 37° C.

In a preferred embodiment, the proximity probe comprises a proximity probe that has a cleavage-inducing moiety and the at least one binding compound has one or more molecular tags attached to the binding compound by a cleavable linkage, wherein the cleavable linkage may be cleaved within the effective proximity producing a signal that correlates with the presence and/or quantity of p95. In a preferred embodiment, the binding compound and/or the proximity probe further comprises an antibody, and each antibody binds to a specific epitope on p95 or an analyte that binds p95. In a preferred embodiment, the antibody was raised against one of the peptides having SEQ ID NOs 1-7. In certain embodiments, the antibody is or comprises one of the antibodies produced by hybridoma cell lines deposited with the ATCC having accession number PTA-9738 (p95.D3.4), PTA-9739 (p95.D8.2) and PTA-9740 (p95.D9.1). In one embodiment, the antibody is p95.D9.1. In a preferred embodiment, the sample is a biological sample. In a preferred embodiment, the sample is a tissue sample. In a preferred embodiment, the sample is a fixed sample, a frozen sample or a lysate. In a preferred embodiment, the sample is a tumor sample. In a preferred embodiment, the sample is a frozen tumor tissue sample. In a preferred embodiment, the sample comprises a tumor lysate. In a preferred embodiment, the sample comprises a breast cancer sample. In a preferred embodiment, the sample is an FFPE sample. In a preferred embodiment, the sample is a blood, plasma or lymph sample. In a preferred embodiment, the blood or plasma sample contains circulating tumor cells. In a preferred embodiment, the sample contains exosomes and/or other vesicles. In a preferred embodiment, the sample comprises cell lines. In a preferred embodiment, the measurement may be quantitative across a wide dynamic range.

Many advantages are provided by measuring p95 or a p95 complex using releasable molecular tags, including separation of released molecular tags from an assay mixture providing greatly reduced background and a significant gain in sensitivity and separation and detection providing a convenient multiplexing capability so that multiple receptor complex components may be readily measured simultaneously in the same assay. Assays employing such tags can have a variety of forms and are disclosed in the following references: U.S. Pat. Nos. 7,105,308; 6,627,400; 7,402,397; 7,402,398 and 7,402,399, as well as International Patent Publication No. WO 2004/011900, each of which is incorporated herein by reference in its entirety. A wide variety of separation techniques may be employed that can distinguish molecules based on one or more physical, chemical or optical differences among molecules being separated including electrophoretic mobility, molecular weight, shape, solubility, pKa, hydrophobicity, charge, charge/mass ratio or polarity. In one embodiment, molecular tags in a plurality or set differ in electrophoretic mobility and optical detection characteristics and are separated by electrophoresis. In another embodiment, molecular tags in a plurality or set may differ in molecular weight, shape, solubility, pKa, hydrophobicity, charge, polarity and are separated by normal phase or reverse phase HPLC, ion exchange HPLC, capillary electrochromatography, mass spectroscopy or gas phase chromatography.

Sets of molecular tags are provided that can be separated into distinct bands or peaks by a separation technique after they are released from binding compounds. Identification and quantification of such peaks provides a measure or profile of the presence and/or amounts of p95. Molecular tags within a set may be chemically diverse; however, for convenience, sets of molecular tags are usually chemically related. For example, they may all be peptides or they may consist of different combinations of the same basic building blocks or monomers or they may be synthesized using the same basic scaffold with different substituent groups for imparting different separation characteristics. The number of molecular tags in a plurality may vary depending on several factors including the mode of separation employed, the labels used on the molecular tags for detection, the sensitivity of the binding moieties and the efficiency with which the cleavable linkages are cleaved.

Measurements made directly on tissue samples may be normalized by including measurements on cellular or tissue targets that are representative of the total cell number in the sample and/or the numbers of particular subtypes of cells in the sample (see, for example, United States Provisional Application No. 61/015,608 which is incorporated by reference herein, including any drawings). The additional measurement may be preferred, or even necessary, because of the cellular and tissue heterogeneity in patient samples, particularly tumor samples, which may comprise substantial fractions of normal cells.

In one embodiment, a binding compound can be represented by the following formula:

$$B\text{-}(L\text{-}E)_k$$

wherein B is binding moiety; L is a cleavable linkage and E is a molecular tag. In homogeneous assays, cleavable linkage, L, may be an oxidation-labile linkage, and more preferably, it is a linkage that may be cleaved by singlet oxygen. The moiety "-(L-E)$_k$" indicates that a single binding compound may have multiple molecular tags attached via cleavable linkages. In one aspect, k is an integer greater than or equal to one, but in other embodiments, k may be greater than several hundred, e.g. 100 to 500 or k is greater than several hundred to as many as several thousand, e.g. 500 to 5000. Usually each of the plurality of different types of binding compounds has a different molecular tag, E. Cleavable linkages, e.g. oxidation-labile linkages, and molecular tags, E, are attached to B by way of conventional chemistries.

Preferably, B is an antibody that specifically binds to a target, such as p95. Antibodies specific for p95 epitopes are provided in the examples set forth herein. Antibody compositions may be readily formed from a wide variety of commercially available antibodies, either monoclonal or polyclonal or by methods disclosed herein.

Cleavable linkage, L, can be virtually any chemical linking group that may be cleaved under conditions that do not degrade the structure or affect detection characteristics of the released molecular tag, E. Whenever a cleaving probe is used in a homogeneous assay format, cleavable linkage, L, is cleaved by a cleavage agent generated by the cleaving probe that acts over a short distance so that only cleavable linkages within an effective proximity of the proximity probe are cleaved. Typically, such an agent must be activated by making a physical or chemical change to the reaction mixture so that the agent produces a short lived active species that diffuses to a cleavable linkage to affect cleavage.

In a non-homogeneous format, because specifically-bound binding compounds are separated from unbound binding compounds, a wider selection of cleavable linkages and cleavage agents are available for use. Cleavable linkages may not only include linkages that are labile to reaction with a locally acting reactive species, such as hydrogen peroxide, singlet oxygen or the like, but also linkages that are labile to agents that operate throughout a reaction mixture, such as base-labile linkages, photocleavable linkages, linkages cleavable by reduction, linkages cleaved by oxidation, acid-labile linkages and peptide linkages cleavable by specific proteases. References describing many such linkages include Greene and Wuts, 1991, *Protective Groups in Organic Synthesis, Second Edition*, John Wiley & Sons, New York; Hermanson, 1996, *Bioconjugate Techniques*, Academic Press, New York; and U.S. Pat. No. 5,565,324, each of which is incorporated by reference herein.

Molecular tag, E, in the present invention may comprise an electrophoric tag as described in the following references when separation of pluralities of molecular tags are carried out by gas chromatography or mass spectrometry: See, e.g., Zhang et al., 2002, *Bioconjugate Chem.* 13:1002-1012; Giese, 1983, *Anal. Chem.* 2:165-168; and U.S. Pat. Nos. 4,650,750; 5,360,819; 5,516,931; and 5,602,273, each of which is hereby incorporated by reference in its entirety.

Molecular tag, E, is preferably a water-soluble organic compound that is stable with respect to the active species, especially singlet oxygen, and that includes a detection or reporter group. Otherwise, E may vary widely in size and structure. In one embodiment, E has a molecular weight in the range of from about 50 to about 2500 Daltons, more preferably, from about 50 to about 1500 Daltons. E may comprise a detection group for generating an electrochemical, fluorescent or chromogenic signal. In embodiments employing detection by mass, E may not have a separate moiety for detection purposes. Preferably, the detection group generates a fluorescent signal.

Molecular tags within a plurality are selected so that each has a unique separation characteristic and/or a unique optical property with respect to the other members of the same plurality. In one embodiment, the chromatographic or electrophoretic separation characteristic is retention time under a set of standard separation conditions conventional in the art, e.g., voltage, column pressure, column type, mobile phase or electrophoretic separation medium. In another embodiment, the optical property is a fluorescence property, such as emission spectrum, fluorescence lifetime or fluorescence intensity at a given wavelength or band of wavelengths. Preferably, the fluorescence property is fluorescence intensity. One or two or more of the molecular tags of a plurality may have identical migration or retention times, but they will have unique fluorescent properties, e.g. spectrally resolvable emission spectra, so that all the members of the plurality are distinguishable by the combination of molecular separation and fluorescence measurement.

Preferably, released molecular tags are detected by electrophoretic separation and the fluorescence of a detection group. In such embodiments, molecular tags having substantially identical fluorescence properties have different electrophoretic mobilities so that distinct peaks in an electropherogram are formed under separation conditions. Preferably, pluralities of molecular tags of the invention are separated by a conventional capillary electrophoresis apparatus, either in the presence or absence of a conventional sieving matrix. During or after electrophoretic separation, the molecular tags are detected or identified by recording fluorescence signals and migration times (or migration distances) of the separated compounds or by constructing a chart of relative fluorescent and order of migration of the molecular tags (e.g., as an electropherogram). Preferably, the presence, absence and/or amounts of molecular tags are measured by using one or more standards.

A cleavage-inducing moiety, or cleaving agent, is a group that produces an active species that is capable of cleaving a cleavable linkage, preferably by oxidation. Preferably, the active species is a chemical species that exhibits short-lived activity so that its cleavage-inducing effects are only in the proximity of the site of its generation. Either the active species is inherently short lived, so that it will not create significant background beyond the proximity of its creation, or a scavenger is employed that efficiently scavenges the active species, so that it is not available to react with cleavable linkages beyond a short distance from the site of its generation. Illustrative active species include singlet oxygen, hydrogen peroxide, NADH and hydroxyl radicals, phenoxy radical, superoxide and the like. Illustrative quenchers for active species that cause oxidation include polyenes, carotenoids, vitamin E, vitamin C, amino acid-pyrrole N-conjugates of tyrosine, histidine and glutathione. See, e.g. Beutner et al., 2000, *Meth. Enzymol.* 319:226-241.

One consideration in designing assays employing a cleavage-inducing moiety and a cleavable linkage is that they not be so far removed from one another when bound to a receptor complex that the active species generated by the cleavage-inducing moiety cannot efficiently cleave the cleavable linkage. In one embodiment, cleavable linkages preferably are within about 1000 nm and preferably within about 20-200 nm of a bound cleavage-inducing moiety. More preferably, for photosensitizer cleavage-inducing moieties generating singlet oxygen, cleavable linkages are within about 20-100 nm of a photosensitizer in a receptor complex. One of ordinary skill in the art will recognize that the effective proximity of a particular sensitizer may depend on the details of a particular assay design and may be determined or modified by routine experimentation.

A sensitizer is a compound that can be induced to generate a reactive intermediate, or species, usually singlet oxygen. Preferably, a sensitizer used in accordance with the invention is a photosensitizer. Other sensitizers included within the scope of the invention are compounds that on excitation by heat, light, ionizing radiation or chemical activation will release a molecule of singlet oxygen. The best known members of this class of compounds include the endoperoxides such as 1,4-biscarboxyethyl-1,4-naphthalene endoperoxide, 9,10-diphenylanthracene-9,10-endoperoxide and 5,6,11,12-tetraphenyl naphthalene 5,12-endoperoxide. Heating or direct absorption of light by these compounds releases singlet oxygen. Further sensitizers are disclosed by Di Mascio et al., 1994, *FEBS Lett.* 355:287 and Kanofsky, 1983, *J. Biol. Chem.* 258:5991-5993; Pierlot et al., 2000, *Meth. Enzymol.* 319:3-20.

Photosensitizers may be attached directly or indirectly, via covalent or non-covalent linkages, to the antibodies. Guidance for constructing such compositions are available in the literature, e.g. in the fields of photodynamic therapy, immunodiagnostics and the like. Exemplary guidance may be found in Ullman et al., 1994, *Proc. Natl. Acad. Sci. USA* 91, 5426-5430; Strong et al., 1994, *Ann. New York Acad. Sci.* 745: 297-320; Yarmush et al., 1993, *Crit. Rev. Therapeutic Drug Carrier Syst.* 10: 197-252; and U.S. Pat. Nos. 5,709, 994, 5,340,716, 6,251,581, and 5,516,636.

A large variety of light sources are available to photoactivate photosensitizers to generate singlet oxygen. Both polychromatic and monochromatic sources may be used as long as the source is sufficiently intense to produce enough singlet oxygen in a practical time duration. The length of the irradiation depends on the nature of the photosensitizer, the nature of the cleavable linkage, the power of the source of irradiation and its distance from the sample. In general, the period for irradiation may be less than about a microsecond to as long as about 10 minutes, usually in the range of about one millisecond to about 60 seconds. The intensity and length of irradiation should be sufficient to excite at least about 0.1% of the photosensitizer molecules, usually at least about 30% of the photosensitizer molecules and preferably, substantially all of the photosensitizer molecules. Exemplary light sources include lasers such as, e.g., helium-neon lasers, argon lasers, YAG lasers, He/Cd lasers and ruby lasers; photodiodes; mercury, sodium and xenon vapor lamps and incandescent lamps such as, e.g., tungsten and tungsten/halogen and flashlamps. An exemplary photoactivation device suitable for use in the methods of the invention is disclosed International Patent Publication No. WO 03/051669, which is incorporated by reference herein, including any drawings. In such embodiments, the photoactivation device is an array of light emitting diodes (LEDs) mounted in housing that permits the simultaneous illumination of all the wells in a 96-well plate.

Examples of photosensitizers that may be utilized in the present invention are those that have the above properties and those disclosed by U.S. Pat. Nos. 5,536,834, 5,763,602, 5,565,552, 5,709,994, 5,340,716, 5,516,636, 6,251,581 and 6,001,673; published European Patent Application No. 0484027; Martin et al., 1990, *Methods Enzymol.* 186:635-645 and Yarmush et al., 1993, *Crit. Rev. Therapeutic Drug Carrier Syst.* 10:197-252, all of which are incorporated by reference herein, including any drawings. As with sensitizers, in certain embodiments, a photosensitizer may be associated with a solid phase support by being covalently or non-covalently attached to the surface of the support or incorporated into the body of the support. In general, the photosensitizer is associated with the support in an amount necessary to achieve the necessary amount of singlet oxygen. Generally, the amount of photosensitizer is determined empirically according to routine methods.

Following cleavage, the sample can then be analyzed to determine the identity of molecular tags that have been released. Where an assay employing a plurality of binding compounds is employed, separation of the molecular tags will generally precede their detection. The methods for both separation and detection are determined in the process of designing the molecular tags for the assay. A preferred mode of separation employs electrophoresis, in which the various tags are separated based on known differences in their electrophoretic mobilities.

In a fourth aspect, the invention is drawn to a purified antibody that binds to p95. In a preferred embodiment, the purified antibody binds specifically to p95. In a preferred embodiment, the antibody binds specifically to the extracellular domain of p95 but not full length HER2. In a preferred embodiment, the antibody is a polyclonal antibody or a monoclonal antibody. In a preferred embodiment, the antibody is a monoclonal antibody. In a preferred embodiment, the antibody was raised against one of the peptides having SEQ ID NOs 1-7. In a preferred embodiment, the invention is drawn to one of the peptides having SEQ ID NOs 1-7. In certain embodiments, the antibody is or comprises one of the antibodies produced by hybridoma cell lines deposited with the ATCC having accession number PTA-9738 (p95.D3.4), PTA-9739 (p95.D8.2) and PTA-9740 (p95.D9.1). In one embodiment, the antibody is p95.D9.1.

In a preferred embodiment, the invention is drawn to the DNA encoding the antibody or peptides. The DNA encoding the monoclonal antibodies is isolated and sequenced using techniques commonly known to those skilled in the art of cloning. Once isolated, the DNA can be ligated into expression vectors and transfected into appropriate host cells to obtain recombinant antibodies from cultured cells (see Plueckthun (1992) *Immunological Rev.* 130: 151-188).

Those with skill in the art will appreciate that the amino acid sequence of an antibody or peptide can be modified and that modifications may be desirable to enhance the properties of the antibody for therapeutic, analytical or diagnostic use. Further it will be appreciated that one or more amino acids in these antibodies or antibodies may be changed by insertion, deletion or substitution without appreciably diminishing the binding characteristics of the antibody. Exemplary amino acid changes would be substitutions using amino acids with similar molecular characteristics (i.e., conservative substitutions, e.g., changing amino acids from within the following subgroups of aromatic amino acids, acidic amino acids, basic amino acids or amino acids with amides or sulphurs). Other non-conservative substitutions or insertions may be made without appreciably altering molecular integrity or binding characteristics. Further, some amino acid changes or collection of amino acid changes will enhance properties of the antibody, including but not limited to, better binding affinity, greater stability, (e.g., resistance to proteases) and/or ease of production. Methods for changing amino acid sequences and/or selecting for molecules with better properties are known to those with skill in the art. Preferably, in intact antibodies or peptides, the degree of sequence identity after modification is at least 50% and more preferably, at least 75% and most preferably at least 90-95%. Each of these antibodies or peptides is intended to be within the scope of the contemplated invention.

In a preferred embodiment, antibodies targeted to p95 or peptides may be used to develop additional p95-targeted molecules. Modifications of the antibodies described herein may be desirable to improve qualities including, but not limited to, increasing function, decreasing immunogenicity, increasing stability, improving pharmacologic properties such as serum half-life and aiding in ease and yield of production. Each of these targeted molecules is intended to be within the scope of the contemplated invention.

In a preferred embodiment, humanized antibodies comprising the antigen binding regions of the antibodies described herein (ATCC # PTA-9738, PTA-9739 and PTA-9740) in a human framework may be used for therapeutic applications. Several methods for humanizing antibodies have been reported (see Jones et al. (1986) *Nature* 321:522-525, Riechmann et al. (1988) *Nature* 332:323-327, Verhoeyen et al. (1988) *Science* 239:1534-1536). Typically, the non-human sequences of the variable domain are screened computationally against the entire repertoire of human light and heavy chain variable domain sequences to find the human variable framework sequences closest to the rodent sequences (see Sims et al. (1993) *J. Immunol.* 151:2296-2308, Chothia et al. (1987) *J. Mol. Biol.* 186:901-917). Alternatively, consensus frameworks can be used (see Carter et al. (1992) *Proc. Natl. Acad. Sci. USA* 89:4285-4289 and Presta et al. (1993) *J. Immunol.* 151:2623-2632). In a preferred embodiment, computer-aided design is used to select sequences that confer stability and retain or improve binding characteristics. Each of these is intended to be within the scope of the contemplated invention.

In another embodiment, the antibody complementarity determining regions (CDRs) may be used to create targeted binding molecules that bind the same epitope in p95 but are contained within a framework that is not a native antibody. For example, one skilled in the art would appreciate that methods are available for creating binding molecules in which the framework may be a portion of an antibody, for example, an scFv or F(ab')$_2$ (see WO 93/16185 and Carter et al. (1992) *Bio/Technology* 10:163-167, respectively), each of which is incorporated by reference herein. One skilled in the art may also appreciate that a completely unrelated protein (such as a bacterial beta-lactamase) can properly display the binding domain(s) to form a binding compound. In this sense, related antibodies, as defined herein, are intended to be within the scope of the invention.

The antibody may act therapeutically through binding alone or through other properties (e.g., enzymatic activity or toxic warheads). In one embodiment, the targeted protein may be modified to exert a therapeutic effect or a greater therapeutic effect via antigen-dependent cell-mediated cytotoxicity (ADCC) or complement-dependent cytotoxicity (CDC). In another embodiment, toxins may be conjugated to the antibody or targeted protein. Exemplary small molecule toxins include but are not limited to maytansine, calicheamicin and CC-1065 (see, e.g., Carter and Senter (2008) *Cancer J.* 14:154-169). Additionally, radiolabels can be linked to antibodies to create targeted therapeutics. Biologic toxins may also be linked to targeted proteins and include, but not be limited to, diphtheria toxin, *Pseudomonas* exotoxin, abrin and ricin (see Kreitman (2006) *AAPS J.* 18:E532-551).

In a further embodiment, the targeted antibodies (or fragments thereof) may be fused to enzymes for use in antibody-directed enzyme prodrug therapy (ADEPT; see Bagashawe (1987) *Br. J. Cancer* 58:700-703 and Senter et al. (1988) *Proc. Natl. Acad. Sci. USA* 85:4842-4846). In another embodiment, the antibodies or targeted proteins may be fused to molecules such as polyethylene glycol, that enhance pharmacologic properties, such as serum half-life (see Harris and Chess (2003) *Nat. Rev. Drug Discov.* 2:214-221).

In a fifth aspect, the invention is drawn to a method for determining whether a subject with a cancer is likely to respond to treatment with a targeted therapy, for predicting a time course of disease and/or for predicting probability of a significant event in the time course of the subject's cancer based on a measurement of an amount of p95 or a p95 complex in a sample. In one embodiment, the invention is drawn to a method for determining whether a subject with a cancer is likely to respond to treatment with a Her-2 acting agent. In another embodiment, the method is drawn to a method of predicting a time course of a disease in a subject with a cancer. In another embodiment, the method is drawn to predicting the probability of a significant event in a subject with a cancer.

In a preferred embodiment, a time course is measured by determining the time between significant events in the course of a patient's disease, wherein the measurement is predictive of whether a patient has a long time course. In a preferred embodiment, the significant event is the progression from primary diagnosis to death. In a preferred embodiment, the significant event is the progression from primary diagnosis to metastatic disease. In a preferred embodiment, the significant event is the progression from primary diagnosis to relapse. In a preferred embodiment, the significant event is the progression from surgery to death. In a preferred embodiment, the significant event is the progression from surgery to relapse. In a preferred embodiment, the significant event is from surgery to metastases. In a preferred embodiment, the significant event is the progression from metastatic disease to death. In a preferred embodiment, the significant event is the progression from metastatic disease to relapse. In a preferred embodiment, the significant event is the progression from relapse to death. In a preferred embodiment, the time course is measured with respect to overall survival rate, time to progression and/or using the RECIST or other response criteria.

Her2-positive tumors are not all responsive to trastuzumab and other therapeutics that bind to epitopes in the extracellular domain of membrane-bound Her2. An explanation for a lack of responsiveness may be that cleavage of the extracellular domain removes the binding site for trastuzumab and like therapeutics, and leaves p95 with a constitutively active tyrosine kinase activity. High levels of Her2 and relatively high levels of p95, therefore, may be a meaningful marker for the likelihood that a tumor will fail to respond to trastuzumab and other therapeutics that bind to epitopes on the extracellular domain of membrane-bound Her2.

In certain embodiments, the method comprises measuring in a biological sample from the subject's cancer an amount of p95, wherein if the amount of p95 is low, then the patient is likely to respond to the Her-2 acting agent and/or the patient has a long time course. In certain embodiments, the biological sample comprises FFPEs. In certain embodiments, the subject's cancer is breast cancer. In certain embodiments, the breast cancer is metastatic. In certain embodiments, the Her-2-acting agent is trastuzumab. In certain embodiments, the assay is the VeraTag assay. In certain embodiments, likeliness to respond is measured with respect to overall survival rate, time to progression and/or using the RECIST criteria.

In certain embodiments, a predetermined measure is created by dividing patient cohorts into at least two patient subgroups. In certain embodiments, the number of subgroups is two so that the patient sample is divided into a subgroup of patients whose p95 is high and a subgroup whose p95 is low; the amount of p95 in the subject is compared to either the high subgroup or the low subgroup; if the amount of p95 in the patient is high, then the patient is not likely to respond to a Her-2 acting agent that is not a p95-acting agent and/or the patient is likely to have a short time course; if the amount of p95 is low (and the amount of Her2 is high), then the patient is likely to respond to Her-2 acting agents and the time course may be long. In certain embodiments, the number of subgroups is greater than two, including, without limitation, three subgroups, four subgroups, five subgroups and six subgroups. In certain embodiments, likeliness to respond or time course is measured with respect to overall survival rate, time to progression and/or using the RECIST criteria. In certain preferred embodiments, the Her-2 acting agent that is not a p95-acting agent is trastuzumab.

In certain embodiments, the predetermined measure is an optimal cutoff. In certain embodiments, the amount of p95 in the subject is compared to the optimal cutoff; if the amount of p95 in the patient is high, then the patient is not likely to respond to a Her-2 acting agent that is not a p95-acting agent and/or the patient's time course is likely to be short. Any method known to one of skill in the art to be useful for determining an amount of p95 expression can be used in accordance with the present invention. Such methods may include any method disclosed herein such as, for example, without limitation, VeraTag, FRET, BRET, Biomolecular Fluoresence Complementation, Proximity Ligation Assay and Rolling Circle Amplification.

In a preferred embodiment, the subject's cancer is breast cancer. In a preferred embodiment, the Her-2 acting agent is a tyrosine kinase inhibitor and if the amount of p95 is high, then the patient is likely to respond to the targeted therapy, the patient is likely to have a long time course and/or the patient is not likely to have a significant event. In a preferred embodiment, the targeted therapy is an inhibitor, such as a protease inhibitor, and if the amount of p95 is high, then the patient is likely to respond to the targeted therapy, the patient is likely to have a long time course and/or the patient is not likely to have a significant event.

In certain embodiments the Her2-acting agent is selected from the group consisting of pertuzumab, trastuzumab, canertinib, lapatinib, mubritinib, AEE-788, HKI-272, BIBW-2992, and BMS-599626. See e.g., Spector, 2007, *Breast Cancer Res.* 9:205. In a preferred embodiment, the Her-2-acting agent is trastuzumab (Herceptin®). See, e.g., Goldenberg, 1999, *Clin Ther.* 21:309-18; and Shak, 1999, *Semin Oncol.* 26:71-7.

In a preferred embodiment, the inhibitor inhibits metalloproteases including, but not limited to, matrix metalloproteases and/or member(s) of the ADAM family of proteases. In a preferred embodiment, the inhibitor inhibits ADAM10. Members of the ADAM family of metalloproteases are thought to mediate cleavage of erbB family members; specifically, ADAM10 (see Gee et al. (2003) *Breast Cancer Res.* 5:223-224 and Sahin (2004) *J. Cell Biol.* 164:769-779) is thought to be a major source of Her2 ECD sheddase activity (see Liu, P C et. al (2006) *Cancer Biology and Therapy* 6: 657-664) and is a target for therapeutic intervention.

In certain embodiments, the subject may be administered a combination therapy that includes trastuzumab. The combination therapy can include trastuzumab in combination with one or more of any chemotherapeutic agent known to one of skill in the art without limitation (see, for example, Romond, E H, *N Engl J Med* (2005) 353(16):1673, which is incorporated by reference herein, including any drawings). Preferably, the chemotherapeutic agent has a different mechanism of action from trastuzumab. Particular examples of chemotherapeutic agents that can be used in the various embodiments of the invention, including pharmaceutical compositions, dosage forms, and kits of the invention, include, without limitation, cytarabine, melphalan, topotecan, fludarabine, etoposide, idarubicin, daunorubicin, mitoxantrone, cisplatin, paclitaxel and cyclophosphamide.

In another embodiment, the invention provides an analytical method for screening therapeutic candidates for potential efficacy as therapeutic agents. In a preferred embodiment, the VeraTag assay, as described herein, can be employed to test for p95 levels in biological systems (or derivatives thereof, such as cell lines) that have been treated with putative inhibitors of enzymes (e.g., sheddases) that are thought to be involved in generating p95-dependent growth of tumors. Candidates with inhibitory activity will show decreased levels of p95 in the VeraTag assay as described herein. In a preferred embodiment, the enzymes targeted by the putative inhibitors are matrix metalloproteases. In a preferred embodiment, the enzymes are members of the ADAM family of proteases. In a preferred embodiment, the enzyme is ADAM10.

In a further aspect, the invention provides methods of treating a subject with cancer. In one aspect, the methods comprise determining that the subject is afflicted with a cancer that is likely to respond to treatment and/or has a long time course according to a method of the invention, and administering an effective amount of compound to the subject as a result of said determination. In another aspect, the methods comprise determining that a subject is afflicted with a cancer that is likely to respond to treatment according to a method of the invention, then advising a medical professional of the treatment option of administering to the subject an effective amount of an agent. In another embodiment, the agent is at least two agents.

EXAMPLES

Example 1: Generation of Expression Vectors for Tagged p95 and HER2

Expression vectors for p95 (pcDNA6myc/hisA M611-p95) and full-length HER2 (pcDNA6-HER2) were constructed using the pcDNA6A-myc/his vector from Invitrogen. The HER2 expression sequence included a hemagglutinin (HA) tag (expressed amino acids: YPYDVPDYA; SEQ ID NO:8) two amino acids downstream of the putative leader sequence cut site. A stop codon was included at the end of the HER2 sequence to prevent the incorporation of the myc/his tags embedded in pcDNA6A-myc/his. The p95 sequence started from Methionine-611, numbered from the HER2 amino acid sequence. Upstream from Methionine-611 was placed sequence encoding the HER2 leader sequence plus two amino acids followed by the same 9-amino acid HA tag used in the HER2 expression vector. A stop codon was not included at the end of the p95 sequence so that the myc/his tags would be included in the expressed protein.

Example 2: Generation of Antibodies Against p95

The following monoclonal antibodies/hybridomas of the present invention are described below:
P95.A3, p95.B1, p95.B2, p95.B3, p95.B4, p95.B5, p95.B6, p95.B7, p95.B8, p95.B9, p95.B10, p95.B11, p95.B12, p95.B13, p95.B14, p95.B15, p95.B16, p95.B19, p95.B20, p95.B21, p95.B23, p95.B24, p95.B25, p95.B26, p95.D2, p95.D3, p95.D4, p95.D5, p95.D6, p95.D7, p95.D8, p95.D9, p95.D10, p95.D11, p95.D12, p95.D13, p95.D102, p95.D111, p95.D112, p95.D115, p95.D117, p95.D119, p95.D120, p95.D121, p95.D123, p95.D125, p95.D126, p95.D127, p95.D128, p95.D129, p95.D131, p95.D132, p95.D133, p95.D134, p95.D135, p95.D137, p95.D139, p95.E1, p95.E2, p95.E3, p95.E4.
If the monoclonal antibody has been cloned, it will get the nomenclature "X.1," e.g., the first clone of p95.D9 will be referred to as D9.1, the second clone of D9 will be referred to as D9.2, etc. For the purposes of this invention, a reference to p95.D9 or D9 will include all clones, e.g., D9.1, D9.2, etc.

Mice were immunized with peptides representative of epitopes that are likely to be present in p95. Peptides used for immunizations were:

P95.A peptide:
(SEQ ID NO: 2)
ASPLTSIIS

P95.B peptide:
(SEQ ID NO: 3)
PAEQRASPLTSIIS

P95.D peptide:
(SEQ ID NO: 5)
MPIWKFPDEEGA

P95.E peptide:
(SEQ ID NO: 6)
PSGVKPDLSYMPIWK

Peptides were conjugated to keyhole limpet hemocyanin (KLH) for immunizations and bovine serum albumin (BSA) for screening using SMCC chemistry (Pierce, Rockford, Ill.).

Mice (Balb/c, FVB, C3H, or CD-1) were immunized with peptide-KLH conjugates twice weekly for 5 weeks to generate anti-p95 MAbs capable of binding to p95 in bodily fluids and on a cell surface. Immunizations were done intradermally in both rear footpads with 10 µg peptide-KLH conjugate. Peptide-KLH conjugates were mixed with suitable adjuvants prior to injection. Titermax (Sigma, St. Louis. Mo.) was used for the first injection; Adju-Phos (Accurate Chemical & Scientific Corp., Westbury, N.Y.) was used for injections 2 to 9. For the $10^{th}$ injection, antigen was mixed with phosphate buffer saline.

Four days after the final immunization, lymphocytes were isolated from popliteal lymph nodes and immortalized by electrofusion (electrofusion generator ECM2001; Harvard Apparatus, Holliston, Me.) with the continuous myeloma cell line P3x63Ag8.653 (Kearney, J F et al. (1979) J Immunology 123, 1548-1550). Fused cells were selected by culturing in selection medium (DMEM/15% FBS) containing 2.85 µM Azaserine, 50 µM Hypoxanthine (HA) (Sigma) or 50 µM Hypoxanthine, 0.2 µM Aminopterin, 8 µM Thymidine (HAT) (Sigma) supplemented with recombinant human IL-6 (Sigma) at 0.5 ng/mL. Cultures were transitioned into medium (DMEM/10% FBS) without selection and IL-6 supplements for continued expansion and antibody production.

Hybridoma supernatants were screened by enzyme-linked solid phase immunoassay (ELISA), flow cytometry and western blotting for reactivity against p95. Monoclonal cultures were established after the screening procedure by single cell sorting using a flow cytometer.

Hybridoma supernatants were screened by direct ELISA using 100 ng peptide-BSA conjugate or Her2-Fc fusion protein (R&D Systems, Minneapolis, Minn.) per well as antigen (Table 1). Her2-Fc is a recombinant protein containing the extracellular domain of Her2 fused to the Fc domain of human IgG. Antibodies A3, B1, B2, B3, B4, B10, B11, B12, B13, B14, B15, B20, B21, B23, E1, E2, E3 and E4 reacted with peptides p95.A and p95.B, and did not bind to Her2-Fc. Antibodies B5, B6, B8, B9, B16, B24, B25 and B26 reacted with peptide p95.B, but did not bind to peptide p95.A and Her2-Fc. Antibodies B7 and B19 bound to both peptides p95.A and p95.B, but binding to p95.A was much weaker than binding to p95.B. Antibodies D3, D5, D7, D10, D11, D13, D102, D120, D125, D126, D129, D131, D132, D133, D134 and D139 bound to peptide p95.D, and did not bind to Her2-Fc. Antibodies D2, D8, D9, D111, D115, D117, D119, D121, D123, D127, D128, D135 and D137 strongly bound to p95.D peptide, and weakly bound to Her2-Fc. Antibodies D4, D6 and D12 strongly bound to both p95.D peptide and Her2-Fc.

Table 1 shows the screening of conditioned media from the hybridomas by direct ELISA. Wells were coated with 100 ng antigen (peptides p95.A, p95.B, p95.D, a negative control peptide unrelated in sequence to Her2, or Her2-Fc recombinant protein) and probed with hybridoma supernatants. Her2-Fc protein, containing the extracellular domain (ECD) of Her2, was obtained from R&D Systems as a chimeric protein fused to the Fc region of human IgG1. Bound antibody was detected with an alkaline phosphatase-conjugated goat-anti-mouse IgG antiserum. OD values for hybridoma supernatant/antigen pair are listed.

TABLE 1

| Hybridoma supernatant | p95.A peptide | p95.B peptide | p95.D peptide | Her2 Fc protein | control peptide |
| --- | --- | --- | --- | --- | --- |
| A3 | 1.393 | 2.027 | | 0.131 | 0.118 |
| B1 | 2.753 | 3.495 | | 0.096 | 0.119 |
| B2 | 1.912 | 2.053 | | 0.089 | 0.122 |
| B3 | 0.913 | 0.928 | | 0.085 | 0.132 |
| B4 | 1.835 | 2.482 | | 0.103 | 0.143 |
| B5 | 0.121 | 0.667 | | 0.108 | 0.132 |
| B6 | 0.115 | 2.915 | | 0.109 | 0.13 |
| B7 | 0.358 | 3.251 | | 0.107 | 0.135 |
| B8 | 0.11 | 0.995 | | 0.108 | 0.134 |
| B9 | 0.091 | 3.777 | | 0.092 | 0.116 |
| B10 | 2.212 | 3.03 | | 0.095 | 0.115 |
| B11 | 1.553 | 1.916 | | 0.092 | 0.118 |
| B12 | 2.491 | 2.941 | | 0.104 | 0.119 |
| B13 | 1.495 | 1.679 | | 0.122 | 0.144 |
| B14 | 3.693 | 3.858 | | 0.129 | 0.14 |
| B15 | 0.29 | 0.345 | | 0.102 | 0.129 |
| B16 | 0.108 | 1.78 | | 0.097 | 0.124 |
| B19 | 0.238 | 0.693 | | 0.092 | 0.103 |
| B20 | 0.447 | 0.855 | | 0.102 | 0.114 |
| B21 | 0.515 | 0.7 | | 0.109 | 0.124 |
| B23 | 2.95 | 3.625 | | 0.1 | 0.118 |
| B24 | 0.112 | 3.447 | | 0.1 | 0.117 |
| B25 | 0.089 | 1.556 | | 0.093 | 0.104 |
| B26 | 0.088 | 2.791 | | 0.094 | 0.102 |
| E1 | 3.7206 | 3.8345 | | 0.1101 | 0.1102 |
| E2 | 1.3195 | 1.8344 | | 0.1023 | 0.0983 |
| E3 | 2.7201 | 2.4782 | | 0.1115 | 0.1106 |
| E4 | 1.9273 | 1.9121 | | 0.1168 | 0.1180 |
| D2 | | | 1.4276 | 0.2555 | 0.0762 |
| D3 | | | 2.3055 | 0.0890 | 0.1336 |
| D4 | | | 3.9405 | 1.6825 | 0.1070 |
| D5 | | | 3.4171 | 0.0939 | 0.1080 |
| D6 | | | 0.9020 | 1.7200 | 0.0861 |
| D7 | | | 2.0873 | 0.1152 | 0.0932 |
| D8 | | | 3.7010 | 0.2191 | 0.0835 |
| D9 | | | 3.4600 | 0.3109 | 0.0837 |
| D10 | | | 3.1198 | 0.0865 | 0.0944 |
| D11 | | | 3.3918 | 0.1026 | 0.0814 |
| D12 | | | 3.8707 | 4.0000 | 0.0921 |
| D13 | | | 1.1890 | 0.0923 | 0.0956 |
| D102 | | | 3.6168 | 0.0968 | 0.0925 |
| D111 | | | 4.0000 | 0.6007 | 0.1107 |
| D112 | | | 0.3247 | 0.4424 | 0.1043 |
| D115 | | | 3.9346 | 0.4967 | 0.0932 |
| D117 | | | 4.0000 | 0.5348 | 0.0930 |
| D119 | | | 4.0000 | 0.5448 | 0.1078 |
| D120 | | | 0.6196 | 0.1175 | 0.1138 |
| D121 | | | 3.7442 | 0.3166 | 0.1095 |
| D123 | | | 3.7323 | 0.3121 | 0.0899 |
| D125 | | | 3.8027 | 0.0943 | 0.0934 |
| D126 | | | 3.6641 | 0.0920 | 0.0913 |
| D127 | | | 4.0000 | 0.4784 | 0.0858 |
| D128 | | | 4.0000 | 0.4525 | 0.0984 |
| D129 | | | 4.0000 | 0.1230 | 0.1074 |
| D131 | | | 0.4459 | 0.1210 | 0.1077 |
| D132 | | | 2.6356 | 0.1155 | 0.1059 |
| D133 | | | 3.9921 | 0.0954 | 0.0810 |
| D134 | | | 3.7527 | 0.0934 | 0.1237 |
| D135 | | | 2.5440 | 0.2019 | 0.0841 |
| D137 | | | 4.0000 | 0.3294 | 0.1063 |
| D139 | | | 3.5412 | 0.1102 | 0.1096 |

A number of clones showed reactivity to the peptide and little to no reactivity toward HER2-ECD (D3, D5, D7-11 and D13 of FIG. 1). Others showed reactivity to both HER2-ECD and the immunization peptide (D4, D6 and D12 of FIG. 1).

Conditioned media from clones were also used to stain blots of polyacrylamide gels run with lysates of SKBR3, 293T and 293T transfected with pcDNA6myc/hisA M611-p95 (see FIG. 2). 5 µg cell lysate from the SKBR3 and 293T cells or 1 µg cell lysate from the cells transfected with pcDNA6myc/hisA M611-p95 expression vector were separated on 4-12% NuPAGE gels (Invitrogen). The gels were blotted to PVDF membranes that were stained with conditioned media from hybridomas D4, D8, D12 or Her2 Ab8. Her2 Ab8 (Labvision, Fremont, Calif.) was used as positive control antibody and binds to an intracellular epitope of Her2 that is also part of p95. Bound antibodies were detected with a horseradish peroxidase-conjugated anti-mouse IgG antiserum and an ECL reagent. In Western blots, only D4, D8 and D12 showed significant binding, recognizing both full-length Her2 (in SKBR3 cell lysates) and p95 (in lysates of 293T cell transfected with p95 expression vectors). Antibodies A3, D3, D5, D6, D7, D9, D10, D11, D13 and all B and E antibodies did not produce specific signals in western blots (data not shown). Anti-HER2 Ab8 from Labvision was included as a positive control (see FIG. 2).

Hybridoma supernatants were screened by flow cytometry using HEK293F cells transiently transfected with HA-tagged, full-length Her2 or HA-tagged PcDNA6-p95. 293F cells were transfected using 293-fectin (Invitrogen, Carlsbad, Calif.) and incubated for 2 days. Cells were either directly used for staining or were fixed with paraformaldehyde before staining Hybridoma supernatants were added to cells. Bound antibodies were detected using a biotinylated anti-mouse IgG serum and streptavidin-phycoerythrin (native cells; Table 2, FIG. 3a) or a fluorescein-conjugated anti-mouse IgG serum (fixed cells; Table 3, FIG. 3b).

Antibodies could be roughly grouped into two classes based on binding to p95 or HER2 expressing 293 cells. Antibodies A3, D3, D5, D6, D7, D10 and D11 bound to native cells expressing pcDNA6-p95, but did not bind to cells expressing full-length Her2. Antibodies D4, D8, D9 and D12 bound to native cells expressing pcDNA6-p95 and to native cells expressing full-length Her2. Although full-length Her2 was recognized by these antibodies, binding was relatively weak as compared to the positive control antibodies HA.A28.2.

Table 2 shows the screening of hybridoma supernatants by flow cytometry with native cells. 293F cells transfected with HA-Her2 or pcDNA6-p95 or control 293F cells were stained with hybridoma supernatants. Mean fluorescence intensities (MFI), the percentages of stained cells and the MFI ratios are listed. The MFI ratio is the ratio of the MFI of a specific hybridoma supernatant and the MFI of the negative anti-ricin control antibody. Antibody HA.A28.2 specific for the HA-tag was used as positive control.

TABLE 2

| | 293F HA-Her2 | | | 293F pcDNA6-095 | | | Control 293F | | |
|---|---|---|---|---|---|---|---|---|---|
| samples | MFI | % stained cells | MFI ratio | MFI | % stained cells | MFI ratio | MFI | % stained cells | MFI ratio |
| anti-ricin | 0.29 | 0.8% | 1.0 | 0.24 | 0.9% | 1.0 | 0.26 | 0.9% | 1.0 |
| HA.A28.2 | 19.98 | 94.3% | 68.9 | 15.79 | 74.4% | 65.8 | 0.40 | 17.7% | 1.5 |
| A3 | 0.39 | 1.7% | 1.3 | 6.83 | 53.5% | 28.5 | 0.31 | 1.6% | 1.2 |
| D3 | 0.36 | 5.8% | 1.2 | 24.15 | 83.6% | 100.6 | 0.27 | 1.3% | 1.0 |
| D4 | 2.80 | 80.0% | 9.7 | 26.88 | 88.5% | 112.0 | 0.33 | 11.0% | 1.3 |
| D5 | 0.26 | 0.5% | 0.9 | 1.19 | 35.3% | 5.0 | 0.27 | 2.5% | 1.0 |
| D6 | 0.32 | 2.6% | 1.1 | 0.50 | 26.6% | 2.1 | 0.26 | 1.7% | 1.0 |
| D7 | 0.44 | 10.7% | 1.5 | 7.90 | 65.6% | 32.9 | 0.34 | 15.1% | 1.3 |
| D8 | 3.16 | 61.9% | 10.9 | 26.58 | 81.3% | 110.8 | 0.28 | 3.6% | 1.1 |
| D9 | 3.37 | 48.1% | 11.6 | 22.89 | 76.8% | 95.4 | 0.28 | 3.2% | 1.1 |
| D10 | 0.30 | 3.2% | 1.0 | 16.28 | 73.7% | 67.8 | 0.25 | 1.2% | 1.0 |
| D11 | 0.40 | 5.7% | 1.4 | 7.22 | 60.5% | 30.1 | 0.27 | 2.2% | 1.0 |
| D12 | 3.17 | 83.6% | 10.9 | 24.17 | 85.3% | 100.7 | 0.45 | 35.4% | 1.7 |
| D13 | 0.26 | 0.2% | 0.9 | 0.24 | 0.6% | 1.0 | 0.27 | 1.6% | 1.0 |

Antibodies A3, D5, D6, D7, D11 and D13 did not bind to formalin-fixed 293F cells expressing pcDNA6-p95 indicating that the fixation procedure modified the epitopes recognized by these antibodies. Antibodies D4 and D12 bound well to fixed 293F cells expressing either pcDNA6-p95 or Her2. Antibodies D3, D8, D9 and D10 bound well to fixed 293F cells expressing pcDNA6-p95, but did not bind or bound weakly to fixed cells expressing Her2.

Table 3 shows the screening of hybridoma supernatants by flow cytometry with formalin-fixed cells. 293F cells transfected with HA-Her2 or pcDNA6-p95 or control 293F cells were formalin-fixed and stained with hybridoma supernatants. Mean fluorescence intensities (MFI), the percent of stained cells and the MFI ratio are listed. The MFI ratio is the ratio of the MFI of a specific hybridoma supernatant and the MFI of the negative anti-ricin control antibody. Antibody HA.A28.2 specific for the HA-tag was used as positive control.

TABLE 3

| | 293F HA-Her2 | | | 293F pcDNA5-p95 | | | Control 293F | | |
|---|---|---|---|---|---|---|---|---|---|
| samples | MFI | % stained cells | MFI ratio | MFI | % stained cells | MFI ratio | MFI | % stained cells | MFI ratio |
| anti-ricin | 0.48 | 1.0% | 1.0 | 0.48 | 0.9% | 1.0 | 0.43 | 0.9% | 1.0 |
| HA.A28.2 | 2.12 | 60.8% | 4.4 | 1.96 | 36.6% | 4.1 | 0.56 | 12.3% | 1.3 |
| D3 | 0.54 | 4.2% | 1.1 | 1.49 | 27.4% | 3.1 | 0.47 | 3.2% | 1.1 |
| D4 | 1.21 | 35.2% | 2.5 | 2.24 | 38.4% | 4.7 | 0.49 | 6.3% | 1.1 |
| D5 | 0.33 | 0.3% | 0.7 | 0.36 | 1.8% | 0.8 | 0.29 | 0.2% | 0.7 |

TABLE 3-continued

|  | 293F HA-Her2 | | | 293F pcDNA5-p95 | | | Control 293F | | |
| --- | --- | --- | --- | --- | --- | --- | --- | --- | --- |
| samples | MFI | % stained cells | MFI ratio | MFI | % stained cells | MFI ratio | MFI | % stained cells | MFI ratio |
| D6 | 0.33 | 0.1% | 0.7 | 0.33 | 0.2% | 0.7 | 0.29 | 0.1% | 0.7 |
| D7 | 0.42 | 0.6% | 0.9 | 0.50 | 6.6% | 1.0 | 0.40 | 0.8% | 0.9 |
| D8 | 0.79 | 21.0% | 1.6 | 2.07 | 32.6% | 4.3 | 0.43 | 1.8% | 1.0 |
| D9 | 0.71 | 18.4% | 1.5 | 2.08 | 32.1% | 4.3 | 0.34 | 0.3% | 0.8 |
| D10 | 0.48 | 1.7% | 1.0 | 1.47 | 29.7% | 3.1 | 0.31 | 0.1% | 0.7 |
| D11 | 0.42 | 1.9% | 0.9 | 0.55 | 12.6% | 1.1 | 0.36 | 0.3% | 0.8 |
| D12 | 0.99 | 27.1% | 2.1 | 2.00 | 32.3% | 4.2 | 0.33 | 0.2% | 0.8 |
| D13 | 0.43 | 2.4% | 0.9 | 0.58 | 0.9% | 1.2 | 0.30 | 0.1% | 0.7 |
| anti-ricin | 0.48 | 1.0% | 1.0 | 0.48 | 0.9% | 1.0 | 0.43 | 0.9% | 1.0 |

Example 3: Production of FFPE Slides from Cell Lines with and without Expression of p95 Transgene Three breast cancer cell lines, MCF-7, MDA-MB-453 and SKBR-3, were purchased from American Type Cell Culture Collection. MCF-7-p95c (where "c" indicates a clonal line), MCF7-HER2c and SKBR3-p95c were obtained from the laboratory of Jose Baselga. These clones were made from a slightly different form of p95 containing no leader sequence or HA tag, as described in Anido et al. (2006) *EMBO J.*, 25:13, 3234. The p95-containing cell lines were generated by the transfection of parental MCF7 or SKBR3 cells with an expression vector containing a HindII fragment of full-length HER2 that allows translational initiation from several internal methionines, including Met611. MCF-7, MCF7-p95c, MCF7-HER2c and SKBR3-p95c were maintained at 37° C. in 5% $CO_2$ in 50:50 Dulbecco's modified Eagle medium (DMEM): F12, 10% fetal bovine serum (FBS), 1% penicillin-streptomycin (PS), 10 μg/mL bovine insulin and 2 mM L-glutamine. MDA-MB-453 and SKBR-3 were maintained at 37° C. in 5% $CO_2$ in 50:50 DMEM: F12, 10% FBS, 1% PS and 2 mM L-glutamine. Cells were plated at a density of 30 million per 500 $cm^2$. Cells intended for transient transfection were allowed to attach for 4 hours. The cells were transfected with Fugene HD (Roche) according to the manufacturer's instructions. The culture media was changed after 1 day and the cells were fixed on day 2. After removal of medium, the cells were washed once with 50 mL cold D-PBS (Invitrogen) and fixed with 50 mL of 10% NBF (neutral buffered formalin). Cells were left in a 4° C. cold room for 30 minutes then scraped from the culture plates. The cell slurry was collected into 50 mL centrifuge tubes and pelleted at 3200×g for 15 min. The cell pellet was transferred to a rubber O-ring, wrapped with filter paper and placed in a processing cassette. Automatic Tissue-Tek processor was used for processing. Briefly, the cell pellet was exposed to increasing concentrations of alcohol, Clear-rite (xylene substitute) and paraffin. After processing, pellet was embedded in a block using a paraffin embedding station. All solvents used for cell pellet processing were obtained from Richard-Allen Scientific.

Sections of 5 um in thickness were sliced with a microtome (LEICA) and placed on positively charged glass slides (VWR) with serial number labeled. Slides were air-dried for 30 min and then baked at 60° C. for 1 hr. All sample slides were stored at 4° C. for future use.

To verify expression of transgenes in transfected cells made into FFPE blocks, cell lysates were prepared from samples of cells removed and lysed just prior to the addition of NBF described above. Lysis Buffer contained 1% Triton X-100, 50 mM Tris-HCl (pH7.5), 150 mM NaCl, 50 mM NaF, 50 mM sodium beta-glycerophosphate, 1 mM $Na_3VO_4$, 5 mM EDTA, 10 μg/mL pepstatin and 1 tablet Complete Protease Inhibitor (Roche #1836170) in 10 mL water. Samples were mixed with 2× Laemmli buffer (Biorad) and heated to 70° C. for 10 minutes. Separately, protein content was assessed by bicinchoninic acid (BCA) assay (Pierce) according to the manufacturer's instructions. Twenty micrograms of protein per lane were loaded into a 4-12% gradient gel and run in a MOPS-based running buffer (Invitrogen) at 180 v for approximately 1 hour. Bands were transferred to a nitrocellulose membrane (Invitrogen) in Nu-PAGE transfer buffer (Invitrogen)+10% methanol at 45 v for 1.5 hours. The membrane blots were first blocked with PBST (1% Triton-X100 in PBS) plus 3% nonfat dry milk for 30 minutes with gentle shaking Following two 15 minute washes with PBST, blots were treated with 1.0 μg/mL anti-HER2 Ab8 in PBST plus 0.03% nonfat dry milk overnight with gentle shaking Following two 15 minute washes with PBST, blots were next treated with a 1:50,000-fold dilution of a goat anti-mouse linked with horseradish peroxidase (Pierce #31430) with gentle shaking for 30 minutes. Following two 20 minute washes with PBST the blots were developed with the West Dura HRP detection kit (Pierce) according to the manufacturer's instructions with images captured on film (Kodak). FIG. 4 shows results from a representative set of cells that were subsequently made into FFPE blocks then cut into slides. Lane 1 shows an expected small amount of material in the p95 region that is not found in the MCF7 lane 5 (Anido et al. (2006) *EMBO J.* 25:13, 3234). Some evidence of this weak p95 band is also seen in the transient-transfected MCF7-HER2 of lane 6 using a 50:50 weight mix of pcDNA6-HER2 and pcDNA6 vector. Lanes 2-4 show the expected expression of full-length HER2 and p95 in the clonal lines. The cells assayed in Lane 7 were transfected with the same amount of pcDNA6-HER2 as the cells in lane 6 but with pcDNA6myc/hisA M611-p95 substituted for the empty vector. Lane 8 shows the results of MCF7 cells transfected with 100% pcDNA6myc/hisA M611-p95. Lane 9 shows SKBR3 cells, useful for comparison against lanes 3 and 4. The untransfected SKBR3 shows a band in the lower region of the p95 region but not the upper bands shown in the transfected lines. This is not unexpected as SKBR3 is known to shed some amount of HER2-ECD (Zabrecky et al. (1991) *J. Biol. Chem.* 266:3 1716).

Example 4: Screening of Anti-p95 Antibodies by Veratag Assay

The monoclonal antibody Ab8 against cytoplasmic domain of HER2 was purchased from Lab Vision. A goat anti-mouse antibody was purchased from Thermo Scientific (#31164) VeraTag reporters (Pro125 and Pro14) were synthesized and purified according to protocol described previously (See, for example, above and U.S. Pat. No. 7,105,308, which is incorporated by reference herein, including any drawings). Antibody-VeraTag and antibody-biotin conjugates, i.e., Ab8-biotin, goat anti-mouse-Pro125 anti-p95-Pro125, were made using sulfo-NHS-LC-LC-biotin (Pierce) as linker according to manufacturer's protocol and conjugation products purified by HPLC (Agilent) or PD-10 desalting column (GE).

A p95 FFPE assay was carried out essentially as shown in FIG. 5a. FFPE samples were deparaffinized/rehydrated using a series of solvents. Briefly, slides were sequentially soaked in xylene (2×, 5 min), 100% ethanol (2×, 5 min), 70% ethanol (2×, 5 min) and deionized water (2×, 5 min). Heat-induced epitope retrieval of the rehydrated samples was performed in a dish containing 250 mL of 1× Diva buffer (Biocare Medical #DV2004MM) using microwave oven (Spacemaker II, GE): 3.5 min at power 10 followed by 10 min at power 3. After being cooled down for 1 hour at room temperature, the slides were rinsed six times with deionized water. Slides were partially dried in a centrifuge (Tomy PMC-082) modified to spin slowly. A hydrophobic circle was drawn on the slide using a hydrophobic pen (Zymed) to retain reagents on slides. The samples were then blocked for 1 hr with Blocking Buffer that contained 10% goat serum (Sigma #S1000) and 1.5% bovine serum albumin in 1×PBS. After removal of the Blocking Buffer with aspiration, a solution containing the anti-p95 antibody in Blocking Buffer was added to the slides and left at 4° C. overnight in a humidified chamber with gentle shaking. The concentration of anti-p95 antibody was 1.0 µg/mL for screening of multiple antibodies, otherwise 4 µg/mL of D9.1 antibody was used. The antibody solution was aspirated and samples were washed with PBS containing 0.25% TritonX-100 for 5 minutes then PBS alone for 5 minutes. Following aspiration, 50 µL of 1.0 µg/mL goat anti-mouse antibody labeled with VeraTag in Blocking Buffer was added. This antibody was allowed to incubate at room temperature for 1.5 hours in a humidified chamber. The slides were next rinsed with deionized water followed by PBS containing 0.25% TritonX-100 for 5 minutes. Slides were then loaded onto racks and submerged in deionized water 6 times. Following centrifugation of the slides, 100 µL Capture Buffer containing 1.0 mM dithiothreitol (DTT), 3 pM fluorescein and two CE internal markers (MF and ML) in 0.01×PBS was added on sample sections. Slides were incubated in a humidified chamber for 2 hours to allow for the release of the VeraTag. Capture Buffer from each slide was transferred to a CE 96-well plate then diluted appropriately (generally 10-fold) in Capture Buffer not containing DTT. The released VeraTag reporters in the CE samples were separated and detected on a ABI3100 CE instrument (22-cm capillary array, Applied Biosystems) under the CE injection condition of 6 kV and 50 sec and run for 650 seconds at 30° C.

The identification and quantification of VeraTag was carried out using VeraTag Informer software (see, for example, United States publication number 0203408-A1, which is incorporated by reference herein, including any drawings). To analyze the VeraTag signals in a raw CE electropherogram, two CE internal markers, MF (first marker) and ML (last marker), were used to identify the VeraTag peaks according to their electrophoretic mobility or migration time, t, relative to the two markers, i.e., [t(VeraTag)-t(MF)]/[t(ML)-t(MF)]. The identified VeraTag peaks were then quantified by peak area calculation for each VeraTag. To correct for variability in VeraTag recovery from the tissue section, and the run variability in CE injection efficiency and/or detection sensitivity across capillary array, fluorescein (3 pM) was included in the VeraTag Capture Buffer (CB), and co-electrophoresed as an internal reference control in each sample run. The area of each VeraTag peak was then reported as relative peak area (RPA) by area normalization of the VeraTag peak (VeraTag peak area) to the internal fluorescein peak (fluorescein peak area).

Slides were stained with hematoxylin and eosin (H&E) by standard techniques. Briefly, slides were placed in staining racks and first rinsed in tap water. Slides were serially dipped in hematoxylin, clarifier and bluing agent for 45 seconds each, followed by tap water rinses after each step. Slides were then treated with 5% water in alcohol (2 fresh solutions) then 100% alcohol (3 fresh solutions) then xylene (3 fresh solutions, 5 minutes each). Finally, a coverslip was applied to protect the section. Tumor areas were outlined on the H&E-stained sections by a board-certified pathologist using a fine-tipped permanent pen. Section areas for cell line slides were similarly outlined. Tumor areas and section areas for cell lines were quantified by image capture on a flat-bed scanner and analyzed using ImagePro software (Media Cybernetics).

The final quantification terms for the target protein detected by the VeraTag assay can be either RPA for similar samples with identical CB volume or the RPA*CB vol/tumor area to account for different amounts of tumor on the slides. This is generally expressed as RPA*µL/cm². The reproducibility between samples tested on different days and different days compared to the mean is shown in FIG. 5b. The diagonal in each plot indicates perfect correlation. To adjust for batch to batch variability, multiple standard cell lines of expected signal levels are included in each batch to facilitate normalization. The results for a range of transfected cell lines with varying amounts of p95, pre- and post-normalization, for 3 different operators, are shown in FIG. 5c. Batch to batch normalization is limited to a multiplication by a single factor for each batch that achieves a least squares fit of the log of the measurement on these standards to the log of their expected values. Expected values of each standard are established by measuring all standards (typically 3) in a single batch with multiple replicates, with the replicates running over multiple batches. As new production lots of each standard are introduced, the new lot is measured with multiple replicates against the current set of standards to establish an expected value to be associated with that particular lot.

Results from a series of antibodies from the Series D immunization is shown in FIG. 6, compared against anti-HER2 Ab8. D4.1 and D12.1 behaved much like Ab8, indicating that the epitope recognized by these antibodies is detected equally well in p95 as full-length HER2. D8.1 and D9.1 however show about 10-fold stronger signal from the p95-expressing cell lines (MCF7-p95, MCF7-p95c and SKBR3-p95c) than their parental lines (MCF7 and SKBR3), demonstrating specificity for p95. Even though full-length HER2 contains the same peptide sequence as p95, the epitopes of at least D8.1 and D9.1 are likely hidden in full-length HER2 in the FFPE format. MCF7-HER2c shows a modestly increased signal above MCF7, consistent with the small amount of p95 found in FIG. 4, lane 1.

Example 5: Quantification of p95 in FFPE Slides of Primary Breast Cancer Tumors

A set of 12 breast cancer tumors were obtained from Asterand (Cohort A). These tumors were chosen to be highly HER2-positive (Allred score of 8), and came from patients with node-positive status. Both of these factors are known to correlate with p95-positivity. The tumors were prepared by Asterand such that approximately half of the tumor was fresh frozen and half was formalin-fixed and paraffin-embedded. This enabled detection of p95 by Western blot, which should imply p95 expression in FFPE slides cut from the matching portion of tumor.

The frozen portion of the tumors was lysed by grinding under liquid nitrogen with a mortar and pestle until a power was obtained. A minimum amount of cold lysis buffer (about 600 μL) was added and the mortar was left on ice for 30 minutes. Lysis Buffer contained 1% Triton X-100, 50 mM Tris-HCl (pH7.5), 150 mM NaCl, 50 mM NaF, 50 mM sodium beta-glycerophosphate, 1 mM $Na_3VO_4$, 5 mM EDTA, 10 μg/mL pepstatin and 1 tablet Complete Protease Inhibitor (Roche #1836170) in 10 mL water. The solution was collected into pre-chilled microfuge tubes and centrifuged at 4° C. for 20 minutes. Aliquots were stored at −80° C. until use.

A Western blot (FIG. 7a) stained with an antibody raised against the intracellular domain of HER2, CB11 (Ventana), showed that several tumors expressed p95 with various levels of expression. Tumors 1-3, 5, 7, 8 and 10 were designated as p95 positive while all others were designated p95-negative. FFPE slides from all 12 tumors along with 7 cell line standards were tested in the assay described in Example 4, using the clone D9.1 (FIG. 7b). The distinction between p95-positive and p95-negative FFPE tumors was nearly perfect (replotted in FIG. 7c), especially considering the possibility of heterogeneity between the portion that was lysed for the Western and that which was fixed for the FFPE p95 assay.

Example 6: Demonstration of Sensitivity by an Isotype Control Experiment

The sensitivity of the FFPE p95 assay was further demonstrated by comparison with control measurements where the D9.1 antibody was swapped with an isotype control (FIG. 8a). For both MCF-7 and the high HER2-expressor SKBR3, the signal generated with D9.1 was not much different from the signal generated when D9.1 was replaced with its isotype control. Conversely, when p95 is present (MCF7-p95 transient, MCF7-p95 clone and SKBR3-p95) signals generated in the presence of D9.1 far exceeds the isotype control. For the tumors, p95-positive tumors showed signals using D9.1 well above those where the isotype control is used whereas most of the p95-negatives showed signals similar to those where D9.1 was absent (FIG. 8b). FIG. 8c shows the difference between the signals generated using D9.1 and the isotype control. The difference in the means of p95-positive and p95-negatives is approximately 4-fold with a dynamic range of approximately 10-fold.

Example 7: Increased Likelihood of p95-Positivity in Samples Measured to be Highly HER2-Positive by the HERmark® HER2-Total Assay The VeraTag HER2 total (H2T) assay quantifies the amount of HER2 protein per unit area of invasive tumor as described in U.S. patent application No. 61/015,608, which is incorporated by reference herein, including any drawings. As p95 is expected to be more prevalent in tumors that score at the high end of HER2-positive by IHC or H2T, the tumors used in Example 5 were tested by the H2T assay to search for a possible cutoff. The tumors were found to span the range of HER2-positivity as assessed by the H2T assay (FIG. 9a), however the p95-positives were significantly higher by H2T than the p95-negatives.

A second set of 18 FFPE tumors (Cohort B) was obtained from Asterand to further explore the distribution of p95 within the H2T landscape. Slides from these tumors were assessed by both the p95 assay as described in Example 4 and the H2T assay. Correlative results for both Cohort A and B are presented in FIG. 9b. A higher p95 signal is more likely to be found with high H2T for both cohorts.

It was therefore hypothesized that trastuzumab-treated patients with H2T scores more consistent with the p95-positive tumors measured in Cohort A should have worse outcomes than those with lower H2T scores since p95 is lacking the trastuzumab epitope and is therefore a likely means of escape. To test this hypothesis, a cohort of trastuzumab-treated patients whose tumors had previously been assessed for H2T were investigated for evidence of poor outcomes in the range of H2T expected to be enriched in p95. This cohort is further described in U.S. patent application No. 61/015,608, which is incorporated by reference herein including any drawings. This cohort (N=92) was derived from the International Serum Her2/neu Study Group (ISHSG) and is called the Lipton cohort. These patients were selected primarily by IHC performed at a central location—the University of Vienna in Austria—by a single pathologist. 90% of patients were IHC 3+, and 80/92 received trastuzumab in combination with chemotherapy, while 12 received trastuzumab as a single drug. 88/92 patients had metastatic breast cancer, and they could have received trastuzumab either as first, second or third line therapy.

For these analyses, a cutoff for H2T was chosen just above the highest p95-negative shown in FIG. 9a, at a value of $\log_{10}(H2T) \geq 1.95$. Above this H2T cutoff, tumors could be described as p95-enriched while those below the cutoff would be p95-equivocal. Among the patients confirmed to be HER2-FISH-positive by central lab analysis, those in the p95-enriched group had significantly shorter time-to-progression (HR=2.0; p=0.017) than those that were in the p95-equivocal group (FIG. 9c). The overall survival results (FIG. 9d) were similar (HR=1.8; p=0.056). These results suggest that a highly quantitative measure of HER2 expression, such as the VeraTag H2T assay, can identify subpopulations expected to be enriched in patients with tumors that contain p95 to the degree that trastuzumab is significantly less effective. This subpopulation would then be candidates for alternative treatments such as HER2 tyrosine kinase inhibitors.

Example 8: Colorimetric Immunohistochemistry of FFPE Cell Lines and Tumours with an Anti-p95 Antibody Parental or p95-CTF-transfected breast tumor cell lines SKBR3 or SKBR3-p95c (~1×10⁶p185-HER2/cell) were grown, formaldehyde fixed, and prepared for FFPE sections as described in Example 3. Staining for p95 or full-length HER2 was performed using the Vectastain ELITE ABC Peroxidase kit (PK 6102), the ImmPact DAB peroxidase substrate (Vector #SK4105), and horse serum from the Vectastain kit. The cells were counterstained with hematoxylin (Vector #H3401). FFPE cells in paraffin blocks were microtome cut to 5 μm thickness and placed on glass slides. The epitope retrieval process was similar to Example 4. Briefly, sections were deparaffinized by standard sequential xylene, 100% ethanol and 70% ethanol extractions, and epitope retrieval was performed in DIVA buffer and raised to a boil in a microwave oven (3.5 min at power=10, followed by 10 min at power=3). Following cooling for 1 hour, sections are washed 6× with water, blocked with horse serum containing blocking buffer for 1 hr at room temperature (RT), then incubated with 4 μg/mL of D9.1 anti-p95 monoclonal antibody in blocking buffer for 1 hour at RT. The sections are washed with PBS and the secondary antibody addition and subsequent color development and hematoxylin staining steps were performed as described in the manufacturer's kit protocol. Cell micrographs were taken with a digital camera image capture system mounted on a Leica microscope. The results are shown in FIG. 10.

FIG. 10a shows staining by the p95-recognizing D9.1 antibody of several cell lines. In the parental MCF7 cells, which express low levels of Her2, little staining is observed. In MCF7 cells transfected with a p95 expression vector, high levels of staining are seen; however, in cells transfected with full length Her2 expression vectors, staining is not seen, verifying the specificity of the D9.1 antibody. In the parental SKBR-3 cells, which express high amounts of full-length HER2 and low levels of p95, little cell membranous staining is observed, consistent with the low level of p95; in contrast, in cells transfected with CTF (C-terminal fragment), which is an intracellular domain of Her2, strong staining is observed. Control experiments using a human IgG2a isotype control antibody replacing D9.1 (IgG2a isotype) lacked the cell membranous staining observed for D9.1, indicating specificity of the D9 staining (data not shown).

Slides from Cohort A described in Example 5 were used to test the ability of D9.1 to detect p95 in FFPE tumors. As described in Example 5, #5 was identified as positive for p95 by Western blot analysis whereas #6 and #12 was negative. FFPE sections were examined for IHC staining by D9.1 or CB-11 antibodies as described above in Example 8, using the Vectastain ELITE ABC Peroxidase kit (PK 6102). The cells were counterstained with hematoxylin (Vector #H3401).

FIG. 10b represents staining by the p95-recognizing D9.1 antibody of the p95-positive #5. Strong cell membranous staining is observed, consistent with p95 expression observed in the Western blot and VeraTag assay. Similar strong membranous staining is observed with CB11, consistent with high expression of p95- and p185-HER2 observed by Western blotting and HER2 VeraTag assay. FIG. 10b also shows the absence of cell membranous staining by D9.1 antibody applied to tumor #12 and #6 and is consistent with the absence of p95 by Western blot and VeraTag assay. However, the significant full-length HER2 levels found by Western blot and VeraTag assay of #5 is consistent with the strong membranous staining observed with CB-11, an antibody targeted to the intracellular domain of Her2. Taken together with the cell line control staining, the data supports results from the p95 VeraTag assay indicating preferential binding of the D9.1 antibody to p95 compared to full-length HER2. Furthermore, the data suggest that the amino acid sequence recognized by D9.1 is contained in naturally occurring forms of p95 expressed in breast tumors. Control experiments using a human IgG2a isotype control antibody replacing D9.1 (IgG2a isotype) lacked the cell membranous staining observed for D9.1, indicating specificity of the D9.1 staining on tumor tissues (data not shown).

Example 9: Quantitation of p95 Using Directly Labeled Anti-p95 Antibodies in a VeraTag Assay In Example 4, p95 was measured in FFPE slides using specific anti-p95 antibodies in conjunction with an anti-mouse secondary antibody labeled with a cleavable vTag. In this example, p95 was measured with directly labeled p95 antibodies. The assay method is identical to that described in Example 4 except that the addition of labeled secondary and subsequent wash was omitted and D9-Pro125 was used at 1.0 μg/mL. The results presented in FIG. 11 are similar to those shown in FIG. 6 with possible reduction in the dynamic range between p95-low/negative cell lines (MCF7, MCF7-HER2, SKBR3) and the p95-high cell lines (MCF7-p95c, MCF7-p95 and SKBR3-p95c). The D9.1 antibody was also used in this format in a batch of cell lines (FIG. 12a) and tumors from Cohort A (FIG. 12b).

Example 10: Quantitation of p95 Using an Anti-p95 Antibody and an Antibody Directed Against the Intracellular Domain of HER2 in a VeraTag Assay In this example, the specificity of D9.1 was paired with anti-HER2 Ab8 (clone e2-4001) from Labvision in the form of a cleavable VeraTag assay as described in U.S. patent application No. 61/015,608, which is incorporated by reference herein, including any drawings. In this example anti-HER2 Ab8 labeled with biotin at 2 μg/mL was used with anti-p95 D9.1 at 2 μg/mL. Results from this form of the assay are presented in FIGS. 12c and 12d. Separation of p95-positive and p95-negatives is retained with this form of the assay.

Example 11: Growth Inhibition of a Breast Cancer Cell Line Using Anti-p95 Antibodies The antibodies from the D-series of immunizations were tested for their ability to inhibit growth of the high-HER2 expressing cell lines SKBR3 and BT474. SKBR3 and BT474 cells were plated in ½-area 96-well plates at a density of 120 k/well and 240 k/well, respectively. SKBR3 cells were cultured in 100 μL McCoy's 5A (ATCC) 10% FBS, 1% penicillin-streptomycin and 2 mM L-glutamine. BT474 cells were maintained in 100 μL at 37° C. in 5% $CO_2$ in 50:50 DMEM: F12, 10% FBS, 1% penicillin-streptomycin and 2 mM L-glutamine. After cells were allowed to attach for 4 hours, purified antibodies listed in FIG. 13 were added to final concentrations of 1.0, 3 and 10 μg/mL. 4D5 included as a positive control. The cells were allowed to grow for 3 days before cell growth was assessed by the XTT assay (Sigma) per the manufacturer's instructions. The difference in absorbance at 492 nm and 690 nm was taken as proportional to the number of cells in each well. These results (FIG. 13) suggest that D3.4 and to some degree D4.1 inhibit the growth of SKBR3 cells but not BT474. This difference in reactivity towards two cells lines with near equally high levels of HER2 expression may be explained by the fact that SKBR3 is know to shed greater levels of HER2 extracellular domain into the media and therefore may be more dependent on p95 retained in the cell.

Example 12: Very High Levels of Her2 Correlates with Poor Response to Trastuzumab The HERmark® assay was used to measure the total Her2 protein (H2T) per unit area of invasive tumor tissue (as described in U.S. Patent Application No. 61/015,608, which is incorporated by reference herein, including any drawings) in formalin-fixed, paraffin-embedded (FFPE) primary breast tumor specimens from 99 women treated with trastuzumab for metastatic breast cancer (MBC). Table 4 shows the characteristics of the patient population from which the tumors were derived. Specimens were also tested by central FISH.

TABLE 4

Patient Characteristics

| Characteristic | Value (range, %) | Characteristic | Value (range, %) |
|---|---|---|---|
| Total Patients | 99 | Treatment | |
| Mean Follow Up (months) | 32.0 (11.8-72.3) | Trastuzumab + chemotherapy | 87 (87.9%) |
| Mean Age | 55.2 (27.6-85.4) | Trastuzumab only | 12 (12.1%) |
| Hormonal Status | | Line of chemotherapy | |
| | | First line | 72 (72.7%) |
| ER+PR+ | 15 (15.2%) | Second line | 17 (17.2%) |
| ER+PR− | 19 (19.2%) | Third line | 8 (8.1%) |
| ER−PR+ | 3 (3%) | Unknown | 2 (2.0%) |
| ER−PR− | 60 (60.06%) | Number of metastatic sites | |
| Unknown | 2 (2.0%) | <3 | 57 (57.6%) |
| | | ≥3 | 42 (42.4%) |

A sub-population treatment effect pattern plot (STEPP) was generated to examine the progression-free survival (PFS) rate at 12 months after treatment with trastuzumab across the distribution of H2T. Bins of 30 patients were ordered smallest to largest H2T. The results are shown in FIG. 14. A trend of increasing probability of remaining progression-free past 12 months was observed for increasing H2T. However, at the highest levels of H2T, an abrupt decrease in the PFS rate was observed, consistent with a reduction in susceptibility to trastuzumab.

Kaplan-Meier (KM) analyses were performed comparing the PFS of FISH(−), H2T low ($\log_{10}H2T<1.25$) patients with those of FISH(+), H2T high ($Log_{10}H2T\geq1.95$ and FISH(+), H2T intermediate ($1.25<\log_{10}H2T<1.95$). Cut-offs were identified by lowest p-value in a positional scanning analysis. KM analyses demonstrated that patients who were FISH(+), H2T intermediate had a significantly longer PFS than patients who were FISH(−), H2T low (median PFS 12.6 vs. 4.5 months; hazard ratio (HR)=0.34; p<0.0001). Patients that were FISH(+), H2T high experienced a PFS that was no better than patients that were FISH(−), H2T low (median PFS 4.6 vs. 4.5 months; HR=0.87; p=0.68). The results of the KM analyses are shown in FIG. 15. The HERmark® assay identified patients with tumors having highly over-expressed HER2 and poor performance on trastuzumab. Neither the magnitude of HER2 over-expression nor the outcome for this subgroup was predictable by FISH/CEP17 copy number. MBC patients with very high levels of H2T may represent a subset of patients with de novo resistance to trastuzumab.

While the applicants do not wish to be confined to any particular mechanistic theory, possible mechanisms that may account for the poor response to trastuzumab observed in this subgroup may include:

insufficient trastuzumab increased signaling via formation of heterodimers that are not completely suppressed by trastuzumab generation of C-terminal fragments of Her2 such as HER2p95. Six of the 15 patients in the very high H2T subgroup were HER2p95-positive by the p95 VeraTag assay.

BIOLOGICAL DEPOSITS

A deposit of three hybridoma cell lines that produce the monoclonal antibodies referred to herein as p95.D3.4, p95.D8.2 and p95.D9.1 was made on Jan. 28, 2009, to the American Type Culture Collection (ATCC, 10801 University Blvd., Manassas, Va.) under conditions prescribed by the Budapest Treaty. The ATCC accession numbers for the deposited hybridoma cell lines are as follows: PTA-9738 (p95.D3.4), PTA-9739 (p95.D8.2) and PTA-9740 (p95.D9.1). As required under the Budapest Treaty, the cell lines will be irrevocably and without restriction or condition released to the public upon the issuance of a patent.

All publications and other materials described herein are used to illuminate the invention or provide additional details respecting the practice and are incorporated by reference in their entirety.

The invention claimed is:

1. A method of producing antibodies specific for a p95Her-2 protein fragment having a first amino acid corresponding to methionine 611 of Her-2 protein comprising growing a hybridoma cell line having ATCC accession number PTA-9738 (p95.D3.4), PTA-9739 (p95.D8.2), or PTA-9740 (p95.D9.1) in cell culture medium thereby producing said antibodies.

2. The method of claim 1, wherein said antibodies are purified from said cell culture medium.

3. The method of claim 1, wherein the antibodies are purified by one or more of dialysis, affinity chromatography, gel electrophoresis, protein A-agarose chromatography, or protein L-agarose chromatography.

* * * * *

SEQUENCE LISTING

```
<160> NUMBER OF SEQ ID NOS: 7

<210> SEQ ID NO 1
<211> LENGTH: 46
<212> TYPE: PRT
<213> ORGANISM: Artificial Sequence
<220> FEATURE:
<223> OTHER INFORMATION: Synthetic polypeptide p95 peptide for raising
      antibody

<400> SEQUENCE: 1

Met Pro Ile Trp Lys Phe Pro Asp Glu Glu Gly Ala Cys Gln Pro Cys
1               5                   10                  15

Pro Ile Asn Cys Thr His Ser Cys Val Asp Leu Asp Asp Lys Gly Cys
            20                  25                  30

Pro Ala Glu Gln Arg Ala Ser Pro Leu Thr Ser Ile Ile Ser
        35                  40                  45

<210> SEQ ID NO 2
<211> LENGTH: 9
<212> TYPE: PRT
<213> ORGANISM: Artificial Sequence
<220> FEATURE:
```

```
<223> OTHER INFORMATION: Synthetic polypeptide p95 peptide for raising
      antibody

<400> SEQUENCE: 2

Ala Ser Pro Leu Thr Ser Ile Ile Ser
1               5

<210> SEQ ID NO 3
<211> LENGTH: 14
<212> TYPE: PRT
<213> ORGANISM: Artificial Sequence
<220> FEATURE:
<223> OTHER INFORMATION: Synthetic polypeptide p95 peptide for raising
      antibody

<400> SEQUENCE: 3

Pro Ala Glu Gln Arg Ala Ser Pro Leu Thr Ser Ile Ile Ser
1               5                   10

<210> SEQ ID NO 4
<211> LENGTH: 21
<212> TYPE: PRT
<213> ORGANISM: Artificial Sequence
<220> FEATURE:
<223> OTHER INFORMATION: Synthetic polypeptide p95 peptide for raising
      antibody

<400> SEQUENCE: 4

Gln Pro Cys Pro Ile Asn Cys Thr His Ser Cys Val Asp Leu Asp Asp
1               5                   10                  15

Lys Gly Cys Pro Ala
            20

<210> SEQ ID NO 5
<211> LENGTH: 12
<212> TYPE: PRT
<213> ORGANISM: Artificial Sequence
<220> FEATURE:
<223> OTHER INFORMATION: Synthetic polypeptide p95 peptide for raising
      antibody; p95.D peptide used for immunization

<400> SEQUENCE: 5

Met Pro Ile Trp Lys Phe Pro Asp Glu Glu Gly Ala
1               5                   10

<210> SEQ ID NO 6
<211> LENGTH: 15
<212> TYPE: PRT
<213> ORGANISM: Artificial Sequence
<220> FEATURE:
<223> OTHER INFORMATION: Synthetic polypeptide p95 peptide for raising
      antibody; p95.E peptide used for immunization

<400> SEQUENCE: 6

Pro Ser Gly Val Lys Pro Asp Leu Ser Tyr Met Pro Ile Trp Lys
1               5                   10                  15

<210> SEQ ID NO 7
<211> LENGTH: 23
<212> TYPE: PRT
<213> ORGANISM: Artificial Sequence
<220> FEATURE:
<223> OTHER INFORMATION: Synthetic polypeptide p95 peptide for raising
      antibody
<220> FEATURE:
<221> NAME/KEY: MOD_RES
<222> LOCATION: (1)..(1)
<223> OTHER INFORMATION: ACETYLATION
```

```
<220> FEATURE:
<221> NAME/KEY: MOD_RES
<222> LOCATION: (23)..(23)
<223> OTHER INFORMATION: Lys as position 23 linked to keyhole limpet
      hemocyanin (KLH) via epsilon amino group (K(epsilonNH)-KLH))

<400> SEQUENCE: 7

Gln Pro Cys Pro Ile Asn Cys Thr His Ser Cys Val Asp Leu Asp Asp
1               5                   10                  15

Lys Gly Cys Pro Ala Lys Lys
            20
```